United States Patent
Law et al.

(10) Patent No.: US 11,173,182 B1
(45) Date of Patent: Nov. 16, 2021

(54) PLACENTA-DERIVED ADHERENT CELL EXOSOMES AND USES THEREOF

(71) Applicant: Celularity Inc., Florham Park, NJ (US)

(72) Inventors: Eric Law, Florham Park, NJ (US); Andrew Morschauser, Florham Park, NJ (US); Aleksander Francki, Florham Park, NJ (US); Jennifer Paredes, Florham Park, NJ (US); Kathy Karasiewicz-Mendez, Florham Park, NJ (US); Allan Reduta, Florham Park, NJ (US); Vladimir Jankovic, Florham Park, NJ (US); Ivana Djuretic, Florham Park, NJ (US); Robert J. Hariri, Florham Park, NJ (US)

(73) Assignee: Celularity Inc., Florham Park, NJ (US)

(*) Notice: Subject to any disclaimer, the term of this patent is extended or adjusted under 35 U.S.C. 154(b) by 0 days.

(21) Appl. No.: 16/740,054

(22) Filed: Jan. 10, 2020

Related U.S. Application Data

(63) Continuation of application No. 15/517,438, filed as application No. PCT/US2015/054629 on Oct. 8, 2015, now abandoned.

(60) Provisional application No. 62/062,046, filed on Oct. 9, 2014.

(51) Int. Cl.
| | |
|---|---|
| *C07H 21/04* | (2006.01) |
| *A61K 35/50* | (2015.01) |
| *C12N 5/0775* | (2010.01) |
| *C12N 5/073* | (2010.01) |
| *A61K 31/7105* | (2006.01) |
| *A61P 17/02* | (2006.01) |
| *A61P 9/00* | (2006.01) |
| *A61K 35/28* | (2015.01) |

(52) U.S. Cl.
CPC .......... *A61K 35/50* (2013.01); *A61K 31/7105* (2013.01); *A61K 35/28* (2013.01); *A61P 9/00* (2018.01); *A61P 17/02* (2018.01); *C12N 5/0605* (2013.01); *C12N 5/0668* (2013.01)

(58) Field of Classification Search
CPC .................................................. A61K 35/50
See application file for complete search history.

(56) References Cited

U.S. PATENT DOCUMENTS

| | | | |
|---|---|---|---|
| 2010/0184046 A1* | 7/2010 | Klass | C12Q 1/6811 |
| | | | 435/7.1 |
| 2011/0250182 A1 | 10/2011 | Abbot | |
| 2012/0202209 A1 | 8/2012 | Cavaille | |
| 2013/0195899 A1* | 8/2013 | Ichim | A61K 35/12 |
| | | | 424/184.1 |
| 2013/0245103 A1 | 9/2013 | De Fougerolles | |
| 2013/0337558 A1 | 12/2013 | Meiron | |
| 2014/0179770 A1 | 6/2014 | Zhang | |
| 2014/0220580 A1 | 8/2014 | Brown | |

FOREIGN PATENT DOCUMENTS

| | | | |
|---|---|---|---|
| CA | 2860144 | | 6/2013 |
| WO | 2014022852 | | 2/2014 |
| WO | 2014028493 | | 2/2014 |
| WO | WO 2014022852 | * | 2/2014 |
| WO | 2014100434 | | 6/2014 |
| WO | 2014145075 | | 9/2014 |

OTHER PUBLICATIONS

Meng, Xiaolong, et al.("Endometrial regenerative cells: a novel stem cell population." Journal of translational medicine 5.1 (2007): 57).*
Mincheva-Nilsson Lucia et al, "The role of placental exosomes in reproduction.", American Journal of Reproductive Immunology (New York, N.Y.: 1989) Jun. 2010, (Jun. 2010), vol. 63, No. 6, ISSN 1600-0897, pp. 520-533, XP002780464.
Ding et al., "Permanent Alteration of PCSK9 With in Vivo CRISPR-Cas9 Genome Editing", Circ Res., (Aug. 15, 2014), vol. 115, pp. 488-492, XP055428398.
Vandenboorn et al., "SiRNA delivery with exosome nanoparticles", Nature Biotechnology, (Apr. 1, 2011), vol. 29, No. 4, pp. 325-326, XP055428399.
Lai et al., "Proteolytic Potential of the MSC Exosome Proteome: Implications for an Exosome-Mediated Delivery of Therapeutic Proteasome", International Journal of Proteomics, (Jun. 1, 2012), vol. 2012, XP055155534.

* cited by examiner

*Primary Examiner* — Kimberly Chong
(74) *Attorney, Agent, or Firm* — Geoffry T. Knudsen

(57) ABSTRACT

Provided herein are compositions of placenta-derived adherent cell exosomes and methods of making and using the same. In one aspect, provided herein are compositions comprising exosomes produced by and/or derived from placental cells, e.g., placenta-derived adherent cells. In certain embodiments, the exosomes provided herein are produced by placenta-derived adherent cells that have been cultured in vitro for, e.g., 1, 2, 3, 4, 5, 6 or more passages.

14 Claims, 22 Drawing Sheets

FIG. 8C

| 18S | GAPDH | HPRT1 | GUSB | ACTA1 | ACTA2 |
|---|---|---|---|---|---|
| ACTB | ACTG1 | ACTG2 | AKT1 | BAD | CASP9 |
| FIGF | GRB2 | HRAS | HSP90AA1 | HSPB1 | KDR |
| KRAS | MAP2K1 | MAP2K2 | MAP2K4 | MAP2K6 | MAPK1 |
| MAPK14 | MAPKAPK2 | MAPK3 | NOS3 | NRAS | PIK3CA |
| PIK3CB | PIK3R1 | PLA2G4A | PLCG1 | PRKCA | PRKCB |
| PRKCD | PRKCE | PRKCZ | PTK2 | PTK2B | PXN |
| RAF1 | SHC1 | SOS1 | SRC | VEGFA | VEGFC |

PLACENTA-DERIVED ADHERENT CELL EXOSOMES AND USES THEREOF

This application claims benefit of U.S. Provisional Patent Application No. 62/062,046, filed Oct. 9, 2014, the disclosure of which is incorporated by reference herein in its entirety.

1. FIELD

The disclosure herein relates to compositions of placenta-derived adherent cell exosomes and methods of making and using the same.

2. BACKGROUND

Exosomes are small, non-cellular bodies derived from living cells. Generally, exosomes are 50-150 nanometers (nm) in diameter and composed of a phospholipid bilayer derived from multivesicular bodies or the plasma membrane of eukaryotic cells. Exosomes may be round in shape but also can be "cup-shaped" bodies that are visually identifiable using electron microscopy and other imaging techniques. Exosomes do not contain an intact nucleus or the requisite cellular components to support the metabolic and/or molecular functions of a cell, but exosomes may contain proteins, nucleic acids, and other molecules, or can be decorated with surface proteins, which can aid in their detection and isolation. The content of exosomes can reflect the cell-type from which they are derived and can consist of molecular markers that reflect the functional state of the cells of origin. Exosomes hold promise as research tools and as a therapeutic modality, but there is a need in the art for new and useful exosomes.

3. SUMMARY

In one aspect, provided herein are compositions comprising exosomes produced by and/or derived from placental cells, e.g., placenta-derived adherent cells. In certain embodiments, the exosomes provided herein are produced by placenta-derived adherent cells that have been cultured in vitro for, e.g., 1, 2, 3, 4, 5, 6 or more passages. In certain embodiments, the exosomes provided herein are collected from placenta-derived adherent cells that have been cultured in vitro for 1 passage. In other certain embodiment, the exosomes provided herein are collected from placenta-derived adherent cells that have been cultured in vitro for 2 passages. In other certain embodiment, the exosomes provided herein are collected from placenta-derived adherent cells that have been cultured in vitro for 3 passages. In other certain embodiment, the exosomes provided herein are collected from placenta-derived adherent cells that have been cultured in vitro for 4 passages. In other certain embodiment, the exosomes provided herein are collected from placenta-derived adherent cells that have been cultured in vitro for 5 passages. In a specific embodiment, the exosomes provided herein are collected from placenta-derived adherent cells that have been cultured in vitro for 6 passages. In other certain embodiment, the exosomes provided herein are collected from placenta-derived adherent cells that have been cultured in vitro for more than 6 passages. In certain embodiments, the exosomes provided herein are collected from placenta-derived adherent cells plated at passage 6, and collected (e.g., harvested) from culture supernatant at passage 7.

The placenta-derived adherent cell exosomes described herein comprise particular markers. Such markers can, for example, be useful in the identification of the exosomes and for distinguishing them from other exosomes, e.g., exosomes not derived from placenta-derived adherent cells. See Section 5.1.1. In certain embodiments, the placenta-derived adherent cell exosomes provided herein comprise one, two, three, four, or more of CD9, CD10, CD13, CD29, CD44, CD49b, CD49c, CD55, CD59, CD63, CD73, CD81, CD82, CD90, CD98, CD105, CD141, CD142, CD151, CD164, CD295, and/or CD200, i.e., such exosomes are one or more of $CD9^+$, $CD10^+$, $CD13^+$, $CD29^+$, $CD44^+$, $CD49b^+$, $CD49c^+$, $CD55^+$, $CD59^+$, $CD63^+$, $CD73^+$, $CD81^+$, $CD82^+$, $CD90^+$, $CD98^+$, $CD105^+$, $CD141^+$, $CD142^+$, $CD151^+$, $CD164^+$, $CD295^+$, and/or $CD200^+$, e.g., as determinable by flow cytometry, for example, by fluorescence-activated cell sorting (FACS). In addition, the placenta-derived adherent cell exosomes provided herein can be identified based on the absence of certain markers. In certain embodiments, the placenta-derived adherent cell exosomes provided herein lack one, two, three, four, or more of the following markers: CD3, CD11b, CD14, CD19, CD33, CD192, HLA-A, HLA-B, HLA-C, HLA-DR, CD11c and/or CD34, i.e., such exosomes are one or more of $CD3^-$, $CD11b^-$, $CD14^-$, $CD19^-$, $CD33^-$, $CD192^-$, $HLA-A^-$, $HLA-B^-$, $HLA-C^-$, $HLA-DR^-$, $CD11c^-$ and/or $CD34^-$, e.g., as determinable by flow cytometry, for example, by FACS. Determination of the presence or absence of such markers can be accomplished using methods known in the art, e.g., fluorescence-activated cell sorting (FACS).

In a specific embodiment, the placenta-derived adherent cell exosomes described herein are $CD55^+$ and $CD10^+$ as determined, e.g., by flow cytometry, for example, by FACS.

In specific embodiments, the placenta-derived adherent cell exosomes described herein are $CD10^+$ and $CD55^+$ (as determined by, e.g., FACS) and additionally contain CD82, CD142, CD49c, and CD90 at a level higher than chorionic villi mesenchymal stem cell exosomes or pre-adipocyte mesenchymal stem cell exosomes (e.g., the chorionic villi mesenchymal stem cells described in Salomon et al., 2013, PLOS ONE, 8:7, e68451).

In another embodiment, the placenta-derived adherent cell exosomes described herein do not contain detectable levels of CD4, CD5, CD6, CD7, CD8, CD16, CD24, CD25, CD26, CD27, CD32, CD35, CD37, CD39, CD45, CD46, CD54, CD56, CD61, CD74, CD86, CD88, CD91, CD99, CD103, CD108, CD112, CD117, CD119, CD120a, CD123, CD126, CD130, CD134, CD138, CD140a, CD140b, CD144, CD146, CD147, CD152, CD163, CD183, CD184, CD186, CD191, CD194, CD196, CDw198, CD202b, CD220, CD221, CD235a, CD252, CD266, CD271, CD273, CD274, CD318, CD326, CD333, CD334, HLA-DP, HLA-DQ, HLA-G, IgD, IgM, NG2, PDGF, and/or SSEA-3, as assessed, e.g., by flow cytometry, for example, by FACS. In certain embodiments, the placenta-derived adherent cell exosomes do not contain detectable levels of CD4. In certain embodiments, the placenta-derived adherent cell exosomes do not contain detectable levels of CD5. In certain embodiments, the placenta-derived adherent cell exosomes do not contain detectable levels of CD6. In certain embodiments, the placenta-derived adherent cell exosomes do not contain detectable levels of CD7. In certain embodiments, the placenta-derived adherent cell exosomes do not contain detectable levels of CD8. In certain embodiments, the placenta-derived adherent cell exosomes do not contain detectable levels of CD16. In certain embodiments, the placenta-derived adherent cell exosomes do not contain detectable levels of CD24. In certain embodiments, the placenta-derived adherent cell exosomes do not contain detectable levels of CD25. In certain embodiments, the placenta-derived adherent cell exosomes do not contain detectable levels of CD26. In certain embodiments, the placenta-derived adherent cell exosomes do not contain detectable levels of CD27. In certain embodiments, the placenta-derived adherent cell exosomes do not contain detectable levels of CD32. In certain embodiments, the placenta-derived adherent cell exosomes do not contain detectable levels of CD35. In certain embodiments, the placenta-derived adherent cell exosomes do not contain detectable levels of CD37. In certain embodiments, the placenta-derived adherent cell exosomes do not contain detectable levels of CD39. In certain embodiments, the placenta-derived adherent cell exosomes do not contain detectable levels of CD45. In certain embodiments, the placenta-derived adherent cell exosomes do not contain detectable levels of CD46. In certain embodiments, the placenta-derived adherent cell exosomes do not contain detectable levels of CD54. In certain embodiments, the placenta-derived adherent cell exosomes do not contain detectable levels of CD56. In certain embodiments, the placenta-derived adherent cell exosomes do not contain detectable levels of CD61. In certain embodiments, the placenta-derived adherent cell exosomes do not contain detectable levels of CD74. In certain embodiments, the placenta-derived adherent cell exosomes do not contain detectable levels of CD86. In certain embodiments, the placenta-derived adherent cell exosomes do not contain detectable levels of CD88. In certain embodiments, the placenta-derived adherent cell exosomes do not contain detectable levels of CD91. In certain embodiments, the placenta-derived adherent cell exosomes do not contain detectable levels of CD99. In certain embodiments, the placenta-derived adherent cell exosomes do not contain detectable levels of CD103. In certain embodiments, the placenta-derived adherent cell exosomes do not contain detectable levels of CD108. In certain embodiments, the placenta-derived adherent cell exosomes do not contain detectable levels of CD112. In certain embodiments, the placenta-derived adherent cell exosomes do not contain detectable levels of CD117. In certain embodiments, the placenta-derived adherent cell exosomes do not contain detectable levels of CD119, In certain embodiments, the placenta-derived adherent cell exosomes do not contain detectable levels of CD120a. In certain embodiments, the placenta-derived adherent cell exosomes do not contain detectable levels of CD123. In certain embodiments, the placenta-derived adherent cell exosomes do not contain detectable levels of CD126. In certain embodiments, the placenta-derived adherent cell exosomes do not contain detectable levels of CD130. In certain embodiments, the placenta-derived adherent cell exosomes do not contain detectable levels of CD134. In certain embodiments, the placenta-derived adherent cell exosomes do not contain detectable levels of CD138. In certain embodiments, the placenta-derived adherent cell exosomes do not contain detectable levels of CD140a. In certain embodiments, the placenta-derived adherent cell exosomes do not contain detectable levels of CD140b. In certain embodiments, the placenta-derived adherent cell exosomes do not contain detectable levels of CD144. In certain embodiments, the placenta-derived adherent cell exosomes do not contain detectable levels of CD146. In certain embodiments, the placenta-derived adherent cell exosomes do not contain detectable levels of CD147. In certain embodiments, the placenta-derived adherent cell exosomes do not contain detectable levels of CD152. In certain embodiments, the placenta-derived adherent cell exosomes do not contain detectable levels of CD163. In certain embodiments, the placenta-derived adherent cell exosomes do not contain detectable levels of CD183. In certain embodiments, the placenta-derived adherent cell exosomes do not contain detectable levels of CD184. In certain embodiments, the placenta-derived adherent cell exosomes do not contain detectable levels of CD186. In certain embodiments, the placenta-derived adherent cell exosomes do not contain detectable levels of CD191. In certain embodiments, the placenta-derived adherent cell exosomes do not contain detectable levels of CD194. In certain embodiments, the placenta-derived adherent cell exosomes do not contain detectable levels of CD196. In certain embodiments, the placenta-derived adherent cell exosomes do not contain detectable levels of CDw198. In certain embodiments, the placenta-derived adherent cell exosomes do not contain detectable levels of CD202b. In certain embodiments, the placenta-derived adherent cell exosomes do not contain detectable levels of CD220. In certain embodiments, the placenta-derived adherent cell exosomes do not contain detectable levels of CD221. In certain embodiments, the placenta-derived adherent cell exosomes do not contain detectable levels of CD235a. In certain embodiments, the placenta-derived adherent cell exosomes do not contain detectable levels of CD252. In certain embodiments, the placenta-derived adherent cell exosomes do not contain detectable levels of CD266. In certain embodiments, the placenta-derived adherent cell exosomes do not contain detectable levels of CD271. In certain embodiments, the placenta-derived adherent cell exosomes do not contain detectable levels of CD273. In certain embodiments, the placenta-derived adherent cell exosomes do not contain detectable levels of CD274. In certain embodiments, the placenta-derived adherent cell exosomes do not contain detectable levels of CD318. In certain embodiments, the placenta-derived adherent cell exosomes do not contain detectable levels of CD326. In certain embodiments, the placenta-derived adherent cell exosomes do not contain detectable levels of CD333. In certain embodiments, the placenta-derived adherent cell exosomes do not contain detectable levels of CD334. In certain embodiments, the placenta-derived adherent cell exosomes do not contain detectable levels of HLA-DP. In certain embodiments, the placenta-derived adherent cell exosomes do not contain detectable levels of HLA-DQ. In certain embodiments, the placenta-derived adherent cell exosomes do not contain detectable levels of HLA-G. In certain embodiments, the placenta-derived adherent cell exosomes do not contain detectable levels of IgD. In certain embodiments, the placenta-derived adherent cell exosomes do not contain detectable levels of IgM. In certain embodiments, the placenta-derived adherent cell exosomes do not contain detectable levels of NG2. In certain embodiments, the placenta-derived adherent cell exosomes do not contain detectable levels of PDGF. In certain embodiments, the placenta-derived adherent cell exosomes do not contain detectable levels of SSEA-3.

In certain embodiments, the placenta-derived adherent cell exosomes described herein are $CD82^+$ and contain a low level of CD141 (i.e., are CD141 (low)) as determined, e.g., by flow cytometry, for example, by FACS.

In certain embodiments, the placenta-derived adherent cell exosomes described herein comprise one or more markers at a level at least two-fold higher than the level of the marker as present in an equivalent number, or an equivalent mass, of exosomes derived from chorionic villi mesenchymal stem cells or pre-adipocyte mesenchymal stem cells as determinable by, e.g., FACS. In a specific embodiment, the placenta-derived adherent cell exosomes described herein comprise CD49c, CD142, CD90, and/or CD82 at a level at least two-fold higher than the level of each marker, respectively, as present in exosomes derived from chorionic villi mesenchymal stem cells or pre-adipocyte mesenchymal stem cells, e.g., as determinable by flow cytometry, for example, by FACS.

In a specific embodiment, the placenta-derived adherent cell exosomes described herein comprise a higher amount of CD49c, CD82, CD90, and/or CD142 than the amount of said marker(s) in a non placenta-derived adherent cell exosome. In a specific embodiment, the placenta-derived adherent cell exosomes described herein comprise a higher amount of CD49c, CD82, CD90, and/or CD142 than the amount of said marker(s) that is present in exosomes derived from chorionic villi mesenchymal stem cells (e.g., the chorionic villi mesenchymal stem cells described in Salomon et al., 2013, PLOS ONE, 8:7, e68451). In a specific embodiment, the placenta-derived adherent cell exosomes described herein comprise a higher amount of CD49c, CD73, CD82, CD90, and/or CD142 than the amount of said marker(s) that is present in exosomes derived from pre-adipocyte mesenchymal stem cells.

In certain embodiments, the placenta-derived adherent cell exosomes described herein comprise one or more markers at a level at least two-fold lower than the level of the marker as present in an equivalent number, or an equivalent mass, of exosomes derived from chorionic villi mesenchymal stem cells or pre-adipocyte mesenchymal stem cells as determinable by, e.g., FACS.

In a specific embodiment, the placenta-derived adherent cell exosomes described herein comprise a lower amount of CD164 than the amount of said marker(s) in a non placenta-derived adherent cell exosome. In a specific embodiment, the placenta-derived adherent cell exosomes described herein comprise a lower amount of CD164 than the amount of said marker(s) that is present in exosomes derived from pre-adipocyte mesenchymal stem cells or chorionic villi mesenchymal stem cells (e.g., the chorionic villi mesenchymal stem cells described in Salomon et al., 2013, PLOS ONE, 8:7, e68451).

In certain embodiments, the placenta-derived adherent cell exosomes described herein comprise one or more nucleic acids. In one embodiment, said nucleic acids are non-coding RNAs. In another embodiment, said non-coding RNAs are microRNAs (miRNAs). In a specific embodiment, the placenta-derived adherent cell exosomes described herein comprise one or more miRNAs selected from the group consisting of: miR-218-5p, miR-133b, miR-422a, miR-564, miR-16-5p, let-7a, miR-92, miR-142-3p, miR-451, miR-124-5p, miR-223-3p, miR-630, miR-296-5p, let-7b-3p and let-7d-3p. In a certain embodiment, the placenta-derived adherent cell exosomes comprise an miRNA that is miR-218-5p. In a certain embodiment, the placenta-derived adherent cell exosomes comprise an miRNA that is miR-133b. In a certain embodiment, the placenta-derived adherent cell exosomes comprise an miRNA that is miR-422a. In a certain embodiment, the placenta-derived adherent cell exosomes comprise an miRNA that is miR-564, miR-16-5p. In a certain embodiment, the placenta-derived adherent cell exosomes comprise an miRNA that is let-7a. In a certain embodiment, the placenta-derived adherent cell exosomes comprise an miRNA that is miR-92. In a certain embodiment, the placenta-derived adherent cell exosomes comprise an miRNA that is miR-142-3p. In a certain embodiment, the placenta-derived adherent cell exosomes comprise an miRNA that is miR-451. In a certain embodiment, the placenta-derived adherent cell exosomes comprise an miRNA that is miR-124-5p. In a certain embodiment, the placenta-derived adherent cell exosomes comprise an miRNA that is miR-223-3p. In a certain embodiment, the placenta-derived adherent cell exosomes comprise an miRNA that is miR-630. In a certain embodiment, the placenta-derived adherent cell exosomes comprise an miRNA that is miR-296-5p. In a certain embodiment, the placenta-derived adherent cell exosomes comprise an miRNA that is let-7b-3p. In a certain embodiment, the placenta-derived adherent cell exosomes comprise an miRNA that is let-7d-3p. In another specific embodiment, the placenta-derived adherent cell exosomes comprise one or more of miRNAs miR-218-5p, miR-133b, miR-422a, and/or miR-564. In another specific embodiment, the placenta-derived adherent cell exosomes comprise one or more of miRNAs miR-133b, miR-422a, miR-16-5p, miR-92, miR-142-3p, miR-451, miR-223-3p, miR-296-5p, and/or miR-Let-7d*/Let-7d-3p. In other specific embodiments, the placenta-derived adherent cell exosomes comprise one or more of miRNAs miR-591, miR-218-5p, miR-133b, miR-422a, and/or miR-564. In another specific embodiment, said one or more miRNAs are present at a level at least two-fold higher than the level of the corresponding miRNA as present in chorionic villi mesenchymal stem cells. In other specific embodiments, the placenta-derived adherent cell exosomes, when subjected to RT-PCR with respect to a specific miRNA and compared to a control RNA (e.g., RNU44), are contained at a level 1.1, 2, 5, 10, 100, 500, 600, 700, 800, 900, 1000, 1100 or 1200 times higher than the same miRNA in chorionic villi mesenchymal stem cell exosomes, or between 1.1 and 2, 2 and 5, 2 and 10, 5 and 10, 10 and 100, 100 and 500, 500 and 600, 600 and 700, 700 and 800, 800 and 900, 900 and 1000, 1000 and 1100, or 1100 and 1200 times higher than the same miRNA in chorionic villi mesenchymal stem cell exosomes. In a certain embodiment, the placenta-derived adherent cell exosomes comprise at least one marker at a level at least 1.1 times higher than exosomes derived from mesenchymal stem cells. In a certain embodiment, the placenta-derived adherent cell exosomes comprise at least one marker at a level at least 2 times higher than exosomes derived from mesenchymal stem cells. In a certain embodiment, the placenta-derived adherent cell exosomes comprise at least one marker at a level at least 5 times higher than exosomes derived from mesenchymal stem cells. In a certain embodiment, the placenta-derived adherent cell exosomes comprise at least one marker at a level at least 10 times higher than exosomes derived from mesenchymal stem cells. In a certain embodiment, the placenta-derived adherent cell exosomes comprise at least one marker at a level at least 100 times higher than exosomes derived from mesenchymal stem cells. In a certain embodiment, the placenta-derived adherent cell exosomes comprise at least one marker at a level at least 500 times higher than exosomes derived from mesenchymal stem cells. In a certain embodiment, the placenta-derived adherent cell exosomes comprise at least one marker at a level at least 600 times higher than exosomes derived from mesenchymal stem cells. In a certain embodiment, the placenta-derived adherent cell exosomes comprise at least one marker at a level at least 700 times higher than exosomes derived from mesenchymal stem cells. In a certain embodiment, the placenta-derived adherent cell exosomes comprise at least one marker at a level at least 800 times higher than exosomes derived from mesenchymal stem cells. In a certain embodiment, the placenta-derived adherent cell exosomes comprise at least one marker at a level at least 900 times higher than exosomes derived from mesenchymal stem cells. In a certain embodiment, the placenta-derived adherent cell exosomes comprise at least one marker at a level at least 1000 times higher than exosomes derived from mesenchymal stem cells. In a certain embodiment, the placenta-derived adherent cell exosomes comprise at least one marker at a level at least 1100 times higher than exosomes derived from mesenchymal stem cells. In a certain embodiment, the placenta-derived adherent cell exosomes comprise at least one marker at a level at least 1200 times higher than exosomes derived from mesenchymal stem cells.

In one embodiment, the placenta-derived adherent cell exosomes described herein contain one or more angiogenic proteins selected from the group of Endoglin, Leptin, Angiopoietin-2, G-CSF, Follistatin, FGF-2, HGF, VEGF-A, TF-8 and/or EGF.

Further provided herein are populations of exosomes comprising the placenta-derived adherent cell exosomes described herein. In a specific embodiment, the populations of exosomes provided herein are pure or substantially pure with respect to their content of placenta-derived adherent cell exosomes, e.g., the populations of exosomes comprise about 90%, 95%, 98%, 99%, or 100% placenta-derived adherent cell exosomes. In another specific embodiment, the populations of exosomes provided herein comprise the placenta-derived adherent cell exosomes provided herein and one or more other types of exosomes, e.g., exosomes derived from a cell other than a placenta-derived adherent cell.

In a specific embodiment, provided herein is a population of placenta-derived adherent cell exosomes, wherein about 75%, 80%, 85%, 90%, 91%, 92%, 93%, 94%, 95%, 96%, 97%, 98%, 99%, or 100% of the exosomes in said population are one or more of $CD9^+$, $CD10^+$, $CD13^+$, $CD29^+$, $CD44^+$, $CD49b^+$, $CD49c^+$, $CD55^+$, $CD59^+$, $CD63^+$, $CD73^+$, $CD81^+$, $CD82^+$, $CD90^+$, $CD98^+$, $CD105^+$, $CD141^+$, $CD142^+$, $CD151^+$, $CD164^+$, $CD295^+$, and/or $CD200^+$, as determinable by, e.g., FACS.

The placenta-derived adherent cell exosomes described herein may be isolated by any method known in the art suitable for the isolation of exosomes. See Section 5.2. For example, the placenta-derived adherent cell exosomes described herein can be isolated by centrifugation (e.g., density-dependent ultracentrifugation), polymer co-precipitation (e.g., ExoQuick-TC exosome precipitation reagent by System Biosciences), filtration (e.g., high-performance liquid chromatography and gel-filtration chromatography), antibody capture, or fluorescence-activated cell sorting (FACS). In certain embodiments, the isolation and purification of the placenta-derived adherent cell exosomes provided herein results in a substantially pure placenta-derived adherent cell exosome population, e.g., a placenta-derived adherent cell exosome population that is at least 99%, 98%, 97%, 96%, 95%, 94%, 93%, 92%, 91%, or 90% pure, e.g., as determined by the presence of one or more markers associated with the placenta-derived adherent cell exosomes provided herein (e.g., surface markers and/or miRNAs). In a certain embodiment, the placenta-derived adherent cell exosome population that is at least 99% pure. In a certain embodiment, the placenta-derived adherent cell exosome population that is at least 98% pure. In a certain embodiment, the placenta-derived adherent cell exosome population that is at least 97% pure. In a certain embodiment, the placenta-derived adherent cell exosome population that is at least 96% pure. In a certain embodiment, the placenta-derived adherent cell exosome population that is at least 95% pure. In a certain embodiment, the placenta-derived adherent cell exosome population that is at least 94% pure. In a certain embodiment, the placenta-derived adherent cell exosome population that is at least 93% pure. In a certain embodiment, the placenta-derived adherent cell exosome population that is at least 92% pure. In a certain embodiment, the placenta-derived adherent cell exosome population that is at least 91% pure. In a certain embodiment, the placenta-derived adherent cell exosome population that is at least 90% pure.

Also provided herein are compositions comprising placenta-derived adherent cell exosomes. Such compositions generally do not comprise placental cells from which the placenta-derived adherent cell exosomes have been derived. Moreover, such compositions generally do not comprise cell culture supernatant from the cell culture from which the placenta-derived adherent cell exosomes have been derived.

In certain embodiments, purified placenta-derived adherent cell exosomes are formulated into pharmaceutical compositions suitable for administration to a subject in need thereof. In certain embodiments, said subject is a human. The placenta-derived adherent cell exosome-containing pharmaceutical compositions provided herein can be formulated to be administered locally, systemically subcutaneously, parenterally, intravenously, intramuscularly, topically, orally, intradermally, transdermally, or intranasally to a subject in need thereof. In a certain embodiment, the placenta-derived adherent cell exosome-containing pharmaceutical compositions provided herein are formulated for local administration. In a certain embodiment, the placenta-derived adherent cell exosome-containing pharmaceutical compositions provided herein are formulated for systemic subcutaneous administration. In a certain embodiment, the placenta-derived adherent cell exosome-containing pharmaceutical compositions provided herein are formulated for parenteral administration. In a certain embodiment, the placenta-derived adherent cell exosome-containing pharmaceutical compositions provided herein are formulated for intramuscular administration. In a certain embodiment, the placenta-derived adherent cell exosome-containing pharmaceutical compositions provided herein are formulated for topical administration. In a certain embodiment, the placenta-derived adherent cell exosome-containing pharmaceutical compositions provided herein are formulated for oral administration. In a certain embodiment, the placenta-derived adherent cell exosome-containing pharmaceutical compositions provided herein are formulated for intradermal administration. In a certain embodiment, the placenta-derived adherent cell exosome-containing pharmaceutical compositions provided herein are formulated for transdermal administration. In a certain embodiment, the placenta-derived adherent cell exosome-containing pharmaceutical compositions provided herein are formulated for intranasal administration. In a specific embodiment, the placenta-derived adherent cell exosome-containing pharmaceutical compositions provided herein are formulated for intravenous administration.

In a specific embodiment, the placenta-derived adherent cells from which the exosomes provided herein are derived are $CD34^-$, $CD10^+$, $CD105^+$ and $CD200^+$. In another embodiment, the placenta-derived adherent cells from which the exosomes provided herein are derived express one or more genes at a level at least two-fold higher than bone marrow-derived mesenchymal stem cells, wherein said one or more genes are one or more of: ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FIJ10781, GATA6, GPR126, GPRC5B, HLA-G, ICAM1, IER3, IGFBP7, IL1A, IE6, IE18, KRT18, KRT8, LIPG, LRAP, MATN2, MEST, NFE2F3, NUAK1, PCDH7, PDLIM3, PJP2, RTN1, SERPINB9, ST3GAL6, ST6GALNAC5, SLC12A8, TCF21, TGFB2, VTN, and/or ZC3H12A. In another embodiment, the placenta-derived adherent cells from which the exosomes provided herein are derived express one or more genes at a level at least two-fold higher than bone marrow-derived mesenchymal stem cells, wherein said one or more genes are one or more of LOVL2, ST3GAL6, ST6GALNAC5, and/or SLC12A8. In another embodiment, the placenta-derived adherent cells from which the exosomes provided herein are derived express one or more genes at a level at least two-fold higher than bone marrow-derived mesenchymal stem cells, wherein said one or more genes are one or more of CPA4, TCF21, VTN, B4GALT6, FLJ10781, and/or NUAK1.

In certain embodiments, the placenta-derived adherent cell exosomes described herein are isolated from placenta-derived adherent cell cultures that contain serum (e.g., fetal bovine serum). In certain embodiments, the placenta-derived adherent cell exosomes described herein are isolated from placenta-derived adherent cell cultures that lack serum.

In certain embodiments, the placenta-derived adherent cells from which the placenta-derived adherent cell exosomes described herein are isolated have been passaged at least 1, 2, 3, 4, 5, 6, 7, 8, 9, 10, 12, 14, 16, 18, or 20 times, or more, before said exosomes are isolated. In a certain embodiment, the placenta-derived adherent cells have been passaged at least 1 time. In a certain embodiment, the placenta-derived adherent cells have been passaged at least 2 times. In a certain embodiment, the placenta-derived adherent cells have been passaged at least 3 times. In a certain embodiment, the placenta-derived adherent cells have been passaged at least 4 times. In a certain embodiment, the placenta-derived adherent cells have been passaged at least 5 times. In a certain embodiment, the placenta-derived adherent cells have been passaged at least 6 times. In a certain embodiment, the placenta-derived adherent cells have been passaged at least 7 times. In a certain embodiment, the placenta-derived adherent cells have been passaged at least 8 times. In a certain embodiment, the placenta-derived adherent cells have been passaged at least 9 times. In a certain embodiment, the placenta-derived adherent cells have been passaged at least 10 times. In a certain embodiment, the placenta-derived adherent cells have been passaged at least 12 times. In a certain embodiment, the placenta-derived adherent cells have been passaged at least 14 times. In a certain embodiment, the placenta-derived adherent cells have been passaged at least 16 times. In a certain embodiment, the placenta-derived adherent cells have been passaged at least 18 times. In a certain embodiment, the placenta-derived adherent cells have been passaged at least 20 times. In certain embodiments, the placenta-derived adherent cells from which the placenta-derived adherent cell exosomes described herein are isolated have been expanded for 1, 2, 3, 4, 5, 6, 7, 8, 9, 10, 12, 14, 16, 18, 20, 22, 24, 26, 28, 30, 32, 34, 36, 38 or 40 population doublings, or more, before said exosomes are isolated. In a certain embodiment, the placenta-derived adherent cells have been expanded for 1 population doubling. In a certain embodiment, the placenta-derived adherent cells have been expanded for 2 population doublings. In a certain embodiment, the placenta-derived adherent cells have been expanded for 3 population doublings. In a certain embodiment, the placenta-derived adherent cells have been expanded for 4 population doublings. In a certain embodiment, the placenta-derived adherent cells have been expanded for 5 population doublings. In a certain embodiment, the placenta-derived adherent cells have been expanded for 6 population doublings. In a certain embodiment, the placenta-derived adherent cells have been expanded for 7 population doublings. In a certain embodiment, the placenta-derived adherent cells have been expanded for 8 population doublings. In a certain embodiment, the placenta-derived adherent cells have been expanded for 9 population doublings. In a certain embodiment, the placenta-derived adherent cells have been expanded for 10 population doublings. In a certain embodiment, the placenta-derived adherent cells have been expanded for 12 population doublings. In a certain embodiment, the placenta-derived adherent cells have been expanded for 14 population doublings. In a certain embodiment, the placenta-derived adherent cells have been expanded for 16 population doublings. In a certain embodiment, the placenta-derived adherent cells have been expanded for 18 population doublings. In a certain embodiment, the placenta-derived adherent cells have been expanded for 20 population doublings. In a certain embodiment, the placenta-derived adherent cells have been expanded for 22 population doublings. In a certain embodiment, the placenta-derived adherent cells have been expanded for 24 population doublings. In a certain embodiment, the placenta-derived adherent cells have been expanded for 26 population doublings. In a certain embodiment, the placenta-derived adherent cells have been expanded for 28 population doublings. In a certain embodiment, the placenta-derived adherent cells have been expanded for 30 population doublings. In a certain embodiment, the placenta-derived adherent cells have been expanded for 32 population doublings. In a certain embodiment, the placenta-derived adherent cells have been expanded for 34 population doublings. In a certain embodiment, the placenta-derived adherent cells have been expanded for 36 population doublings. In a certain embodiment, the placenta-derived adherent cells have been expanded for 38 population doublings. In a certain embodiment, the placenta-derived adherent cells have been expanded for 40 population doublings.

In certain embodiments, the placenta-derived adherent cells from which the placenta-derived adherent cell exosomes described herein are isolated are at least 80%, at least 90%, at least 95%, at least 99%, or 100% fetal in origin. In a certain embodiment, the placenta-derived adherent cells are at least 80% fetal in origin. In a certain embodiment, the placenta-derived adherent cells are at least 90% fetal in origin. In a certain embodiment, the placenta-derived adherent cells are at least 95% fetal in origin. In a certain embodiment, the placenta-derived adherent cells are at least 99% fetal in origin. In a certain embodiment, the placenta-derived adherent cells are at least 100% fetal in origin.

In another aspect, provided herein are uses of the placenta-derived adherent cell exosomes and/or pharmaceutical compositions comprising placenta-derived adherent cell exosomes described herein. See Section 5.4.

In a specific embodiment, the placenta-derived adherent cell exosomes and/or pharmaceutical compositions comprising placenta-derived adherent cell exosomes described herein are used to treat and/or prevent diseases and/or conditions in a subject in need thereof. In a specific embodiment, the placenta-derived adherent cell exosomes and/or pharmaceutical compositions comprising placenta-derived adherent cell exosomes described herein are used to promote angiogenesis and/or vascularization in a subject in need thereof. In another specific embodiment, the placenta-derived adherent cell exosomes and/or pharmaceutical compositions comprising placenta-derived adherent cell exosomes described herein are used to modulate immune activity (e.g., increase an immune response or decrease an immune response) in a subject in need thereof. In another specific embodiment, the placenta-derived adherent cell exosomes and/or pharmaceutical compositions comprising placenta-derived adherent cell exosomes described herein are used to repair tissue damage, e.g., tissue damage caused by an acute or chronic injury, in a subject in need thereof.

In another specific embodiment, the derived adherent cell exosomes and/or pharmaceutical compositions comprising placenta-derived adherent cell exosomes described herein are for use in a method for treating and/or preventing diseases and/or conditions in a subject in need thereof. In another embodiment, the pharmaceutical compositions comprising placenta-derived adherent cell exosomes described herein are for use in a method for treating diseases and/or conditions in a subject in need thereof. In another embodiment, the pharmaceutical compositions comprising placenta-derived adherent cell exosomes described herein are for use in a method for preventing diseases and/or conditions in a subject in need thereof. In a specific embodiment, the pharmaceutical compositions comprising placenta-derived adherent cell exosomes described herein are for use in a method for promoting angiogenesis and/or vascularization in a subject in need thereof. In another specific embodiment, the pharmaceutical compositions comprising placenta-derived adherent cell exosomes described herein are for use in a method for modulating immune activity (e.g., increase an immune response or decrease an immune response) in a subject in need thereof. In another specific embodiment, the pharmaceutical compositions comprising placenta-derived adherent cell exosomes described herein are for use in a method for repairing tissue damage, e.g., tissue damage caused by an acute or chronic injury, in a subject in need thereof.

In another specific embodiment, the placenta-derived adherent cell exosomes and/or pharmaceutical compositions comprising placenta-derived adherent cell exosomes described herein are used as cytoprotective agents. In another aspect, the placenta-derived adherent cell exosomes and/or pharmaceutical compositions comprising placenta-derived adherent cell exosomes described herein are provided in the form of a kit suitable for pharmaceutical use. See Section 5.5.

In another embodiment, provided herein are methods of loading placenta-derived adherent cell exosomes with exogenous agents, for example, pharmaceutical agents. In one embodiment, such a method comprises incubating a placenta-derived adherent cell exosome and an exogenous agent, e.g., pharmaceutical agent, for example incubating at room temperature, with or without saponin permeabilization, freeze/thaw cycles, sonication, or extrusion. In certain embodiments, the exogenous agent, e.g., pharmaceutical agent, is loaded into the placenta-derived adherent cell exosome by incubation at room temperature. In specific embodiments, incubation, e.g., incubation at room temperature, is performed without saponin permeabilization of the exosome. In specific embodiments, incubation, e.g., incubation at room temperature, is performed with saponin permeabilization of the placenta-derived adherent cell exosome. In certain embodiments, the exogenous agent, e.g., pharmaceutical agent, is loaded into the exosome by freeze/thaw cycles, for example, 1, 2, 3, 4, 5, or more freeze/thaw cycles. In certain embodiments, the exogenous agent, e.g., pharmaceutical agent, is loaded into the placenta-derived adherent cell exosome by sonication. In certain embodiments, the exogenous agent, e.g., pharmaceutical agent, is loaded into the placenta-derived adherent cell exosome by extrusion. In certain embodiments, the exogenous agent is loaded into the placenta-derived adherent cell exosome by electroporation. In specific embodiments, methods of loading placenta-derived adherent cell exosomes with exogenous agents, for example, pharmaceutical agents, comprise any combination of the above.

In certain embodiments, the exogenous agent, e.g., pharmaceutical agent, loaded into the placenta-derived adherent cell exosomes described herein comprises a polypeptide. In specific embodiments, the exogenous agent, e.g., pharmaceutical agent is a binding agent, for example, an antibody, such as, e.g., a human, humanized, or chimeric antibody, or antigen-binding fragment thereof. In particular embodiments, the antibody is a monospecific, bispecific or multispecific antibody, or antigen-binding fragment thereof. In yet other particular embodiments, the antibody or antigen binding fragment thereof is a single-chain antibody or a Fab fragment. In specific embodiments, the antibody or antigen-binding fragment thereof would not internalize into a target cell, e.g., a cell other than the cell type from which the exosomes were obtained, without the aid of the placenta-derived adherent cell exosome.

In certain embodiments, the exogenous agent, e.g., pharmaceutical agent, loaded into the placenta-derived adherent cell exosomes described herein comprises one or more nucleic acids. In specific embodiments, the one or more nucleic acids comprise a small interfering RNA (siRNA) or an miRNA.

In certain embodiments, the exogenous agent, e.g., pharmaceutical agent, loaded into the placenta-derived adherent cell exosomes described herein comprises one or more gene-modifying components. In specific embodiments, the one or more gene-modifying components comprise a CRISPR-Cas system. In more specific embodiments, the CRISPR-Cas system comprises a guide RNA. In more specific embodiments, the CRISPR-Cas system comprises an endonuclease. In more specific embodiments, the CRISPR-Cas system comprises a guide RNA and an endonuclease. In more specific embodiments, the CRISPR-Cas system comprises Cas9. In more specific embodiments, the CRISPR-Cas system comprises Cpf1. In specific embodiments, the one or more gene-modifying components comprise a zinc finger nuclease. In specific embodiments, the one or more gene-modifying components comprise a transcription activator-like effector nuclease (TALEN) system.

In another embodiment, provided herein are methods of delivering an exogenous agent, e.g., a pharmaceutical agent, to a target cell, wherein the exogenous agent is loaded into a placenta-derived adherent cell exosome. In certain embodiments, the target cell is a cell other than the cell type from which the exosome was obtained. In certain embodiments, the exogenous agent, e.g., pharmaceutical agent, loaded into the placenta-derived adherent cell exosomes described herein comprises a polypeptide. In specific embodiments, the exogenous agent, e.g., pharmaceutical agent is a binding agent, for example, an antibody, such as, e.g., a human, humanized, or chimeric antibody, or antigen-binding fragment thereof. In particular embodiments, the antibody is a monospecific, bispecific or multispecific antibody, or antigen-binding fragment thereof. In yet other particular embodiments, the antibody or antigen binding fragment thereof is a single-chain antibody or a Fab fragment. In specific embodiments, the antibody or antigen-binding fragment thereof would not internalize into a target cell, e.g., a cell other than the cell type from which the exosomes were obtained, without the aid of the placenta-derived adherent cell exosome. In certain embodiments, the exogenous agent, e.g., pharmaceutical agent, loaded into the placenta-derived adherent cell exosomes described herein comprises one or more nucleic acids. In specific embodiments, the one or more nucleic acids comprise a siRNA or an miRNA. In certain embodiments, the exogenous agent, e.g., pharmaceutical agent, loaded into the placenta-derived adherent cell exosomes described herein comprises one or more gene-modifying components. In specific embodiments, the one or more gene-modifying components comprise a CRISPR-Cas system. In more specific embodiments, the CRISPR-Cas system comprises a guide RNA. In more specific embodiments, the CRISPR-Cas system comprises an endonuclease. In more specific embodiments, the CRISPR-Cas system comprises a guide RNA and an endonuclease. In more specific embodiments, the CRISPR-Cas system comprises Cas9. In more specific embodiments, the CRISPR-Cas system comprises Cpf1. In specific embodiments, the one or more gene-modifying components comprise a zinc finger nuclease. In specific embodiments, the one or more gene-modifying components comprise a transcription activator-like effector nuclease (TALEN) system.

In another embodiment, provided herein are methods of administering exosomes comprising exogenous agents, for example, pharmaceutical agents, to a subject, e.g., a human. In certain embodiments, the exogenous agent, e.g., pharmaceutical agent, comprises a polypeptide. In specific embodiments, the exogenous agent, e.g., pharmaceutical agent, is a binding agent, for example, an antibody, such as, e.g., a human, humanized, or chimeric antibody, or antigen-binding fragment thereof. In particular embodiments, the antibody is a monospecific, bispecific or multispecific antibody, or antigen-binding fragment thereof. In yet other particular embodiments, the antibody or antigen binding fragment thereof is a single-chain antibody or a Fab fragment. In specific embodiments, the antibody or antigen-binding fragment thereof would not internalize into a target cell without the aid of the exosome. In certain embodiments, the exogenous agent, e.g., pharmaceutical agent, loaded into the placenta-derived adherent cell exosomes described herein comprises one or more nucleic acids. In specific embodiments, the one or more nucleic acids comprise a siRNA or an miRNA. In certain embodiments, the exogenous agent, e.g., pharmaceutical agent, loaded into the placenta-derived adherent cell exosomes described herein comprises one or more gene-modifying components. In specific embodiments, the one or more gene-modifying components comprise a CRISPR-Cas system. In more specific embodiments, the CRISPR-Cas system comprises a guide RNA. In more specific embodiments, the CRISPR-Cas system comprises an endonuclease. In more specific embodiments, the CRISPR-Cas system comprises a guide RNA and an endonuclease. In more specific embodiments, the CRISPR-Cas system comprises Cas9. In more specific embodiments, the CRISPR-Cas system comprises Cpf1. In specific embodiments, the one or more gene-modifying components comprise a zinc finger nuclease. In specific embodiments, the one or more gene-modifying components comprise a transcription activator-like effector nuclease (TALEN) system.

In another embodiment, provided herein are compositions comprising placenta-derived adherent cell exosomes loaded with one or more exogenous agents, for example, pharmaceutical agents. In certain embodiments, the exogenous agent, e.g., pharmaceutical agent, incorporated into the placenta-derived adherent cell exosomes described herein comprises a polypeptide. In specific embodiments, the exogenous agent, e.g., pharmaceutical agent, is a binding agent, for example, an antibody, such as, e.g., a human, humanized, or chimeric antibody, or antigen-binding fragment thereof. In particular embodiments, the antibody is a monospecific, bispecific or multispecific antibody, or antigen-binding fragment thereof. In yet other particular embodiments, the antibody or antigen binding fragment thereof is a single-chain antibody or a Fab fragment. In specific embodiments, the antibody or antigen-binding fragment thereof would not internalize into a target cell without the aid of the exosome. In certain embodiments, the exogenous agent, e.g., pharmaceutical agent, loaded into the placenta-derived adherent cell exosomes described herein comprises one or more nucleic acids. In specific embodiments, the one or more nucleic acids comprise a siRNA or an miRNA. In certain embodiments, the exogenous agent, e.g., pharmaceutical agent, loaded into the placenta-derived adherent cell exosomes described herein comprises one or more gene-modifying components. In specific embodiments, the one or more gene-modifying components comprise a CRISPR-Cas system. In more specific embodiments, the CRISPR-Cas system comprises a guide RNA. In more specific embodiments, the CRISPR-Cas system comprises an endonuclease. In more specific embodiments, the CRISPR-Cas system comprises a guide RNA and an endonuclease. In more specific embodiments, the CRISPR-Cas system comprises Cas9. In more specific embodiments, the CRISPR-Cas system comprises Cpf1. In specific embodiments, the one or more gene-modifying components comprise a zinc finger nuclease. In specific embodiments, the one or more gene-modifying components comprise a transcription activator-like effector nuclease (TALEN) system.

4. BRIEF DESCRIPTION OF THE DRAWINGS

FIG. 1 shows the results of an exosome antibody array demonstrating the existence of placenta-derived adherent cell exosomes. Top panel: positive control from chorionic villi mesenchymal stem cells; bottom panel placenta-derived adherent cell exosomes.

FIG. 2A-2B: FIG. 2A is an electron micrograph of placenta-derived adherent cell exosomes, with arrows indicating cup-shaped structures that are a common distinguishing feature of exosomes. FIG. 2B shows the size distribution of placenta-derived adherent cell exosomes as determined by nanoparticle tracking assay.

FIGS. 3A-3D show the elution profiles of known molecules (FIG. 3A) as compared to exosomes from either chorionic villi mesenchymal stem cells (FIG. 3B) or the non-chorionic placenta-derived adherent cells described herein isolated under culture conditions containing or lacking serum (FIGS. 3C and 3D).

FIGS. 4A-4C: FIG. 4A shows levels of various microRNAs contained in exosomes isolated from chorionic villi mesenchymal stem cells or from the exosomes described herein. FIGS. 4B-4C show levels of various angiogenic proteins contained on or within the exosomes described herein.

Figure 7A:
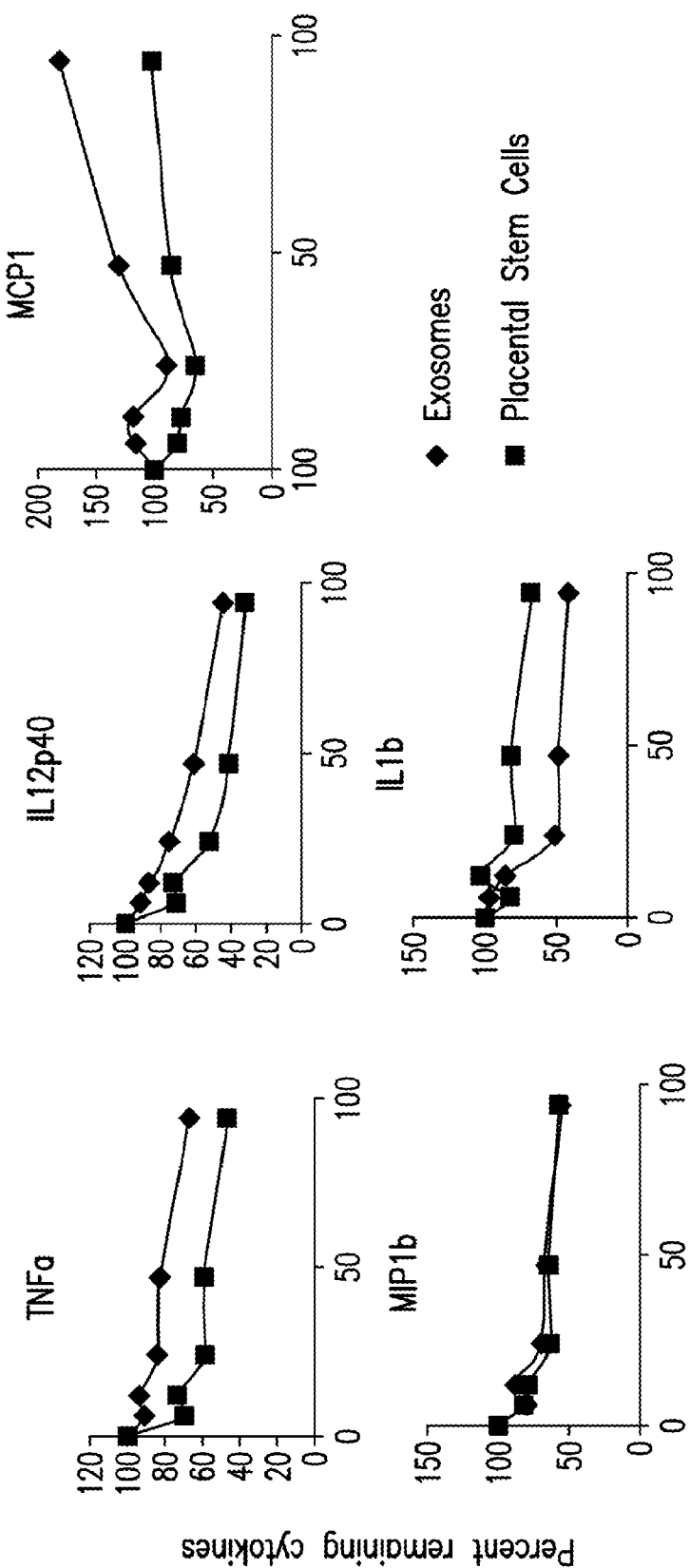
Figure 7B:
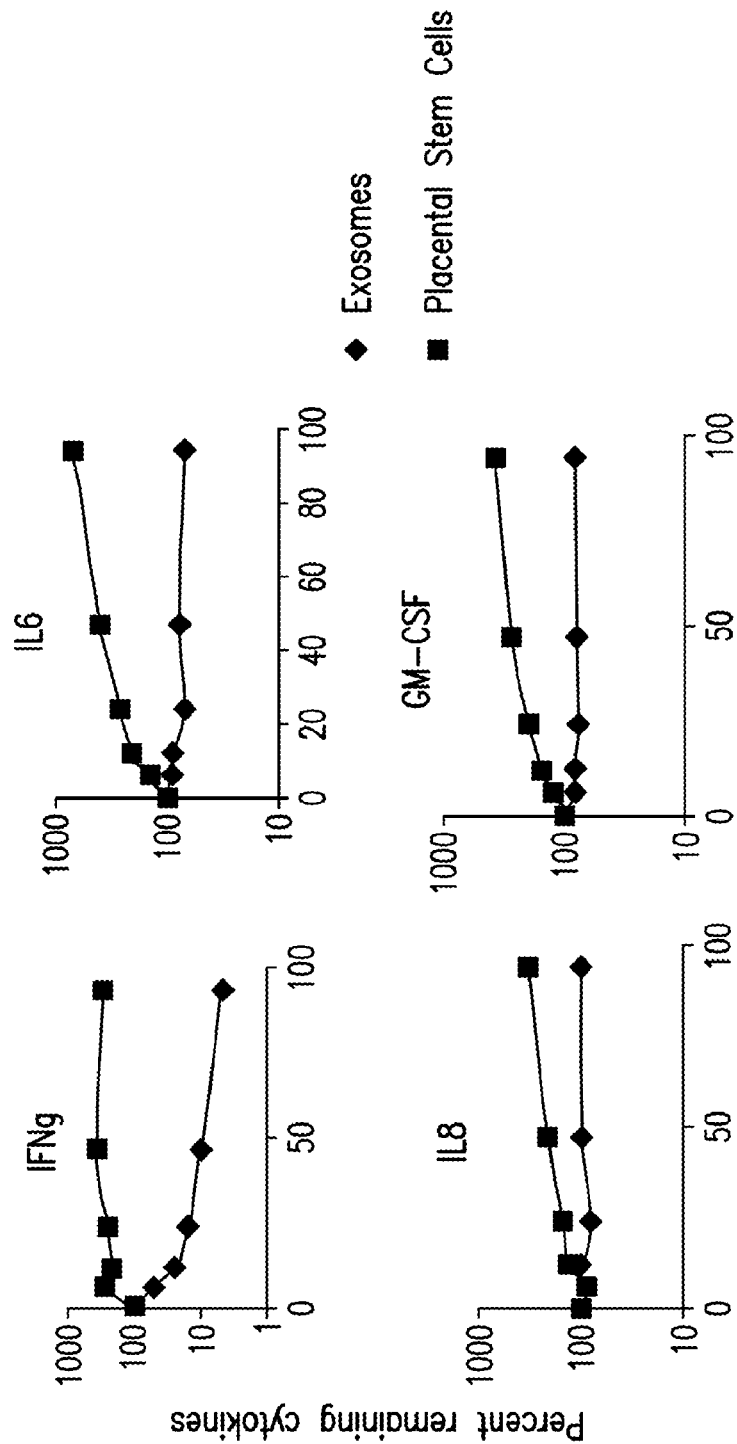

FIGS. 7A-B show the levels of various cytokines and chemokines produced in vitro by LPS-stimulated human blood after incubation with placenta-derived adherent cells or placenta-derived adherent cell exosomes.

Figure 8A:
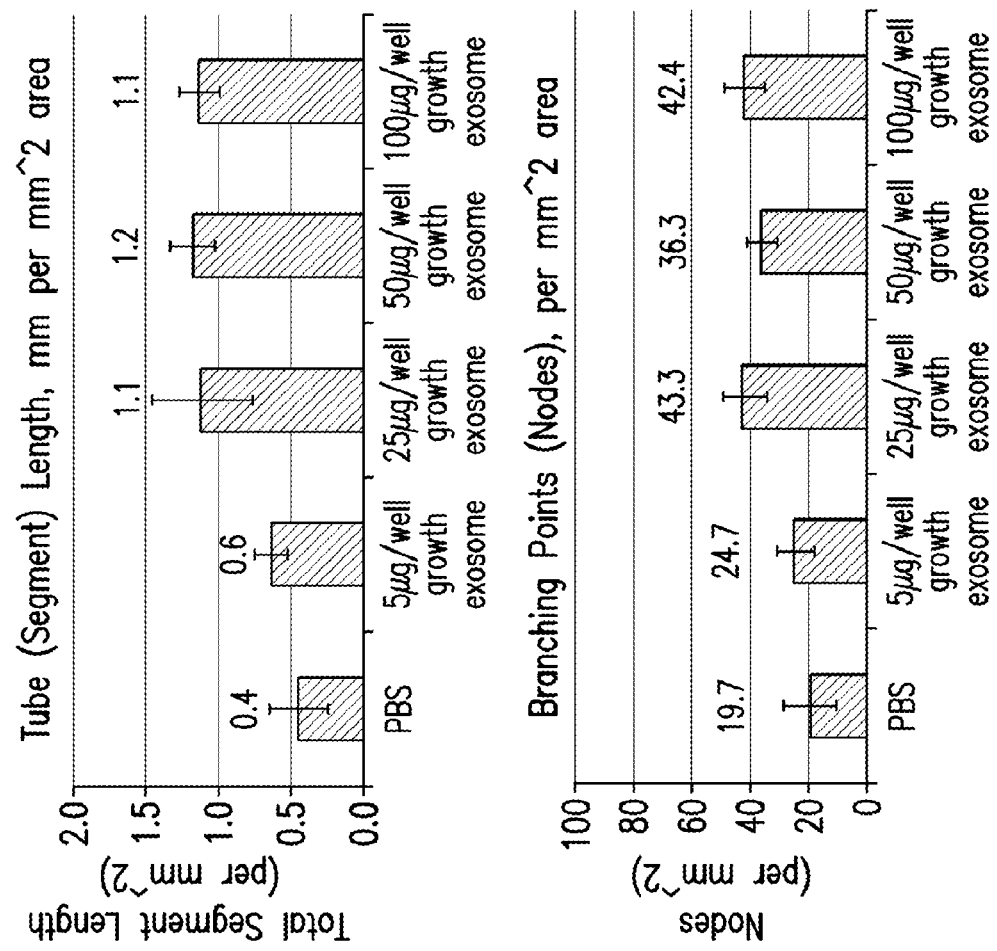
Figure 8B:
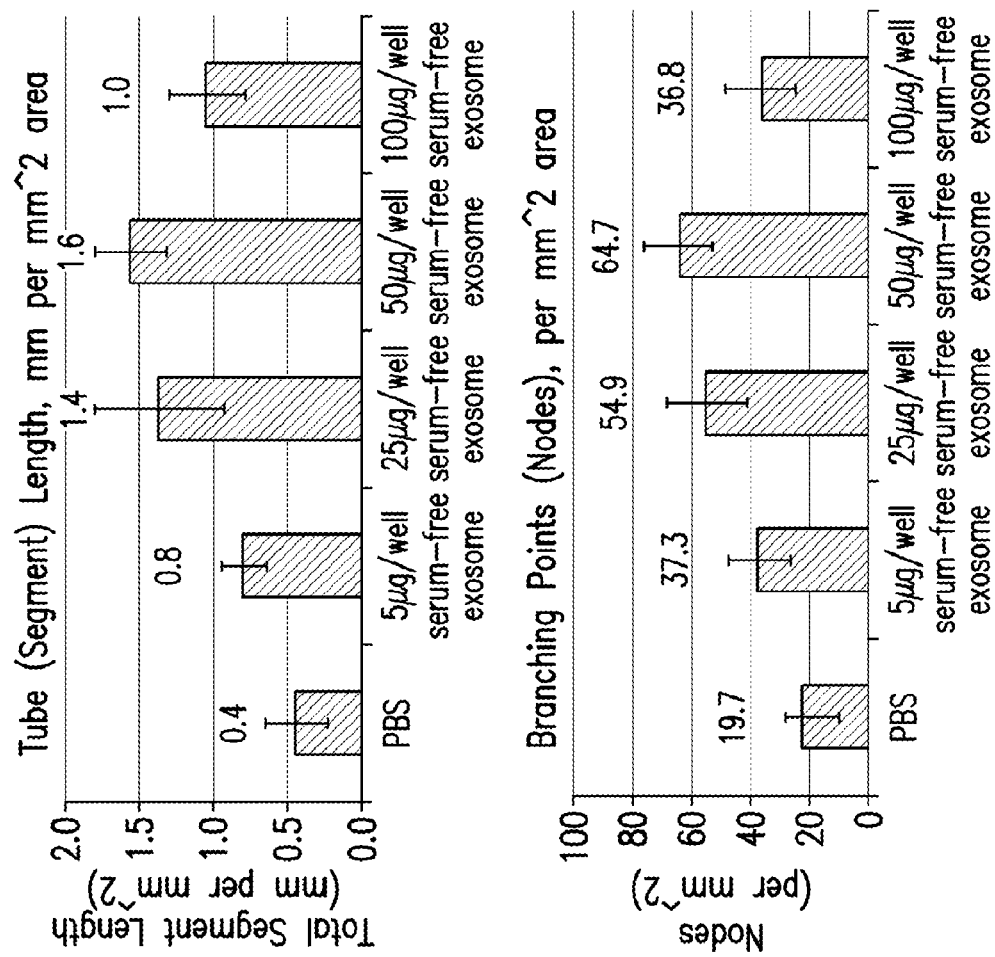
Figure 8D:
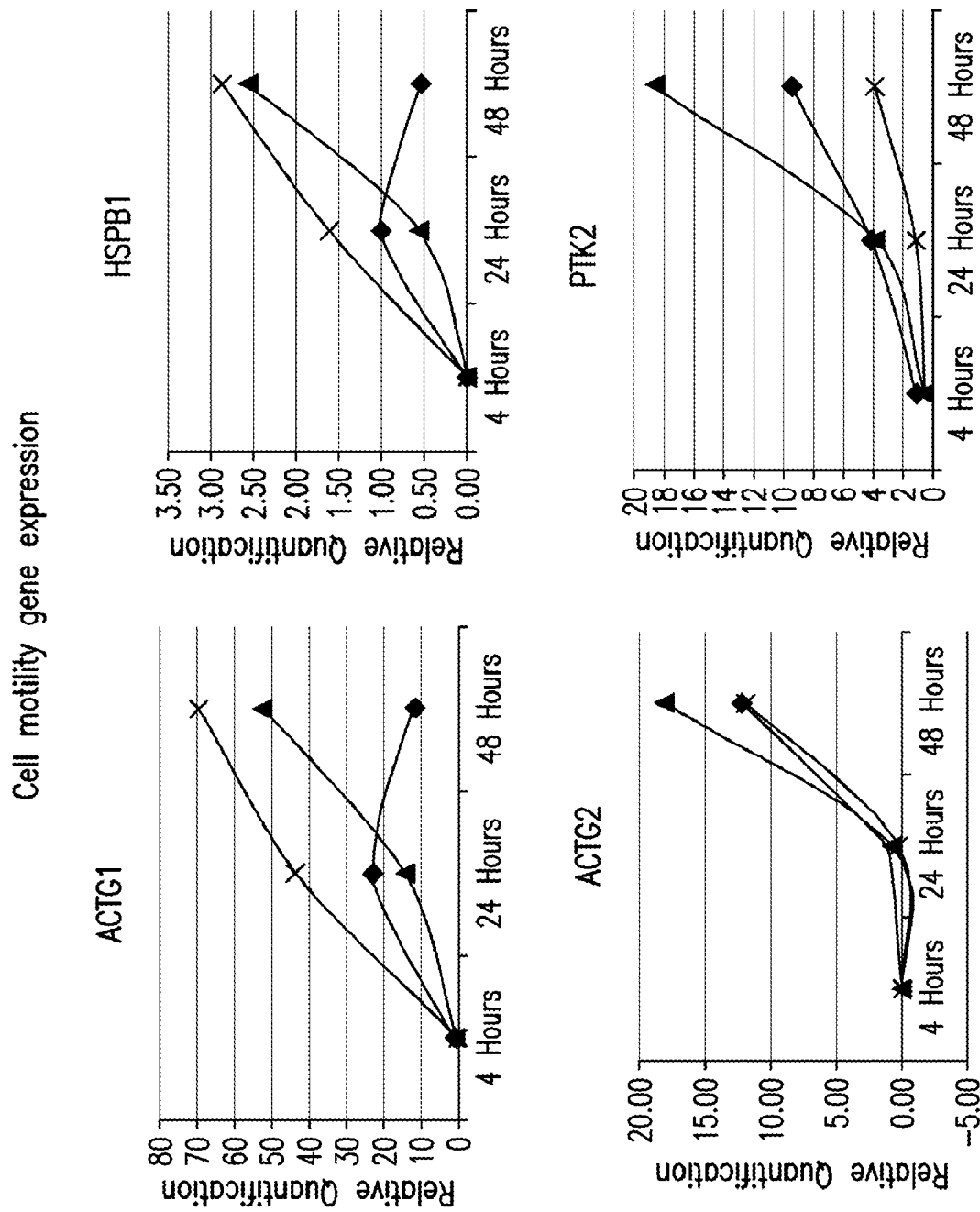
Figure 8E:
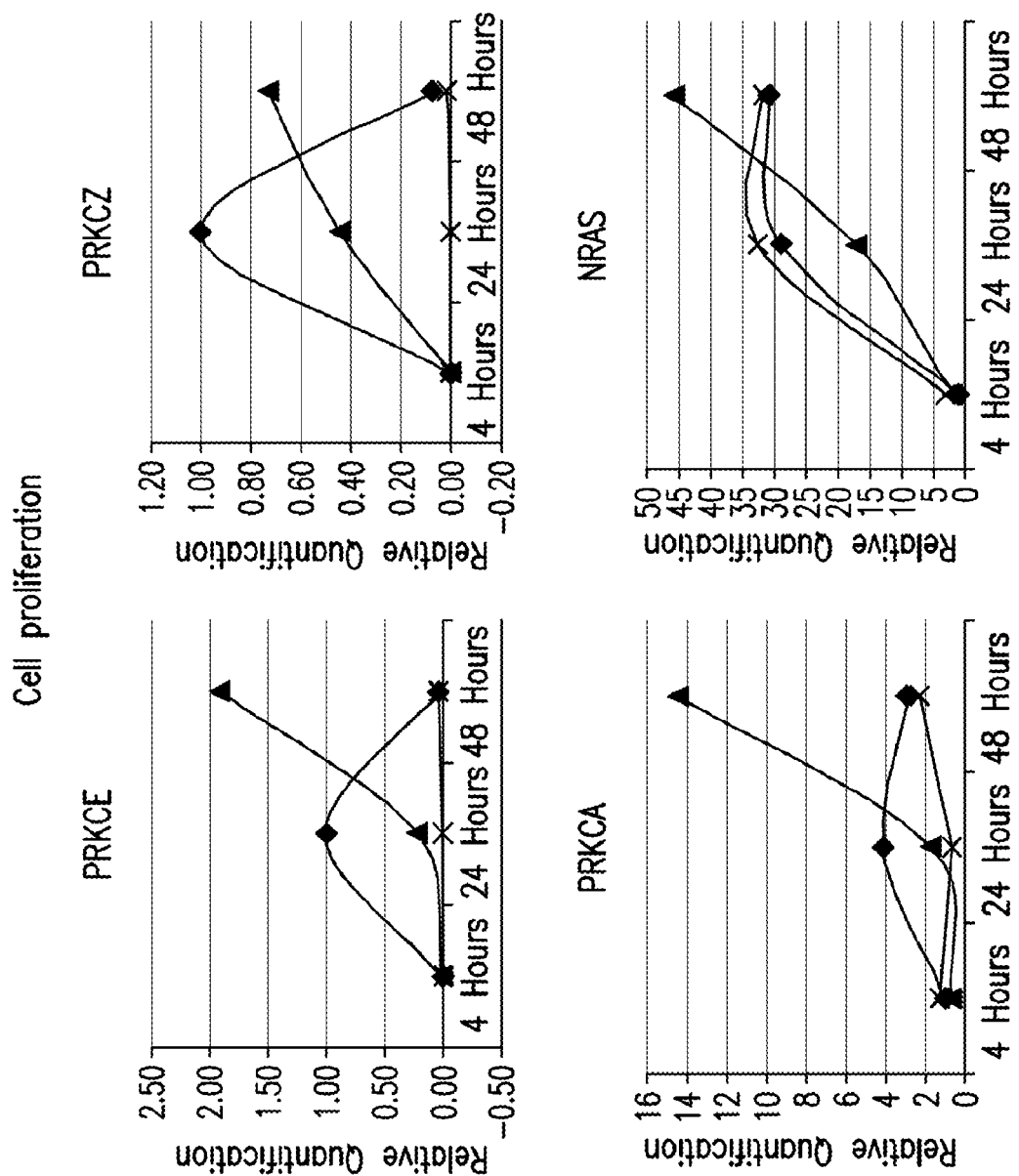
Figure 8F:
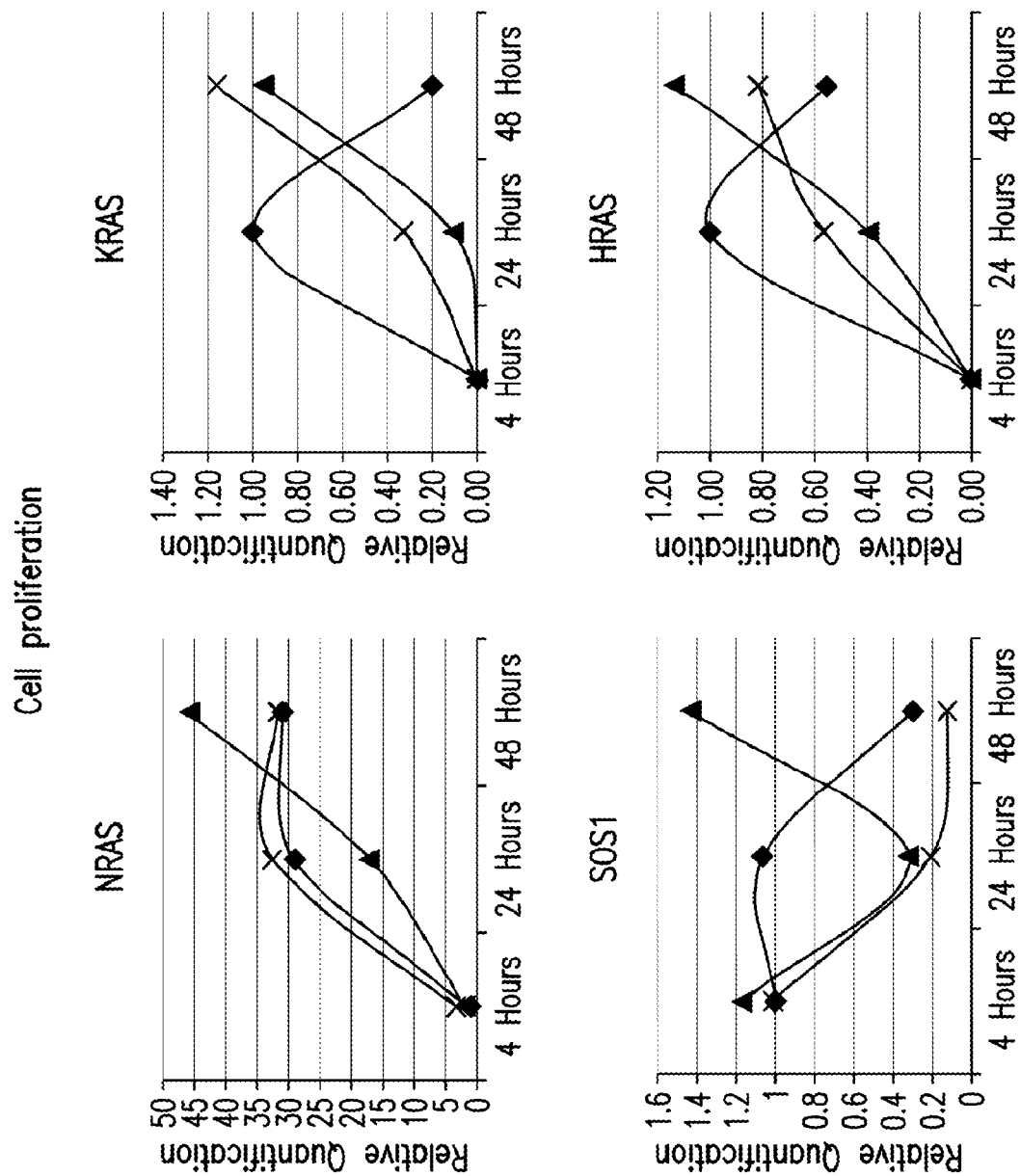

FIGS. 8A-8G shows the effects of placenta-derived adherent cell exosomes on vascular endothelial cell growth and proliferation. FIGS. 8A and 8B show the ability of placenta-derived adherent cell exosomes to promote tube formation and branching of cultured vascular cells, when said exosomes are collected from placenta-derived adherent cell cultures either containing serum (FIG. 8A) or lacking serum (FIG. 8B). FIG. 8C shows the relative expression of VEGF pathway genes after co-cultures with placenta-derived adherent cell exosomes. Darker shades correspond with higher expression, with the exception of the entries in white, which are positive controls (i.e., 18S, GAPDH, HPRT1, and GUSB). FIGS. 8D-8G show the changes in gene expression for VEGF pathway genes over time after co-culturing vascular endothelial cells with placenta-derived adherent cells or placenta-derived adherent cell exosomes. Cultured HUVECs were incubated with placenta-derived adherent cell culture supernatant (crosses), 50 µg of placenta-derived adherent cell exosomes (triangles), or culture medium (diamonds) as a control.

Figure 9A:
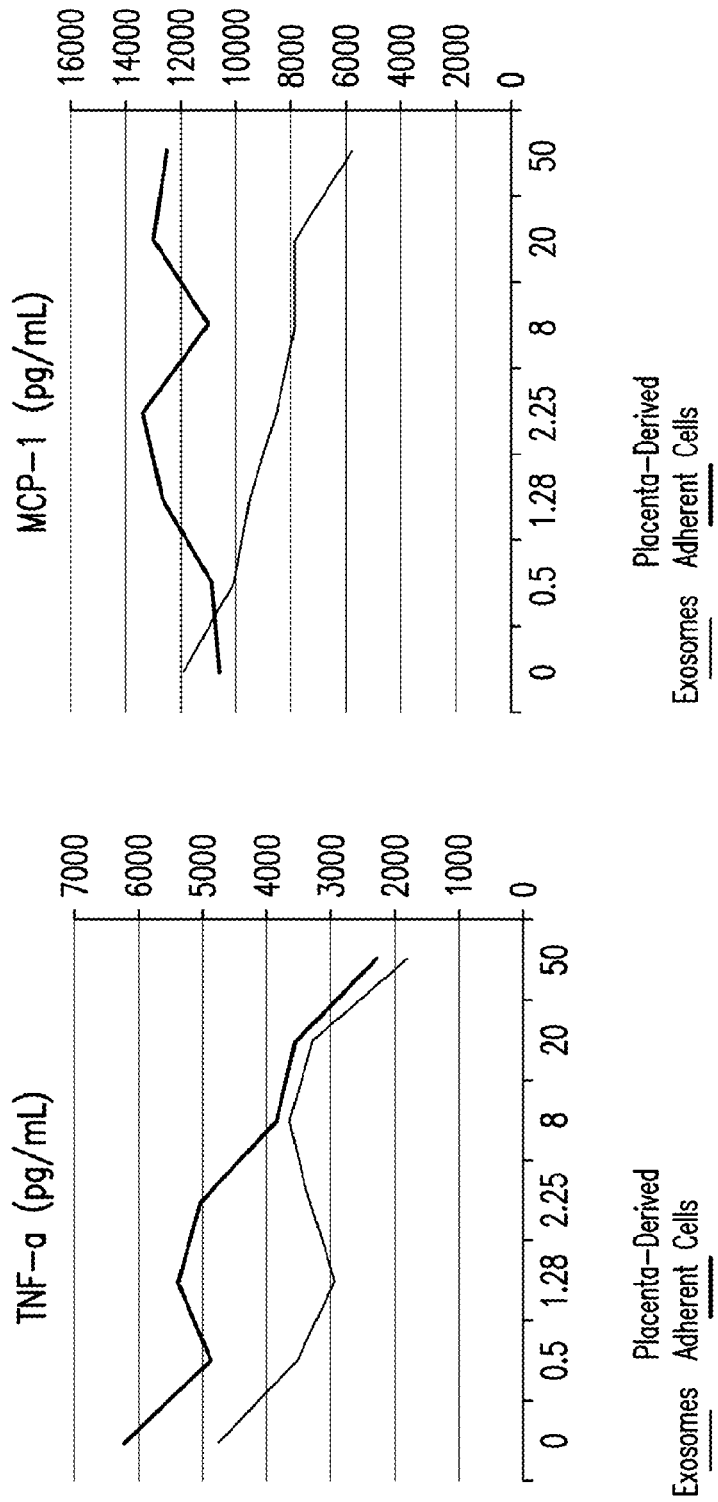
Figure 9B:
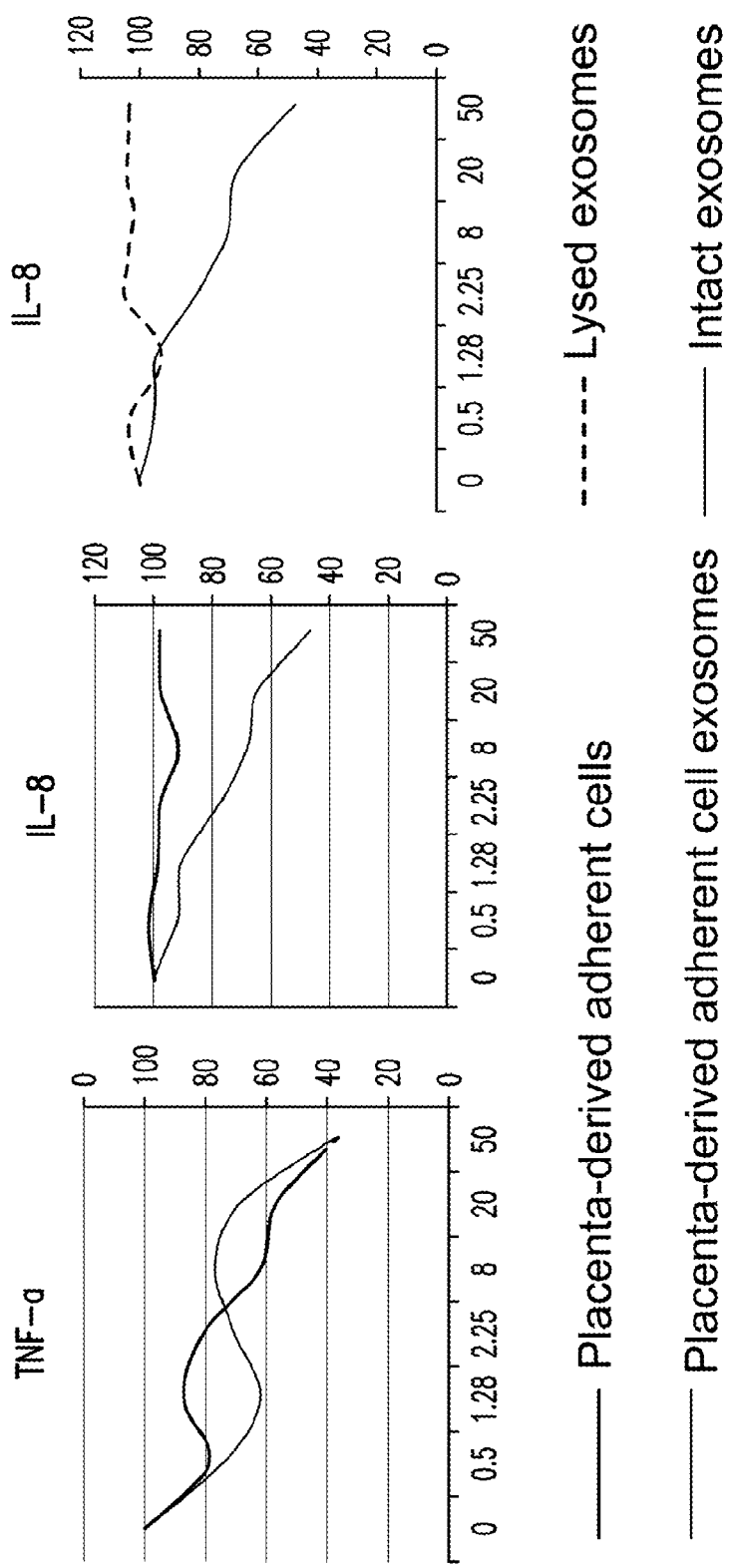

FIGS. 9A-9B: FIG. 9A shows the relative levels of TNF-α and MCP-1 secreted by monocyte-derived macrophages after co-culture with placenta-derived adherent cells or placenta-derived adherent cell exosomes. FIG. 9B shows the level of secretion of TNF-α and IL-8 (left and middle, respectively) secreted by macrophages after co-culture with placenta-derived adherent cells or placenta-derived adherent cell exosomes. Also shown (FIG. 9B, right) is the effect of intact or lysed placenta-derived adherent cell exosomes on IL-8 secretion from monocyte-derived macrophages.

5. DETAILED DESCRIPTION

5.1. Placenta-Derived Adherent Cell Exosomes

The placenta-derived adherent cell exosomes described herein can be selected and identified by their morphology and/or molecular markers, as described below. The placenta-derived adherent cell exosomes described herein are distinct from exosomes known in the art e.g., chorionic villi mesenchymal stem cell-derived exosomes, e.g., those described in Salomon et al., 2013, PLOS ONE, 8:7, e68451. Accordingly, the term "placenta-derived adherent cell exosome," as used herein, is not meant to include exosomes obtained or derived from chorionic villi mesenchymal stem cells.

In certain embodiments, populations of placenta-derived adherent cell exosomes described herein do not comprise cells, e.g., nucleated cells, for example placental cells, e.g., placenta-derived adherent cells.

5.1.1. Placenta-Derived Adherent Cell Exosome Markers

The placenta-derived adherent cell exosomes described herein contain markers that can be used to identify and/or isolate said exosomes. These markers may, for example, be proteins, nucleic acids, saccharide molecules, glycosylated proteins, lipid molecules, and may exist in monomeric, oligomeric and/or multimeric form. In certain embodiments, the markers are produced by the placenta-derived adherent cell from which the exosomes are derived. In certain embodiments, the marker is provided by the placenta-derived adherent cell from which the exosomes are derived, but the marker is not expressed at a higher level by said cell. In a specific embodiment, the markers of placenta-derived adherent cell exosomes described herein are higher in the exosomes as compared to the cell of origin when compared to a control marker molecule. In another specific embodiment, the markers of placenta-derived adherent cell exosomes described herein are enriched in said exosomes as compared to exosomes obtained from another cell type (e.g., the chorionic villi mesenchymal stem cells described in Salomon et al., 2013, PLOS ONE, 8:7, e68451 and pre-adipocyte mesenchymal stem cells), wherein the exosomes are obtained through identical methods and wherein the cells from which the exosomes are derived are maintained under identical conditions.

The three-dimensional structure of exosomes allows for the retention of markers on the surface of the exosome and/or contained within the exosome. Similarly, marker molecules may exist partially within the exosome, partially on the outer surface of the exosome and/or across the phospholipid bilayer of the exosome. In a specific embodiment, the markers associated with the placenta-derived adherent cell exosomes described herein are proteins. In certain embodiments, the markers are transmembrane proteins that are anchored within the exosome phospholipid bilayer, or are anchored across the exosome phospholipid bilayer such that portions of the protein molecule are within the exosome while portions of the same molecule are exposed to the outer surface of the exosome. In certain embodiments, the markers are contained entirely within the exosome. In another specific embodiment, the markers associated with the placenta-derived adherent cell exosomes described herein are nucleic acids. In certain embodiments, said nucleic acids are non-coding RNA molecules, e.g., micro-RNAs (miRNAs).

5.1.1.1. Surface Markers

The placenta-derived adherent cell exosomes described herein comprise surface markers that allow for their identification and that can be used to isolate/obtain substantially pure populations of placenta-derived adherent cell exosomes free from their placenta-derived adherent cells of origin and other cellular and non-cellular material. Methods of for determining exosome surface marker composition are known in the art. For example, exosomal surface markers can be detected by fluorescence-activated cell sorting (FACS) or Western blotting.

The placenta-derived adherent cell exosomes described herein contain distinct surface markers that allow them to be distinguished from other exosomes known in the art. In a specific embodiment, the placenta-derived adherent cell exosomes provided herein comprise one, two, three, four, five, or more of the following markers: CD9, CD10, CD13, CD29, CD44, CD49b, CD49c, CD55, CD59, CD63, CD73, CD81, CD82, CD90, CD98, CD105, CD141, CD142, CD151, CD164, CD295, CD200 (as determinable by, e.g., FACS).

In one specific embodiment, the placenta-derived adherent cell exosomes described herein are CD55$^+$ and CD10$^+$ as determined, e.g., by flow cytometry, for example, by FACS.

In specific embodiments, the placenta-derived adherent cell exosomes described herein are CD10$^+$ and CD55$^+$ (as determined by, e.g., FACS) and additionally contain CD82, CD142, CD49c, and CD90 at a level higher than chorionic villi mesenchymal stem cell exosomes or pre-adipocyte mesenchymal stem cell exosomes (e.g., the chorionic villi mesenchymal stem cells described in Salomon et al., 2013, PLOS ONE, 8:7, e68451).

In a specific embodiment, the placenta-derived adherent cell exosomes described herein are CD9$^+$. In another specific embodiment, the placenta-derived adherent cell exosomes described herein are CD10$^+$. In another specific embodiment, the placenta-derived adherent cell exosomes described herein are CD13⁻. In another specific embodiment, the placenta-derived adherent cell exosomes described herein are CD29⁻. In another specific embodiment, the placenta-derived adherent cell exosomes described herein are CD44⁻. In another specific embodiment, the placenta-derived adherent cell exosomes described herein are CD49b⁺. In another specific embodiment, the placenta-derived adherent cell exosomes described herein are CD49c⁺. In another specific embodiment, the placenta-derived adherent cell exosomes described herein are CD55⁺. In another specific embodiment, the placenta-derived adherent cell exosomes described herein are CD59⁺. In another specific embodiment, the placenta-derived adherent cell exosomes described herein are CD63⁺. In another specific embodiment, the placenta-derived adherent cell exosomes described herein are CD73⁺. In another specific embodiment, the placenta-derived adherent cell exosomes described herein are CD81⁺. In another specific embodiment, the placenta-derived adherent cell exosomes described herein are CD82⁺. In another specific embodiment, the placenta-derived adherent cell exosomes described herein are CD90⁺. In another specific embodiment, the placenta-derived adherent cell exosomes described herein are CD98⁺. In another specific embodiment, the placenta-derived adherent cell exosomes described herein are CD105⁺. In another specific embodiment, the placenta-derived adherent cell exosomes described herein are CD141⁻. In another specific embodiment, the placenta-derived adherent cell exosomes described herein are CD142⁺. In another specific embodiment, the placenta-derived adherent cell exosomes described herein are CD151⁺. In another specific embodiment, the placenta-derived adherent cell exosomes described herein are CD164⁺. In another specific embodiment, the placenta-derived adherent cell exosomes described herein are CD295⁺. In another specific embodiment, the placenta-derived adherent cell exosomes described herein are CD200⁺. Determination of the presence of such markers can be made, e.g., by flow cytometry, for example, by FACS. In another embodiment, described herein are populations of placenta-derived adherent cell exosomes containing any combination of the above-referenced surface markers.

In a specific embodiment, the placenta-derived adherent cell exosomes described herein are CD9⁺ and additionally comprise one or more of the markers selected from the group of CD10, CD13, CD29, CD44, CD49b, CD49c, CD55, CD59, CD63, CD73, CD81, CD82, CD90, CD98, CD105, CD141, CD142, CD151, CD164, CD295, and CD200.

In another specific embodiment, the placenta-derived adherent cell exosomes described herein are CD10⁻ and additionally comprise one or more of the markers selected from the group of CD9, CD13, CD29, CD44, CD49b, CD49c, CD55, CD59, CD63, CD73, CD81, CD82, CD90, CD98, CD105, CD141, CD142, CD151, CD164, CD295, and CD200.

In another specific embodiment, the placenta-derived adherent cell exosomes described herein are CD13⁺ and additionally comprise one or more of the markers selected from the group of CD9, CD10, CD29, CD44, CD49b, CD49c, CD55, CD59, CD63, CD73, CD81, CD82, CD90, CD98, CD105, CD141, CD142, CD151, CD164, CD295, and CD200.

In another specific embodiment, the placenta-derived adherent cell exosomes described herein are CD29⁺ and additionally comprise one or more of the markers selected from the group of CD9, CD10, CD13, CD44, CD49b, CD49c, CD55, CD59, CD63, CD73, CD81, CD82, CD90, CD98, CD105, CD141, CD142, CD151, CD164, CD295, and CD200.

In another specific embodiment, the placenta-derived adherent cell exosomes described herein are CD44⁺ and additionally comprise one or more of the markers selected from the group of CD9, CD10, CD13, CD29, CD49b, CD49c, CD55, CD59, CD63, CD73, CD81, CD82, CD90, CD98, CD105, CD141, CD142, CD151, CD164, CD295, and CD200.

In another specific embodiment, the placenta-derived adherent cell exosomes described herein are CD49b⁺ and additionally comprise one or more of the markers selected from the group of CD9, CD10, CD13, CD29, CD44, CD49c, CD55, CD59, CD63, CD73, CD81, CD82, CD90, CD98, CD105, CD141, CD142, CD151, CD164, CD295, and CD200.

In another specific embodiment, the placenta-derived adherent cell exosomes described herein are CD49c⁺ and additionally comprise one or more of the markers selected from the group of CD9, CD10, CD13, CD29, CD44, CD49b, CD55, CD59, CD63, CD73, CD81, CD82, CD90, CD98, CD105, CD141, CD142, CD151, CD164, CD295, and CD200.

In another specific embodiment, the placenta-derived adherent cell exosomes described herein are CD55⁺ and additionally comprise one or more of the markers selected from the group of CD9, CD10, CD13, CD29, CD44, CD49b, CD49c, CD59, CD63, CD73, CD81, CD82, CD90, CD98, CD105, CD141, CD142, CD151, CD164, CD295, and CD200.

In another specific embodiment, the placenta-derived adherent cell exosomes described herein are CD59⁺ and additionally comprise one or more of the markers selected from the group of CD9, CD10, CD13, CD29, CD44, CD49b, CD49c, CD55, CD63, CD73, CD81, CD82, CD90, CD98, CD105, CD141, CD142, CD151, CD164, CD295, and CD200.

In another specific embodiment, the placenta-derived adherent cell exosomes described herein are CD63⁺ and additionally comprise one or more of the markers selected from the group of CD9, CD10, CD13, CD29, CD44, CD49b, CD49c, CD55, CD59, CD73, CD81, CD82, CD90, CD98, CD105, CD141, CD142, CD151, CD164, CD295, and CD200.

In another specific embodiment, the placenta-derived adherent cell exosomes described herein are CD73⁺ and additionally comprise one or more of the markers selected from the group of CD9, CD10, CD13, CD29, CD44, CD49b, CD49c, CD55, CD59, CD63, CD81, CD82, CD90, CD98, CD105, CD141, CD142, CD151, CD164, CD295, and CD200.

In another specific embodiment, the placenta-derived adherent cell exosomes described herein are CD81⁺ and additionally comprise one or more of the markers selected from the group of CD9, CD10, CD13, CD29, CD44, CD49b, CD49c, CD55, CD59, CD63, CD73, CD82, CD90, CD98, CD105, CD141, CD142, CD151, CD164, CD295, and CD200.

In another specific embodiment, the placenta-derived adherent cell exosomes described herein are CD82⁺ and additionally comprise one or more of the markers selected from the group of CD9, CD10, CD13, CD29, CD44, CD49b, CD49c, CD55, CD59, CD63, CD73, CD81, CD90, CD98, CD105, CD141, CD142, CD151, CD164, CD295, and CD200.

In another specific embodiment, the placenta-derived adherent cell exosomes described herein are CD90⁺ and additionally comprise one or more of the markers selected from the group of CD9, CD10, CD13, CD29, CD44, CD49b, CD49c, CD55, CD59, CD63, CD73, CD81, CD82, CD98, CD105, CD141, CD142, CD151, CD164, CD295, and CD200.

In another specific embodiment, the placenta-derived adherent cell exosomes described herein are CD98⁺ and additionally comprise one or more of the markers selected from the group of CD9, CD10, CD13, CD29, CD44, CD49b, CD49c, CD55, CD59, CD63, CD73, CD81, CD82, CD90, CD105, CD141, CD142, CD151, CD164, CD295, and CD200.

In another specific embodiment, the placenta-derived adherent cell exosomes described herein are CD105⁺ and additionally comprise one or more of the markers selected from the group of CD9, CD10, CD13, CD29, CD44, CD49b, CD49c, CD55, CD59, CD63, CD73, CD81, CD82, CD90, CD98, CD141, CD142, CD151, CD164, CD295, and CD200.

In another specific embodiment, the placenta-derived adherent cell exosomes described herein are CD141⁺ and additionally comprise one or more of the markers selected from the group of CD9, CD10, CD13, CD29, CD44, CD49b, CD49c, CD55, CD59, CD63, CD73, CD81, CD82, CD90, CD98, CD105, CD142, CD151, CD164, CD295, and CD200.

In another specific embodiment, the placenta-derived adherent cell exosomes described herein are CD142⁺ and additionally comprise one or more of the markers selected from the group of CD9, CD10, CD13, CD29, CD44, CD49b, CD49c, CD55, CD59, CD63, CD73, CD81, CD82, CD90, CD98, CD105, CD141, CD151, CD164, CD295, and CD200.

In another specific embodiment, the placenta-derived adherent cell exosomes described herein are CD151⁺ and additionally comprise one or more of the markers selected from the group of CD9, CD10, CD13, CD29, CD44, CD49b, CD49c, CD55, CD59, CD63, CD73, CD81, CD82, CD90, CD98, CD105, CD141, CD142, CD164, CD295, and CD200.

In another specific embodiment, the placenta-derived adherent cell exosomes described herein are CD164⁺ and additionally comprise one or more of the markers selected from the group of CD9, CD10, CD13, CD29, CD44, CD49b, CD49c, CD55, CD59, CD63, CD73, CD81, CD82, CD90, CD98, CD105, CD141, CD142, CD151, CD295, and CD200.

In another specific embodiment, the placenta-derived adherent cell exosomes described herein are CD295⁺ and additionally comprise one or more of the markers selected from the group of CD9, CD10, CD13, CD29, CD44, CD49b, CD49c, CD55, CD59, CD63, CD73, CD81, CD82, CD90, CD98, CD105, CD141, CD142, CD151, and CD200.

In another specific embodiment, the placenta-derived adherent cell exosomes described herein are CD200⁺ and additionally comprise one or more of the markers selected from the group of CD9, CD10, CD13, CD29, CD44, CD49b, CD49c, CD55, CD59, CD63, CD73, CD81, CD82, CD90, CD98, CD105, CD141, CD142, CD164, and CD295.

In another specific embodiment, the placenta-derived adherent cell exosomes described herein are CD49b⁺, CD49c⁺, CD98⁺, CD29⁺, CD142⁺, CD10⁺, CD47⁺, CD55⁺, CD90⁺, CD147⁺, CD151⁺, CD166⁺, CD82⁺ and CD200⁺.

In another embodiment, described herein are populations of placenta-derived adherent cell exosomes containing any combination of the above-referenced surface markers.

The placenta-derived adherent cell exosomes described herein generally do not comprise the surface markers CD3, CD11b, CD14, CD19, CD33, CD192, HLA-A, HLA-B, HLA-C, HLA-DR, CD11c or CD34. Thus, in one embodiment, the placenta-derived adherent cell exosomes described herein are CD3⁻. In another embodiment, the placenta-derived adherent cell exosomes described herein are CD11b⁻. In another embodiment, the placenta-derived adherent cell exosomes described herein are CD14⁻. In another embodiment, the placenta-derived adherent cell exosomes described herein are CD19⁻. In another embodiment, the placenta-derived adherent cell exosomes described herein are CD33⁻. In another embodiment, the placenta-derived adherent cell exosomes described herein are CD192⁻. In another embodiment, the placenta-derived adherent cell exosomes described herein are HLA-A⁻. In another embodiment, the placenta-derived adherent cell exosomes described herein are HLA-B⁻. In another embodiment, the placenta-derived adherent cell exosomes described herein are HLA-C⁻. In another embodiment, the placenta-derived adherent cell exosomes described herein are HLA-DR⁻. In another embodiment, the placenta-derived adherent cell exosomes described herein are CD11c⁻. In another embodiment, the placenta-derived adherent cell exosomes described herein are CD34⁻.

In a specific embodiment, the placenta-derived adherent cell exosomes described herein are CD3 and do not comprise one or more of the markers selected from the group of CD11b, CD14, CD19, CD33, CD192, HLA-A, HLA-B, HLA-C, HLA-DR, CD11c and CD34.

In another specific embodiment, the placenta-derived adherent cell exosomes described herein are CD11b⁻ and do not comprise one or more of the markers selected from the group of CD3, CD14, CD19, CD33, CD192, HLA-A, HLA-B, HLA-C, HLA-DR, CD11c and CD34.

In another specific embodiment, the placenta-derived adherent cell exosomes described herein are CD14⁻ and do not comprise one or more of the markers selected from the group of CD3, CD11b, CD19, CD33, CD192, HLA-A, HLA-B, HLA-C, HLA-DR, CD11c and CD34.

In another specific embodiment, the placenta-derived adherent cell exosomes described herein are CD19⁻ and do not comprise one or more of the markers selected from the group of CD3, CD11b, CD14, CD33, CD192, HLA-A, HLA-B, HLA-C, HLA-DR, CD11c and CD34.

In another specific embodiment, the placenta-derived adherent cell exosomes described herein are CD33⁻ and do not comprise one or more of the markers selected from the group of CD3, CD11b, CD14, CD19, CD192, HLA-A, HLA-B, HLA-C, HLA-DR, CD11c and CD34.

In another specific embodiment, the placenta-derived adherent cell exosomes described herein are CD192⁻ and do not comprise one or more of the markers selected from the group of CD3, CD11b, CD14, CD19, CD33, HLA-A, HLA-B, HLA-C, HLA-DR, CD11c and CD34.

In another specific embodiment, the placenta-derived adherent cell exosomes described herein are HLA-A⁻ and do not comprise one or more of the markers selected from the group of CD3, CD11b, CD14, CD19, CD33, CD192, HLA-B, HLA-C, HLA-DR, CD11c and CD34.

In another specific embodiment, the placenta-derived adherent cell exosomes described herein are HLA-B⁻ and do not comprise one or more of the markers selected from the group of CD3, CD11b, CD14, CD19, CD33, CD192, HLA-A, HLA-C, HLA-DR, CD11c and CD34.

In another specific embodiment, the placenta-derived adherent cell exosomes described herein are HLA-C⁻ and do not comprise one or more of the markers selected from the group of CD3, CD11b, CD14, CD19, CD33, CD192, HLA-A, HLA-B, HLA-DR, CD11c and CD34.

In another specific embodiment, the placenta-derived adherent cell exosomes described herein are HLA-DR⁻ and do not comprise one or more of the markers selected from the group of CD3, CD11b, CD14, CD19, CD33, CD192, HLA-A, HLA-B, HLA-C, CD11c and CD34.

In another specific embodiment, the placenta-derived adherent cell exosomes described herein are CD11c⁻ and do not comprise one or more of the markers selected from the group of CD3, CD11b, CD14, CD19, CD33, CD192, HLA-A, HLA-B, HLA-C, HLA-DR and CD34.

In another specific embodiment, the placenta-derived adherent cell exosomes described herein are CD34⁻ and do not comprise one or more of the markers selected from the group of CD3, CD11b, CD14, CD19, CD33, CD192, HLA-A, HLA-B, HLA-C, HLA-DR and CD11c.

In another specific embodiment, the placenta-derived adherent cell exosomes described herein are CD3⁻, CD11b⁻, CD14⁻, CD19⁻, CD33⁻, CD192⁻, HLA-A⁻, HLA-B⁻, HLA-C⁻, HLA-DR⁻, CD11c⁻ and CD34⁻.

In another specific embodiment, the placenta-derived adherent cell exosomes described herein are CD9+ and additionally comprise one or more of the markers selected from the group of CD10, CD13, CD29, CD44, CD49b, CD49c, CD55, CD59, CD63, CD73, CD81, CD82, CD90, CD98, CD105, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD10+ and additionally comprise one or more of the markers selected from the group of CD9, CD13, CD29, CD44, CD49b, CD49c, CD55, CD59, CD63, CD73, CD81, CD82, CD90, CD98, CD105, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD13+ and additionally comprise one or more of the markers selected from the group of CD9, CD10, CD29, CD44, CD49b, CD49c, CD55, CD59, CD63, CD73, CD81, CD82, CD90, CD98, CD105, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD29+ and additionally comprise one or more of the markers selected from the group of CD9, CD10, CD13, CD44, CD49b, CD49c, CD55, CD59, CD63, CD73, CD81, CD82, CD90, CD98, CD105, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD44+ and additionally comprise one or more of the markers selected from the group of CD9, CD10, CD13, CD29, CD49b, CD49c, CD55, CD59, CD63, CD73, CD81, CD82, CD90, CD98, CD105, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD49b+ and additionally comprise one or more of the markers selected from the group of CD9, CD10, CD13, CD29, CD44, CD49c, CD55, CD59, CD63, CD73, CD81, CD82, CD90, CD98, CD105, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD49c+ and additionally comprise one or more of the markers selected from the group of CD9, CD10, CD13, CD29, CD44, CD49b, CD55, CD59, CD63, CD73, CD81, CD82, CD90, CD98, CD105, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD55+ and additionally comprise one or more of the markers selected from the group of CD9, CD10, CD13, CD29, CD44, CD49b, CD49c, CD59, CD63, CD73, CD81, CD82, CD90, CD98, CD105, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD59+ and additionally comprise one or more of the markers selected from the group of CD9, CD10, CD13, CD29, CD44, CD49b, CD49c, CD55, CD63, CD73, CD81, CD82, CD90, CD98, CD105, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD63+ and additionally comprise one or more of the markers selected from the group of CD9, CD10, CD13, CD29, CD44, CD49b, CD49c, CD55, CD59, CD73, CD81, CD82, CD90, CD98, CD105, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD73+ and additionally comprise one or more of the markers selected from the group of CD9, CD10, CD13, CD29, CD44, CD49b, CD49c, CD55, CD59, CD63, CD81, CD82, CD90, CD98, CD105, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD81+ and additionally comprise one or more of the markers selected from the group of CD9, CD10, CD13, CD29, CD44, CD49b, CD49c, CD55, CD59, CD63, CD73, CD82, CD90, CD98, CD105, CD141, CD142, CD151, CD164, CD295, and CD200, white further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD82+ and additionally comprise one or more of the markers selected from the group of CD9, CD10, CD13, CD29, CD44, CD49b, CD49c, CD55, CD59, CD63, CD73, CD81, CD90, CD98, CD105, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD90+ and additionally comprise one or more of the markers selected from the group of CD9, CD10, CD13, CD29, CD44, CD49b, CD49c, CD55, CD59, CD63, CD73, CD81, CD82, CD98, CD105, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD98+ and additionally comprise one or more of the markers selected from the group of CD9, CD10, CD13, CD29, CD44, CD49b, CD49c, CD55, CD59, CD63, CD73, CD81, CD82, CD90, CD105, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD105+ and additionally comprise one or more of the markers selected from the group of CD9, CD10, CD13, CD29, CD44, CD49b, CD49c, CD55, CD59, CD63, CD73, CD81, CD82, CD90, CD98, CD141, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD141+ and additionally comprise one or more of the markers selected from the group of CD9, CD10, CD13, CD29, CD44, CD49b, CD49c, CD55, CD59, CD63, CD73, CD81, CD82, CD90, CD98, CD105, CD142, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD142+ and additionally comprise one or more of the markers selected from the group of CD9, CD10, CD13, CD29, CD44, CD49b, CD49c, CD55, CD59, CD63, CD73, CD81, CD82, CD90, CD98, CD105, CD141, CD151, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD151+ and additionally comprise one or more of the markers selected from the group of CD9, CD10, CD13, CD29, CD44, CD49b, CD49c, CD55, CD59, CD63, CD73, CD81, CD82, CD90, CD98, CD105, CD141, CD142, CD164, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD164+ and additionally comprise one or more of the markers selected from the group of CD9, CD10, CD13, CD29, CD44, CD49b, CD49c, CD55, CD59, CD63, CD73, CD81, CD82, CD90, CD98, CD105, CD141, CD142, CD151, CD295, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD295+ and additionally comprise one or more of the markers selected from the group of CD9, CD10, CD13, CD29, CD44, CD49b, CD49c, CD55, CD59, CD63, CD73, CD81, CD82, CD90, CD98, CD105, CD141, CD142, CD151, and CD200, while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are CD200+ and additionally comprise one or more of the markers selected from the group of CD9, CD10, CD13, CD29, CD44, CD49b, CD49c, CD55, CD59, CD63, CD73, CD81, CD82, CD90, CD98, CD105, CD141, CD142, CD164, and CD295, while further lacking one or more of the markers selected from the group of CD3, CD11b, CD14, CD19, CD33, CD192, HLA-A, HLA-B, HLA-C, HLA-DR, CD11c and CD34.

In another embodiment, described herein are populations of placenta-derived adherent cell exosomes containing any combination of the above-referenced surface markers.

In another specific embodiment, the placenta-derived adherent cell exosomes described herein are $CD9^+$, $CD10^+$, $CD13^+$, $CD29^+$, $CD44^+$, $CD49b^+$, $CD49c^+$, $CD55^+$, $CD59^+$, $CD63^+$, $CD73^+$, $CD81^+$, $CD82^+$, $CD90^+$, $CD98^+$, $CD105^+$, $CD141^+$, $CD142^+$, $CD151^+$, $CD164^+$, $CD295^+$, and $CD200^+$ while further lacking one or more of the markers selected from the group of CD3, CD11b, CD14, CD19, CD33, CD192, HLA-A, HLA-B, HLA-C, HLA-DR, CD11c and CD34.

In another specific embodiment, the placenta-derived adherent cell exosomes described herein are $CD3^-$, $CD11b^-$, $CD14^-$, $CD19^-$, $CD33^-$, $CD192^-$, $HLA-A^-$, $HLA-B^-$, $HLA-C^-$, $HLA-DR^-$, $CD11c^-$ and $CD34^-$ while additionally comprising one or more of the markers selected from the group of CD9, CD10, CD13, CD29, CD44, CD49b, CD49c, CD55, CD59, CD63, CD73, CD81, CD82, CD90, CD98, CD105, CD141, CD142, CD151, CD164, CD295, and CD200.

In another specific embodiment, the placenta-derived adherent cell exosomes described herein are $CD9^+$, $CD10^+$, $CD13^+$, $CD29^+$, $CD44^+$, $CD49b^+$, $CD49c^+$, $CD55^+$, $CD59^+$, CD63$^+$, CD73$^+$, CD81$^+$, CD82$^+$, CD90$^+$, CD98$^+$, CD105$^+$, CD141$^+$, CD142$^+$, CD151$^+$, CD164$^+$, CD295$^+$, CD200$^+$, CD3$^-$, CD11b$^-$, CD14$^-$, CD19$^-$, CD33$^-$, CD192$^-$, HLA-A$^-$, HLA-B$^-$, HLA-C$^-$, HLA-DR$^-$, CD11c$^-$ and CD34$^-$.

In another embodiment, the placenta-derived adherent cell exosomes described herein do not contain detectable levels of CD4, CD5, CD6, CD7, CD8, CD16, CD24, CD25, CD26, CD27, CD32, CD35, CD37, CD39, CD45, CD46, CD54, CD56, CD61, CD74, CD86, CD88, CD91, CD99, CD103, CD108, CD112, CD117, CD119, CD120a, CD123, CD126, CD130, CD134, CD138, CD140a, CD140b, CD144, CD146, CD147, CD152, CD163, CD183, CD184, CD186, CD191, CD194, CD196, CD198, CD202b, CD220, CD221, CD235a, CD252, CD266, CD271, CD273, CD274, CD318, CD326, CD333, CD334, HLA-DP, HLA-DQ, HLA-G, IgD, IgM, NG2, PDGF, and/or SSEA-3.

In certain embodiments, the placenta-derived adherent cell exosomes described herein are CD82$^+$ and contain a low level of CD141 (i.e., are CD141 (low)) as determined, e.g., by flow cytometry, for example, by FACS.

In certain embodiments, the placenta-derived adherent cell exosomes described herein comprise a surface marker at a greater amount than exosomes known in the art, as determinable by, e.g., FACS. In a specific embodiment, the placenta-derived adherent cell exosomes described herein comprise a higher amount of CD49c, CD82, CD90, and/or CD142 than the amount of said marker(s) in a non placenta-derived adherent cell exosome. In a specific embodiment, the placenta-derived adherent cell exosomes described herein comprise a higher amount of CD49c, CD82, CD90, and/or CD142 than the amount of said marker(s) that is present in exosomes derived from either pre-adipocyte mesenchymal stem cells or chorionic villi mesenchymal stem cells (e.g., the chorionic villi mesenchymal stem cells described in Salomon et al., 2013, PLOS ONE, 8:7, e68451). In a specific embodiment, the placenta-derived adherent cell exosomes described herein comprise a higher amount of CD49c, CD73, CD82, CD90, and/or CD142 than the amount of said marker(s) that is present in exosomes derived from pre-adipocyte mesenchymal stem cells.

In a specific embodiment, the placenta-derived adherent cell exosomes described herein comprise a lower amount of CD164 than the amount of said marker(s) in a non placenta-derived adherent cell exosome. In a specific embodiment, the placenta-derived adherent cell exosomes described herein comprise a lower amount of CD164 than the amount of said marker(s) that is present in exosomes derived from pre-adipocyte mesenchymal stem cells or chorionic villi mesenchymal stem cells (e.g., the chorionic villi mesenchymal stem cells described in Salomon et al., 2013, PLOS ONE, 8:7, e68451). In a specific embodiment, the placenta-derived adherent cell exosomes described herein comprise CD164 at a level two-fold, three-fold, four-fold, five-fold, six-fold, seven-fold, eight-fold, nine-fold, or ten-fold lower than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD164 content is measured under the same experimental conditions (e.g., by flow cytometry, for example, by FACS), wherein the exosomes are harvested under like conditions, and wherein the cells of origin are grown under like conditions. In another specific embodiment, the placenta-derived adherent cell exosomes described herein comprise CD164 at a level two-fold to three-fold, three-fold to four-fold, four-fold to five-fold, five-fold to six-fold, six-fold to seven-fold, seven-fold to eight-fold, eight-fold to nine-fold or nine-fold to ten-fold lower than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD164 content is measured under the same experimental conditions (e.g., by flow cytometry, for example, by FACS), wherein the exosomes are harvested under like conditions, and wherein the cells of origin are grown under like conditions. In a specific embodiment, the placenta-derived adherent cell exosomes described herein comprise CD164 at a level two-fold, three-fold, four-fold, five-fold, six-fold, seven-fold, eight-fold, nine-fold, or ten-fold lower than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD164 content is measured under the same experimental conditions (e.g., by flow cytometry, for example, by FACS), and wherein the same number and/or mass of exosomes is used for each sample. In another specific embodiment, the placenta-derived adherent cell exosomes described herein comprise CD164 at a level two-fold to three-fold, three-fold to four-fold, four-fold to five-fold, five-fold to six-fold, six-fold to seven-fold, seven-fold to eight-fold, eight-fold to nine-fold or nine-fold to ten-fold lower than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD164 content is measured under the same experimental conditions (e.g., by flow cytometry, for example, by FACS), and wherein the same number and/or mass of exosomes is used for each sample.

In another specific embodiment, the placenta-derived adherent cell exosomes described herein comprise CD49c at a level two-fold, three-fold, four-fold, five-fold, six-fold, seven-fold, eight-fold, nine-fold, or ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD49c content is measured under the same experimental conditions (e.g., by flow cytometry, for example, by FACS), wherein the exosomes are harvested under like conditions, and wherein the cells of origin are grown under like conditions. In another specific embodiment, the placenta-derived adherent cell exosomes described herein comprise CD49c at a level two-fold to three-fold, three-fold to four-fold, four-fold to five-fold, five-fold to six-fold, six-fold to seven-fold, seven-fold to eight-fold, eight-fold to nine-fold or nine-fold to ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD49c content is measured under the same experimental conditions (e.g., by flow cytometry, for example, by FACS), wherein the exosomes are harvested under like conditions, and wherein the cells of origin are grown under like conditions. In another specific embodiment, the placenta-derived adherent cell exosomes described herein comprise CD49c at a level two-fold, three-fold, four-fold, five-fold, six-fold, seven-fold, eight-fold, nine-fold, or ten-fold higher than exosomes derived from chorionic villi mesenchymal stem cells described in Salomon et al., 2013, PLOS ONE, 8:7, e68451) or pre-adipocyte mesenchymal stem cells, wherein CD49c content is measured under the same experimental conditions (e.g., by flow cytometry, for example, by FACS), and wherein the same number and/or mass of exosomes is used for each sample. In another specific embodiment, the placenta-derived adherent cell exosomes described herein comprise CD49c at a level two-fold to three-fold, three-fold to four-fold, four-fold to five-fold, five-fold to six-fold, six-fold to seven-fold, seven-fold to eight-fold, eight-fold to nine-fold or nine-fold to ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD49c content is measured under the same experimental conditions (e.g., by flow cytometry, for example, by FACS), and wherein the same number and/or mass of exosomes is used for each sample.

In another specific embodiment, the placenta-derived adherent cell exosomes described herein comprise CD73 at a level two-fold, three-fold, four-fold, five-fold, six-fold, seven-fold, eight-fold, nine-fold, or ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD73 content is measured under the same experimental conditions (e.g., by flow cytometry, for example, by FACS), wherein the exosomes are harvested under like conditions, and wherein the cells of origin are grown under like conditions. In another specific embodiment, the placenta-derived adherent cell exosomes described herein comprise CD73 at a level two-fold to three-fold, three-fold to four-fold, four-fold to five-fold, five-fold to six-fold, six-fold to seven-fold, seven-fold to eight-fold, eight-fold to nine-fold or nine-fold to ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD73 content is measured under the same experimental conditions (e.g., by flow cytometry, for example, by FACS), wherein the exosomes are harvested under like conditions, and wherein the cells of origin are grown under like conditions. In another specific embodiment, the placenta-derived adherent cell exosomes described herein comprise CD73 at a level two-fold, three-fold, four-fold, five-fold, six-fold, seven-fold, eight-fold, nine-fold, or ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD73 content is measured under the same experimental conditions (e.g., by flow cytometry, for example, by FACS), and wherein the same number and/or mass of exosomes is used for each sample. In another specific embodiment, the placenta-derived adherent cell exosomes described herein comprise CD73 at a level two-fold to three-fold, three-fold to four-fold, four-fold to five-fold, five-fold to six-fold, six-fold to seven-fold, seven-fold to eight-fold, eight-fold to nine-fold or nine-fold to ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD73 content is measured under the same experimental conditions (e.g., by flow cytometry, for example, by FACS), and wherein the same number and/or mass of exosomes is used for each sample.

In a specific embodiment, the placenta-derived adherent cell exosomes described herein comprise CD82 at a level two-fold, three-fold, four-fold, five-fold, six-fold, seven-fold, eight-fold, nine-fold, or ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD82 content is measured under the same experimental conditions (e.g., by flow cytometry, for example, by FACS), wherein the exosomes are harvested under like conditions, and wherein the cells of origin are grown under like conditions. In another specific embodiment, the placenta-derived adherent cell exosomes described herein comprise CD82at a level two-fold to three-fold, three-fold to four-fold, four-fold to five-fold, five-fold to six-fold, six-fold to seven-fold, seven-fold to eight-fold, eight-fold to nine-fold or nine-fold to ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD82 content is measured under the same experimental conditions (e.g., by flow cytometry, for example, by FACS), wherein the exosomes are harvested under like conditions, and wherein the cells of origin are grown under like conditions. In a specific embodiment, the placenta-derived adherent cell exosomes described herein comprise CD82 at a level two-fold, three-fold, four-fold, five-fold, six-fold, seven-fold, eight-fold, nine-fold, or ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD82 content is measured under the same experimental conditions (e.g., by flow cytometry, for example, by FACS), and wherein the same number and/or mass of exosomes is used for each sample. In another specific embodiment, the placenta-derived adherent cell exosomes described herein comprise CD82at a level two-fold to three-fold, three-fold to four-fold, four-fold to five-fold, five-fold to six-fold, six-fold to seven-fold, seven-fold to eight-fold, eight-fold to nine-fold or nine-fold to ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD82 content is measured under the same experimental conditions (e.g., by flow cytometry, for example, by FACS), and wherein the same number and/or mass of exosomes is used for each sample.

In a specific embodiment, the placenta-derived adherent cell exosomes described herein comprise CD90 at a level two-fold, three-fold, four-fold, five-fold, six-fold, seven-fold, eight-fold, nine-fold, or ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD90 content is measured under the same experimental conditions (e.g., by flow cytometry, for example, by FACS), wherein the exosomes are harvested under like conditions, and wherein the cells of origin are grown under like conditions. In another specific embodiment, the placenta-derived adherent cell exosomes described herein comprise CD90 at a level two-fold to three-fold, three-fold to four-fold, four-fold to five-fold, five-fold to six-fold, six-fold to seven-fold, seven-fold to eight-fold, eight-fold to nine-fold or nine-fold to ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD90 content is measured under the same experimental conditions (e.g., by flow cytometry, for example, by FACS), wherein the exosomes are harvested under like conditions, and wherein the cells of origin are grown under like conditions. In a specific embodiment, the placenta-derived adherent cell exosomes described herein comprise CD90 at a level two-fold, three-fold, four-fold, five-fold, six-fold, seven-fold, eight-fold, nine-fold, or ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD90 content is measured under the same experimental conditions (e.g., by flow cytometry, for example, by FACS), and wherein the same number and/or mass of exosomes is used for each sample. In another specific embodiment, the placenta-derived adherent cell exosomes described herein comprise CD90 at a level two-fold to three-fold, three-fold to four-fold, four-fold to five-fold, five-fold to six-fold, six-fold to seven-fold, seven-fold to eight-fold, eight-fold to nine-fold or nine-fold to ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD90 content is measured under the same experimental conditions (e.g., by flow cytometry, for example, by FACS), and wherein the same number and/or mass of exosomes is used for each sample.

In another specific embodiment, placenta-derived adherent cell exosomes described herein comprise CD142 at a level two-fold, three-fold, four-fold, five-fold, six-fold, seven-fold, eight-fold, nine-fold, or ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD142 content is measured under the same experimental conditions (e.g., by flow cytometry, for example, by FACS), wherein the exosomes are harvested under like conditions, and wherein the cells of origin are grown under like conditions. In another embodiment, the placenta-derived adherent cell exosomes described herein comprise CD142 at a level two-fold to three-fold, three-fold to four-fold, four-fold to five-fold, five-fold to six-fold, six-fold to seven-fold, seven-fold to eight-fold, eight-fold to nine-fold or nine-fold to ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD142 content is measured under the same experimental conditions (e.g., by flow cytometry, for example, by FACS), wherein the exosomes are harvested under like conditions, and wherein the cells of origin are grown under like conditions. In another specific embodiment, placenta-derived adherent cell exosomes described herein comprise CD142 at a level two-fold, three-fold, four-fold, five-fold, six-fold, seven-fold, eight-fold, nine-fold, or ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD142 content is measured under the same experimental conditions (e.g., by flow cytometry, for example, by FACS), and wherein the same number and/or mass of exosomes is used for each sample. In another specific embodiment, the placenta-derived adherent cell exosomes described herein comprise CD142 at a level two-fold to three-fold, three-fold to four-fold, four-fold to five-fold, five-fold to six-fold, six-fold to seven-fold, seven-fold to eight-fold, eight-fold to nine-fold or nine-fold to ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD142 content is measured under the same experimental conditions (e.g., by flow cytometry, for example, by FACS), and wherein the same number and/or mass of exosomes is used for each sample.

In another specific embodiment, the placenta-derived adherent cell exosomes described herein comprise CD49c, CD90, CD142 and CD82 at a level two-fold, three-fold, four-fold, five-fold, six-fold, seven-fold, eight-fold, nine-fold, or ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD49c, CD90, CD142 and CD82 content is measured under the same experimental conditions (e.g., by flow cytometry, for example, by FACS), wherein the exosomes are harvested under like conditions, and wherein the cells of origin are grown under like conditions. In another specific embodiment, the placenta-derived adherent cell exosomes described herein comprise CD49c, CD90, CD142 and CD82 at a level two-fold to three-fold, three-fold to four-fold, four-fold to five-fold, five-fold to six-fold, six-fold to seven-fold, seven-fold to eight-fold, eight-fold to nine-fold or nine-fold to ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD49c, CD90, CD142 and CD82 content is measured under the same experimental conditions (e.g., by flow cytometry, for example, by FACS), wherein the exosomes are harvested under like conditions, and wherein the cells of origin are grown under like conditions. In another specific embodiment, the placenta-derived adherent cell exosomes described herein comprise CD49c, CD90, CD142 and CD82 at a level two-fold, three-fold, four-fold, five-fold, six-fold, seven-fold, eight-fold, nine-fold, or ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD49c, CD90, CD142 and CD82 content is measured under the same experimental conditions (e.g., by flow cytometry, for example, by FACS), and wherein the same number and/or mass of exosomes is used for each sample. In another specific embodiment, the placenta-derived adherent cell exosomes described herein comprise CD49c, CD90, CD142 and CD82 at a level two-fold to three-fold, three-fold to four-fold, four-fold to five-fold, five-fold to six-fold, six-fold to seven-fold, seven-fold to eight-fold, eight-fold to nine-fold or nine-fold to ten-fold higher than exosomes derived from chorionic villi mesenchymal stem cells (e.g., the chorionic villi mesenchymal stem cells described in Salomon et al., 2013, PLOS ONE, 8:7, e68451) or pre-adipocyte mesenchymal stem cells, wherein CD49c, CD90, CD142 and CD82 content is measured under the same experimental conditions (e.g., by flow cytometry, for example, by FACS), and wherein the same number and/or mass of exosomes is used for each sample.

In addition to the exosomal markers described herein, placenta-derived adherent cell exosomes described herein may additionally comprise certain other exosomal markers. For example, in specific embodiments, the placenta-derived adherent cell exosomes described herein comprise exosomal surface markers FLOT1, ALIX, ANXA5, and TSG101 in addition to any marker combination described herein. In another embodiment, disclosed herein are compositions of placenta-derived adherent cell exosomes containing any combination of the above-referenced surface markers.

5.1.1.2. MicroRNAs

In certain embodiments, the placenta-derived adherent cell exosomes described herein contain one or more nucleic acid molecules, e.g., one or more non-coding RNA molecules. In a specific embodiment, the placenta-derived adherent cell exosomes provided herein comprise microRNAs (miRNAs). Generally, miRNAs are 17-22 nucleotide (nt) non-coding RNAs that modulate a broad range of cellular functions and are implicated in diseases and metabolic regulation. Methods of detecting miRNA levels are well known in the art, e.g., real-time PCR (RT-PCR), for example, Taqman assay. In other specific embodiments, the placenta-derived adherent cell exosomes contain miRNAs that, when subjected to RT-PCR and compared to a control RNA, are contained at a level 1.1, 2, 5, 10, 100, 500, 600, 700, 800, 900, 1000, 1100 or 1200 times higher than the same miRNA in chorionic villi mesenchymal stem cells, or between 1.1 and 2, 2 and 5, 2 and 10, 5 and 10, 10 and 100, 100 and 500, 500 and 600, 600 and 700, 700 and 800, 800 and 900, 900 and 1000, 1000 and 1100, or 1100 and 1200 times higher than the same miRNA in chorionic villi mesenchymal stem cells.

In certain embodiments, the placenta-derived adherent cell exosomes described herein contain detectable levels of one, two, three, four or more of the following miRNAs: miR-218-5p, miR-133b, miR-422a, miR-564, miR-16-5p, let-7a, miR-92, miR-142-3p, miR-451, miR-124-5p, miR-223-3p, miR-630, miR-296-5p, let-7b-3p and let-7d-3p. In one embodiment, the placenta-derived adherent cell exosomes described herein comprise detectable levels of miR-218-5p. In another embodiment, the placenta-derived adherent cell exosomes described herein comprise detectable levels of miR-133b. In another embodiment, the placenta-derived adherent cell exosomes described herein comprise detectable levels of miR-422a. In another embodiment, the placenta-derived adherent cell exosomes described herein comprise detectable levels of miR-564. In another embodiment, the placenta-derived adherent cell exosomes described herein comprise detectable levels of miR-16-5p. In another embodiment, the placenta-derived adherent cell exosomes described herein comprise detectable levels of lct-7a. In another embodiment, the placenta-derived adherent cell exosomes described herein comprise detectable levels of miR-92. In another embodiment, the placenta-derived adherent cell exosomes described herein comprise detectable levels of miR-142-3p. In another embodiment, the placenta-derived adherent cell exosomes described herein comprise detectable levels of miR-451. In another embodiment, the placenta-derived adherent cell exosomes described herein comprise detectable levels of miR-124-5p. In another embodiment, the placenta-derived adherent cell exosomes described herein comprise detectable levels of miR-223-3p. In another embodiment, the placenta-derived adherent cell exosomes described herein comprise detectable levels of miR-630. In another embodiment, the placenta-derived adherent cell exosomes described herein comprise detectable levels of miR-296-5p. In another embodiment, the placenta-derived adherent cell exosomes described herein comprise detectable levels of let-7b-3p. In another embodiment, the placenta-derived adherent cell exosomes described herein comprise detectable levels of let-7d-3p.

In one embodiment, the placenta-derived adherent cell exosomes described herein comprise detectable levels of miR-218-5p and additionally comprise detectable levels of one or more of the miRNAs selected from the group of miR-133b, miR-422a, miR-564, miR-16-5p, let-7a, miR-92, miR-142-3p, miR-451, miR-124-5p, miR-223-3p, miR-630, miR-296-5p, let-7b-3p and let-7d-3p.

In another embodiment, the placenta-derived adherent cell exosomes described herein comprise detectable levels of miR-133b and additionally comprise detectable levels of one or more of the miRNAs selected from the group of miR-218-5p, miR-422a, miR-564, miR-16-5p, let-7a, miR-92, miR-142-3p, miR-451, miR-124-5p, miR-223-3p, miR-630, miR-296-5p, let-7b-3p and let-7d-3p.

In another embodiment, the placenta-derived adherent cell exosomes described herein comprise detectable levels of miR-422a and additionally comprise detectable levels of one or more of the miRNAs selected from the group of miR-218-5p, miR-133b, miR-564, miR-16-5p, let-7a, miR-92, miR-142-3p, miR-451, miR-124-5p, miR-223-3p, miR-630, miR-296-5p, let-7b-3p and let-7d-3p.

In another embodiment, the placenta-derived adherent cell exosomes described herein comprise detectable levels of miR-564 and additionally comprise detectable levels of one or more of the miRNAs selected from the group of miR-218-5p, miR-133b, miR-422a, miR-16-5p, lct-7a, miR-92, miR-142-3p, miR-451, miR-124-5p, miR-223-3p, miR-630, miR-296-5p, lct-7b-3p and let-7d-3p.

In another embodiment, the placenta-derived adherent cell exosomes described herein comprise detectable levels of miR-16-5p and additionally comprise detectable levels of one or more of the miRNAs selected from the group of miR-218-5p, miR-133b, miR-422a, miR-564, let-7a, miR-92, miR-142-3p, miR-451, miR-124-5p, miR-223-3p, miR-630, miR-296-5p, let-7b-3p and let-7d-3p.

In another embodiment, the placenta-derived adherent cell exosomes described herein comprise detectable levels of let-7a and additionally comprise detectable levels of one or more of the miRNAs selected from the group of miR-218-5p, miR-133b, miR-422a, miR-564, miR-16-5p, miR-92, miR-142-3p, miR-451, miR-124-5p, miR-223-3p, miR-630, miR-296-5p, let-7b-3p and let-7d-3p.

In another embodiment, the placenta-derived adherent cell exosomes described herein comprise detectable levels of miR-92 and additionally comprise detectable levels of one or more of the miRNAs selected from the group of miR-218-5p, miR-133b, miR-422a, miR-564, miR-16-5p, let-7a, miR-142-3p, miR-451, miR-124-5p, miR-223-3p, miR-630, miR-296-5p, let-7b-3p and let-7d-3p.

In another embodiment, the placenta-derived adherent cell exosomes described herein comprise detectable levels of miR-142-3p and additionally comprise detectable levels of one or more of the miRNAs selected from the group of miR-218-5p, miR-133b, miR-422a, miR-564, miR-16-5p, let-7a, miR-92, miR-451, miR-124-5p, miR-223-3p, miR-630, miR-296-5p, let-7b-3p and let-7d-3p.

In another embodiment, the placenta-derived adherent cell exosomes described herein comprise detectable levels of miR-451 and additionally comprise detectable levels of one or more of the miRNAs selected from the group of miR- 218-5p, miR-133b, miR-422a, miR-564, miR-16-5p, let-7a, miR-92, miR-142-3p, miR-124-5p, miR-223-3p, miR-630, miR-296-5p, let-7b-3p and let-7d-3p.

In another embodiment, the placenta-derived adherent cell exosomes described herein comprise detectable levels of miR-124-5p and additionally comprise detectable levels of one or more of the miRNAs selected from the group of miR-218-5p, miR-133b, miR-422a, miR-564, miR-16-5p, lct-7a, miR-92, miR-142-3p, miR-451, miR-223-3p, miR-630, miR-296-5p, lct-7b-3p and let-7d-3p.

In another embodiment, the placenta-derived adherent cell exosomes described herein comprise detectable levels of miR-223-3p and additionally comprise detectable levels of one or more of the miRNAs selected from the group of miR-218-5p, miR-133b, miR-422a, miR-564, miR-16-5p, let-7a, miR-92, miR-142-3p, miR-451, miR-124-5p, miR-630, miR-296-5p, let-7b-3p and let-7d-3p.

In another embodiment, the placenta-derived adherent cell exosomes described herein comprise detectable levels of miR-630 and additionally comprise detectable levels of one or more of the miRNAs selected from the group of miR-218-5p, miR-133b, miR-422a, miR-564, miR-16-5p, let-7a, miR-92, miR-142-3p, miR-451, miR-124-5p, miR-223-3p, miR-296-5p, let-7b-3p and let-7d-3p.

In another embodiment, the placenta-derived adherent cell exosomes described herein comprise detectable levels of miR-296-5p and additionally comprise detectable levels of one or more of the miRNAs selected from the group of miR-218-5p, miR-133b, miR-422a, miR-564, miR-16-5p, let-7a, miR-92, miR-142-3p, miR-451, miR-124-5p, miR-223-3p, miR-630, let-7b-3p and let-7d-3p.

In another embodiment, the placenta-derived adherent cell exosomes described herein comprise detectable levels of let-7b-3p and additionally comprise detectable levels of one or more of the miRNAs selected from the group of miR-218-5p, miR-133b, miR-422a, miR-564, miR-16-5p, let-7a, miR-92, miR-142-3p, miR-451, miR-124-5p, miR-223-3p, miR-630, miR-296-5p and let-7d-3p.

In another embodiment, the placenta-derived adherent cell exosomes described herein comprise detectable levels of let-7d-3p and additionally comprise detectable levels of one or more of the miRNAs selected from the group of miR-218-5p, miR-133b, miR-422a, miR-564, miR-16-5p, let-7a, miR-92, miR-142-3p, miR-451, miR-124-5p, miR-223-3p, miR-630, miR-296-5p and let-7b-3p.

In a specific embodiment, the placenta-derived adherent cell exosomes described herein comprise miR-218-5p, miR-133b, miR-422a, miR-564, miR-16-5p, let-7a, miR-92, miR-142-3p, miR-451, miR-124-5p, miR-223-3p, miR-630, miR-296-5p, let-7b-3p and let-7d-3p.

In certain embodiments, the placenta-derived adherent cell exosomes described herein can be distinguished from exosomes from other cells (e.g., chorionic villi mesenchymal stem cells, e.g., the chorionic villi mesenchymal stem cells described in Salomon et al., 2013, PLOS ONE, 8:7, e68451) based on the miRNA they comprise.

In a specific embodiment, the placenta-derived adherent cell exosomes described herein comprise miR-133b at a level at least two-fold higher when compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated under like conditions.

In another embodiment, the placenta-derived adherent cell exosomes described herein comprise miR-422a at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In another embodiment, the placenta-derived adherent cell exosomes described herein comprise miR-16-5p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In another embodiment, the placenta-derived adherent cell exosomes described herein comprise let-7a at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In another embodiment, the placenta-derived adherent cell exosomes described herein comprise miR-92 at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In another embodiment, the placenta-derived adherent cell exosomes described herein comprise miR-142-3p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In another embodiment, the placenta-derived adherent cell exosomes described herein comprise miR-451 at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In another embodiment, the placenta-derived adherent cell exosomes described herein comprise miR-124-5p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In another embodiment, the placenta-derived adherent cell exosomes described herein comprise miR-223-3p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In another embodiment, the placenta-derived adherent cell exosomes described herein comprise miR-630 at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In another embodiment, the placenta-derived adherent cell exosomes described herein comprise miR-296-5p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In another embodiment, the placenta-derived adherent cell exosomes described herein comprise lct-7b-3p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In another embodiment, the placenta-derived adherent cell exosomes described herein comprise let-7d-3p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In one embodiment, the placenta-derived adherent cell exosomes described herein comprise miR-133b and additionally one or more miRNA selected from the group of miR-422a, miR-16-5p, let-7a, miR-92, miR-142-3p, miR-451, miR-223-3p, miR-630, miR-296-5p, let-7b-3p and let-7d-3p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In one embodiment, the placenta-derived adherent cell exosomes described herein comprise miR-422a and additionally one or more miRNA selected from the group of miR-133b, miR-16-5p, let-7a, miR-92, miR-142-3p, miR-451, miR-223-3p, miR-630, miR-296-5p, let-7b-3p and let-7d-3p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In one embodiment, the placenta-derived adherent cell exosomes described herein comprise miR-16-5p and additionally one or more miRNA selected from the group of miR-133b, miR-422a, let-7a, miR-92, miR-142-3p, miR-451, miR-223-3p, miR-630, miR-296-5p, let-7b-3p and let-7d-3p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In one embodiment, the placenta-derived adherent cell exosomes described herein comprise let-7a and additionally one or more miRNA selected from the group of miR-133b, miR-422a, miR-16-5p, miR-92, miR-142-3p, miR-451, miR-223-3p, miR-630, miR-296-5p, let-7b-3p and let-7d-3p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In one embodiment, the placenta-derived adherent cell exosomes described herein comprise miR-92 and additionally one or more miRNA selected from the group of miR-133b, miR-422a, miR-16-5p, let-7a, miR-142-3p, miR-451, miR-223-3p, miR-630, miR-296-5p, let-7b-3p and let-7d-3p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In one embodiment, the placenta-derived adherent cell exosomes described herein comprise miR-142-3p and additionally one or more miRNA selected from the group of miR-133b, miR-422a, miR-16-5p, let-7a, miR-92, miR-451, miR-223-3p, miR-630, miR-296-5p, let-7b-3p and let-7d-3p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In one embodiment, the placenta-derived adherent cell exosomes described herein comprise miR-451 and additionally one or more miRNA selected from the group of miR-133b, miR-422a, miR-16-5p, let-7a, miR-92, miR-142-3p, miR-223-3p, miR-630, miR-296-5p, let-7b-3p and let-7d-3p at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In one embodiment, the placenta-derived adherent cell exosomes described herein comprise miR-223-3p and additionally one or more miRNA selected from the group of miR-133b, miR-422a, miR-16-5p, let-7a, miR-92, miR-142-3p, miR-451, miR-630, miR-296-5p, let-7b-3p and lct-7d-3p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In one embodiment, the placenta-derived adherent cell exosomes described herein comprise miR-630 and additionally one or more miRNA selected from the group of miR-133b, miR-422a, miR-16-5p, let-7a, miR-92, miR-142-3p, miR-451, miR-223-3p, miR-296-5p, let-7b-3p and let-7d-3p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In one embodiment, the placenta-derived adherent cell exosomes described herein comprise miR-296-5p and additionally one or more miRNA selected from the group of miR-133b, miR-422a, miR-16-5p, let-7a, miR-92, miR-142-3p, miR-451, miR-223-3p, miR-630, let-7b-3p and let-7d-3p at a level at least two-fold higher as compared to exosomes from chorionic villi mesenchymal stem cells (e.g., the cho-rionic villi mesenchymal stem cells described in Salomon et al., 2013, PLOS ONE, 8:7, e68451) when the exosomes and the cells from which they are derived are treated by like methods.

In one embodiment, the placenta-derived adherent cell exosomes described herein comprise let-7b-3p and additionally one or more miRNA selected from the group of miR-133b, miR-422a, miR-16-5p, let-7a, miR-92, miR-142-3p, miR-451, miR-223-3p, miR-630, miR-296-5p and let-7d-3p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In one embodiment, the placenta-derived adherent cell exosomes described herein comprise let-7d-3p and additionally one or more miRNA selected from the group of miR-133b, miR-422a, miR-16-5p, let-7a, miR-92, miR-142-3p, miR-451, miR-223-3p, miR-630, miR-296-5p and let-7b-3p at a level at least two-fold higher as compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like methods.

In another embodiment, the placenta-derived adherent cell exosomes described herein comprise miR-133b, miR-422a, miR-16-5p, let-7a, miR-92, miR-142-3p, miR-451, miR-223-3p, miR-630, miR-296-5p, let-7b-3p and let-7d-3p or a combination of any of the foregoing at a level at least two-fold higher when compared to exosomes from chorionic villi mesenchymal stem cells (e.g., the chorionic villi mesenchymal stem cells described in Salomon et al., 2013, PLOS ONE, 8:7, e68451) when the exosomes and the cells from which they are derived are treated by like conditions.

5.1.1.3. Angiogenic Proteins

In certain embodiments, the placenta-derived adherent cell exosomes described herein contain one or more proteins that promote angiogenesis. Methods of detecting angiogenic protein levels are well known in the art, e.g., using an ELISA-based method, for example, AngioSecretome Milliplex (Millipore). In specific embodiments, the presence and relative levels of angiogenic proteins associated with the placenta-derived adherent cell exosomes described herein is determined by the method described in Section 6.2.4.3, infra.

In one embodiment, the placenta-derived adherent cell exosomes described herein contain one or more angiogenic proteins selected from the group of Endoglin, Leptin, Angiopoietin-2, G-CSF, Follistatin, FGF-2, HGF, VEGF-A, IL-8 and EGF. In another embodiment, the placenta-derived adherent cell exosomes described herein contain one or more angiogenic proteins selected from the group of Endoglin, Leptin, Angiopoietin-2, G-CSF, Follistatin, FGF-2, HGF, VEGF-A, IL-8 and EGF at a level higher than culture medium lacking exosomes. In another embodiment, said angiogenic proteins are present in culture medium at a concentration of greater than 10 pg/ml, 50 pg/ml, 100 pg/ml, 500 pg/ml, 1,000 pg/ml, 2,000 pg/ml, 4,000 pg/ml, 6,000 pg/ml, 8,000 pg/ml, 10,000 pg/ml, 12,000 pg/ml, 14,000 pg/ml, 16.000 pg/ml, 18,000 pg/ml, 20,000 pg/ml, 25,000 pg/ml, 30,000 pg/ml, 35,000 pg/ml, 40,000 pg/ml, 45,000 pg/ml, or 50,000 pg/ml or higher. In another embodiment said angiogenic proteins are present in culture medium at a concentration of 10 pg/ml to 50 pg/ml, 50 pg/ml to 100 pg/ml, 100 pg/ml to 500 pg/ml, 500 pg/ml to 1,000 pg/ml, 1,000 pg/ml to 2,000 pg/ml, 2,000 pg/ml to 4,000 pg/ml, 4,000 pg/ml to 6,000 pg/ml, 6,000 pg/ml to 8,000 pg/ml, 8,000 pg/ml to 10.000 pg/ml, 10,000 pg/ml 12,000 pg/ml, 12,000 pg/ml to 14,000 pg/ml, 14,000 pg/ml to 16.000 pg/ml, 16,000 pg/ml to 18,000 pg/ml, 18,000 pg/ml to 20,000 pg/ml, 20,000 pg/ml to 25.000 pg/ml, 25,000 pg/ml to 30,000 pg/ml, 30,000 pg/ml to 35,000 pg/ml, 35,000 pg/ml to 40.000 pg/ml, 40,000 pg/ml 45,000 pg/ml, or 45,000 pg/ml to 50,000 pg/ml.

5.1.2. Exosome Size and Distinguishing Characteristics

In certain embodiments, the placenta-derived adherent cell exosomes described herein are about 50 nm to 150 nm in diameter. In certain embodiments, the placenta-derived adherent cell exosomes described herein are about 70 nm to 150 nm in diameter, about 100 nm to 150 nm in diameter, or about 130 nm to 145 nm in diameter, as determined by methods known in the art (e.g., electron microscopy and Nanoparticle Tracking Assay). In certain embodiments, the placenta-derived adherent cell exosomes described herein can be distinguished from cellular and/or non-cellular debris on the basis of their size. In certain embodiments, the exosomes described herein can be distinguished by their shape, for example, the exosomes described herein are cup-shaped when viewed by imaging techniques known in the art (e.g., electron microscopy).

In certain embodiments, the placenta-derived adherent cell exosomes described herein can be identified on the basis of their molecular composition (e.g., surface marker proteins or miRNA molecules). See Section 5.1.1. In certain embodiments, the placenta-derived adherent cell exosomes described herein can be distinguished from other exosomes (i.e., non-placenta-derived adherent cell exosomes) based their molecular profile (e.g., the surface marker proteins and/or miRNA molecules they comprise). See Section 5.1.1.

5.1.3. Placenta-Derived Adherent Cells

The placenta-derived adherent cell exosomes described herein are derived from placenta-derived adherent cells (e.g., the placenta-derived adherent cells disclosed in U.S. Pat. Nos. 7,468,276; 8,057,788 and 8,202,703, the disclosures of which are hereby incorporated by reference in their entireties).

In a specific embodiment, the placenta-derived adherent cell exosomes described herein are derived from CD34$^-$, CD10$^+$, CD105$^+$ and CD200$^+$ placenta-derived adherent cells.

In another specific embodiment, the placenta-derived adherent cell exosomes described herein are derived from placenta-derived adherent cells that express one or more genes at a level at least two-fold higher than bone marrow-derived mesenchymal stem cells, wherein said genes are selected from the group consisting of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FIJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PJP2, RTN1, SERPINB9, ST3GAL6, ST6GALNAC5, SLC12A8, TCF21, TGFB2, VTN, and ZC3H12A. In another embodiment, the placenta-derived adherent cells from which the exosomes described herein are derived express one or more genes at a level at least two-fold higher than bone marrow-derived mesenchymal stem cells, wherein said one or more genes are one or more of LOVL2, ST3GAL6, ST6GALNAC5, and/or SLC12A8. In another embodiment, the placenta-derived adherent cells from which the exosomes provided herein are derived express one or more genes at a level at least two-fold higher than bone marrow-derived mesenchymal stem cells, wherein said one or more genes are one or more of CPA4, TCF21, VTN, B4GALT6, FLJ10781, and/or NUAK1.

In certain embodiments, the placenta-derived adherent cell exosomes described herein are obtained from placenta-derived adherent cells grown in culture, e.g., placenta-derived adherent cells that have adhered to a tissue culture substrate, or from placenta-derived adherent cells that have administered to a living organism (e.g., a mammal, e.g., a human). In a specific embodiment, the cells are cultured in the presence of serum. In another specific embodiment, the cells are cultured in the absence of serum.

In one embodiment, the placenta-derived adherent cells from which the placenta-derived adherent cell exosomes provided herein are derived are substantially fetal in origin, e.g., the placenta-derived adherent cells are about or at least 90%, 95%, 99% or 100% fetal in origin.

In another embodiment, the placenta-derived adherent cells from which the placenta-derived adherent cell exosomes provided herein are derived are of mixed origin, e.g., the placenta-derived adherent cells are both fetal and maternal in origin.

In certain embodiments, the placenta-derived adherent cells from which the placenta-derived adherent cell exosomes provided herein are derived have been passaged prior to isolation of exosomes from the placenta-derived adherent cells. In a specific embodiment, the placenta-derived adherent cells from which the placenta-derived adherent cell exosomes provided herein are derived have been passaged about or at least 1, 2, 3, 4, 5, 6, 7, 8, 9, 10, 12, 14, 16, 18, or 20 times prior to isolation of exosomes from the placenta-derived adherent cells. In a specific embodiment, the exosomes provided herein are collected from placenta-derived adherent cells that have been cultured in vitro for 6 passages. In certain embodiments, the exosomes provided herein are collected from placenta-derived adherent cells plated at passage 6, and collected from culture supernatant at passage 7.

In certain embodiments, the placenta-derived adherent cells from which the placenta-derived adherent cell exosomes provided herein are derived have been expanded prior to isolation of exosomes from the placenta-derived adherent cells. In a specific embodiment, the placenta-derived adherent cells from which the placenta-derived adherent cell exosomes provided herein are derived have been expanded for 1, 2, 3, 4, 5, 6, 7, 8, 9, 10, 12, 14, 16, 18, 20, 22, 24, 26, 28, 30, 32, 34, 36, 38 or 40 population doublings, or more, prior to isolation of exosomes from the placenta-derived adherent cells.

In a specific embodiment, the placenta-derived adherent cells from which the placenta-derived adherent cell exosomes provided herein are derived are not chorionic villi mesenchymal stem cells and/or do not comprise chorionic villi mesenchymal stem cells, e.g., the placenta-derived adherent cells from which the placenta-derived adherent cell exosomes provided herein are derived are not the chorionic villi mesenchymal stem cells described in Salomon et al., 2013, PLOS ONE, 8:7, e68451. In another embodiment, the source from which the placenta-derived adherent cells are derived does not contain chorionic villi.

5.2. Methods of Isolating Placenta-Derived Adherent Cell Exosomes

5.2.1. Methods of Obtaining Exosomes from Medium

The placenta-derived adherent cell exosomes described herein can be produced from, e.g., the placenta-derived adherent cells described in Section 5.1.3. In certain embodiments, the culture of such placenta-derived adherent cells results in the deposition of exosomes into the culture medium, wherein said exosomes may be isolated from the culture medium using techniques described herein and known in the art. The isolation of placenta-derived adherent cell exosomes described herein may be accomplished based on specific surface marker molecules associated with the placenta-derived adherent cell exosomes, using size filtration, using density-dependent centrifugation, and by using other methods known in the art. In certain embodiments, isolation of the placenta-derived adherent cell exosomes described herein can combine two or more techniques to substantially purify exosome populations from contaminating cellular and non-cellular material present in culture medium.

5.2.1.1. Isolation of Exosomes by Ultracentrifugation

In a specific embodiment, the placenta-derived adherent cell exosomes described herein are separated from other components of cell culture medium using ultracentrifugation. In a specific embodiment, culture medium collected from cultures of placenta-derived adherent cells is isolated and centrifuged at high speed (e.g., 100,000×g) for a time sufficient to separate placenta-derived adherent cell exosomes from cellular and non-cellular materials present in the culture medium. In a specific embodiment, placenta-derived adherent cells are cultured in the presence of serum (e.g., fetal bovine serum) prior to collecting culture medium for the isolation of placenta-derived adherent cell exosomes. In another specific embodiment, placenta-derived adherent cells are cultured in the absence of serum (e.g., fetal bovine serum) prior to collecting culture medium for the isolation of placenta-derived adherent cell exosomes. In one embodiment, culture medium collected from cultures of placenta-derived adherent cells is isolated and centrifuged according to the method of Example 1, infra.

5.2.1.2. Isolation of Exosomes by Fluorescence-Activated Cell Sorting

The placenta-derived adherent cell exosomes described herein can be isolated and/or purified on the basis of containing one or more surface marker proteins and/or on the basis of lacking one or more surface marker proteins. Specifically, the placenta-derived adherent cell exosomes described herein can be substantially isolated from non-placenta-derived adherent cell exosomes, or placenta-derived adherent cell exosomes that do not contain the surface markers of interest. For example, one subpopulation of placenta-derived adherent cell exosomes containing a specific combination of surface markers can be isolated from one or more additional populations of exosomes (e.g., placenta-derived adherent cell exosomes) that contain a unique or substantially different combination of surface markers. Accordingly, the placenta-derived adherent cell exosomes described herein can be isolated and/or purified on the basis of any combination of the surface markers described herein. See Section 5.1.1.

In one embodiment, fluorescence-activated cell sorting (FACS) is used to separate and/or purify the placenta-derived adherent cell exosomes described herein using antibodies specific to cell surface markers present on the exosomes. Methods of using FACS to isolate cells and exosomes are known in the art.

In one embodiment, the method of purifying/isolating the placenta-derived adherent cell exosomes described herein comprises contacting a population of exosomes described herein with a solid substrate (e.g., latex bead) for a time and under conditions sufficient to allow for the creation of a complex between said exosomes and said substrate (e.g., by passive adsorption). In another specific embodiment, a population of exosomes contacted with a solid substrate (e.g., latex beads) for a time and under conditions sufficient to allow for the creation of a complex between said exosomes and said substrate (e.g., by passive adsorption) is separated according to a method described herein (e.g., a FACS method described herein).

In another embodiment, the placenta-derived adherent cell exosomes described herein can be purified and/or isolated using a two-part "sandwich" detection technique. In a particular embodiment, the exosomes in a partially purified or unpurified population are first contacted with a substrate, e.g., a population of beads (e.g., a population of latex beads), that are coated with an antibody specific for a protein that is present on the surface of the placenta-derived adherent cell exosomes described herein. In a specific embodiment, an antibody that specifically recognizes CD63 is used to isolate the placenta-derived adherent cell exosomes described herein using such a method. In another specific embodiment, an antibody that specifically recognizes a member of the MHC class II molecule family is used to isolate the placenta-derived adherent cell exosomes described herein using such a method. After the first contacting step, the exosomes bound to the substrate are contacted by a second molecule specific to a surface marker protein that is present on the surface of the placenta-derived adherent cell exosomes described herein. In a specific embodiment, the surface molecule is a tetraspanin and said antibody is a fluorescently-labeled antibody. In another specific embodiment, the surface molecule is any one of FLOT1, ALIX, ANXA5, TSG101, Annexin V, CD3, CD9, CD10, CD11b, CD13, CD14, CD19, CD29, CD33, CD44, CD46, CD47, CD49b, CD49c, CD55, CD59, CD63, CD73, CD81, CD90, CD98, CD105, CD142, CD147, CD151, CD164, CD166, CD192, HLA-A, HLA-B, HLA-C, HLA-DR, CD11c, CD34, CD49d or CD200.

5.2.1.3. Isolation of Exosomes Using Size-Exclusion Chromatography

The placenta-derived adherent cell exosomes described herein can be isolated and/or purified from common contaminants present in culture medium, including thyroglobulin dimers, thyroglobulin monomers, Immunglobulins (e.g., IgG), bovine serum albumin (BSA), myoglobulin, and uracil (see Section 6.3). In one embodiment, the placenta-derived adherent cell exosomes described herein are distinguished in a sample from common culture medium contaminants (e.g., Thyroglobulin, IgG, BSA, Myoglobulin or Uracil) by eluting from a size-exclusion column (e.g., a TSK Guard SWXL column) in fractions collected at 10 minutes to 11 minutes or 11 minutes to 12 minutes after the beginning of fraction collection when said sample is run on an HPLC at a flow rate of 0.5 mL/min. In specific embodiments, the placenta-derived adherent cell exosomes described herein elute in the first detectable peak of a sample collected from a size-exclusion column (e.g., a TSK Guard SWXL column) after said sample is run on an HPLC at a flow rate of 0.5 mL/min.

The isolation of exosomes can be based on size, e.g., a diameter of about 50-150 nm. Exosome size, therefore, allows for the use of techniques such as high-performance liquid chromatography (HPLC) combined with size-exclusion chromatography to isolate substantially pure populations of exosomes and/or to determine the purity of isolated exosome populations. In particular, exosomes purified and/or isolated by one of the methods described herein can be subsequently purified by HPLC to remove contaminating macromolecules and other undesired contaminants. Methods of using HPLC and size exclusion chromatography to separate mixed populations of molecules are well-known in the art and rely upon semiporous substrates and ion/pH gradients to differentially separate the various components of mixed populations.

In one embodiment, the placenta-derived adherent cell exosomes described herein (e.g., exosomes previously isolated from culture medium) are further purified using a method comprising HPLC (e.g., using an Agilent 1200 Series LC system). In a particular embodiment, said method further comprises using a size-exclusion chromatography column (e.g., TSK Guard SWXL and/or TSK gel G4000, Tosoh Corp.) and a buffer (e.g., 20 mM $K_2PO_4$, 150 mM NaCl, pH 7.2) at a fixed flow rate (e.g., 0.5 ml/min). In a specific embodiment, the placenta-derived adherent cell exosomes described herein have a diameter of 50-150 nm.

5.2.2. In Vivo Antibody Capture

In a particular embodiment, placenta-derived adherent cell exosomes described herein are isolated from a subject (e.g., a mouse or a human) after the introduction of placenta-derived adherent cells or placenta-derived adherent cell exosomes described herein. In one embodiment, a subject (e.g., a mouse) is injected with an antibody specific to a protein contained in or on an exosome described herein, wherein said antibody is coupled to a second high-affinity molecule (e.g., biotin). Said subject (e.g., a mouse) is additionally injected (e.g., injected intravenously, intraperitoneally, or intramuscularly) with placenta-derived adherent cells and/or isolated placenta-derived adherent cells described herein. After a time sufficient for said placenta-derived adherent cells to produce exosomes, blood from the subject (e.g., a mouse) is isolated containing complexes comprising placenta-derived adherent cell exosomes and antibodies specific to an exosome protein as described herein. Said antibody-exosome complexes can be purified by contacting a substrate (e.g., streptavidin) that is specific to the second high-affinity molecule (e.g., biotin) coupled to said antibody, and the resulting antibody-exosome complexes can be further purified according to any of the methods described herein.

5.2.3. Quantification

The exosomes isolated from the placenta-derived adherent cell cultures described herein may be quantified to determine total yield. Methods of quantifying exosome yield are known in the art and include Bradford assay, BCA assay, spectrophotometry (e.g., using a NanoDrop spectrophotometer), direct Enzyme-Linked ImmunoSorbent Assay (e.g., CD63/CD9/CD81 ExoELISA (System Biosciences)), imaging techniques such as Nanoparticle Tracking Analysis (e.g., Nanosight LM10 (Malvern Instruments) or electrical impedence-based measurement such as qNano (IZON)). According to these methods, exosome yields may be determined either as total amount of material isolated (e.g., mass of exosomal material isolated per cell per day) or as the number of individual particles in a defined volume of culture medium (e.g. exosome particles per mL of culture medium).

5.2.4. Yield

The placenta-derived adherent cell exosomes described herein may be isolated in accordance with the methods described herein and their yields may be quantified. In a specific embodiment, the placenta-derived adherent cell exosomes described herein are isolated at a concentration of about 0.5-5.0 mg per liter of culture medium (e.g., culture medium with or without serum). In another specific embodiment, the placenta-derived adherent cell exosomes described herein are isolated at a concentration of about 2-3 mg per liter of culture medium (e.g., culture medium containing serum). In another specific embodiment, the placenta-derived adherent cell exosomes described herein are isolated at a concentration of about 0.5-1.5 mg per liter of culture medium (e.g., culture medium lacking serum).

5.2.5. Storage and Preservation

The placenta-derived adherent cell exosomes described herein can be preserved, that is, placed under conditions that allow for long-term storage, or conditions that inhibit degradation of the exosomes.

In certain embodiments, the placenta-derived adherent cell exosomes described herein can be stored after collection according to a method described above in a composition comprising a buffering agent at an appropriate temperature. In certain embodiments, the placenta-derived adherent cell exosomes described herein are stored frozen, e.g., at about −20° C. or about −80° C.

In certain embodiments, the placenta-derived adherent cell exosomes described herein can be cryopreserved, e.g., in small containers, e.g., ampoules (for example, 2 mL vials). In certain embodiments, the placenta-derived adherent cell exosomes described herein are cryopreserved at a concentration of about 0.1 mg/mL to about 10 mg/mL.

In certain embodiments, the placenta-derived adherent cell exosomes described herein are cryopreserved at a temperature from about −80° C. to about −180° C. Cryopreserved exosomes can be transferred to liquid nitrogen prior to thawing for use. In some embodiments, for example, once the ampoules have reached about −90° C., they are transferred to a liquid nitrogen storage area. Cryopreservation can also be done using a controlled-rate freezer. Cryopreserved exosomes can be thawed at a temperature of about 25° C. to about 40° C. before use.

In certain embodiments, the placenta-derived adherent cell exosomes described herein are stored at temperatures of about 4° C. to about 20° C. for short periods of time (e.g., less than two weeks).

5.3. Compositions

Further provided herein are compositions, e.g., pharmaceutical compositions, comprising the placenta-derived adherent cell exosomes provided herein. See, e.g., Section 5.1. The compositions described herein are useful in the treatment of certain diseases and disorders in subjects (e.g., human subjects) wherein treatment with exosomes is beneficial. See Section 5.4.1.

In certain embodiments, in addition to comprising the placenta-derived adherent cell exosomes provided herein, the compositions (e.g., pharmaceutical compositions) described herein comprise a pharmaceutically acceptable carrier. As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier," as used herein in the context of a pharmaceutically acceptable carrier, refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by J P Remington and A R Gennaro, 1990, 18$^{th}$ Edition.

In certain embodiments, the compositions described herein additionally comprise one or more buffers, e.g., saline, phosphate buffered saline (PBS), Dulbecco's PBS (DPBS), and/or sucrose phosphate glutamate buffer. In other embodiments, the compositions described herein do not comprise buffers. In certain embodiments, the compositions described herein additionally comprise plasmalyte.

In certain embodiments, the compositions described herein additionally comprise one or more salts, e.g., sodium chloride, calcium chloride, sodium phosphate, monosodium glutamate, and aluminum salts (e.g., aluminum hydroxide, aluminum phosphate, alum (potassium aluminum sulfate), or a mixture of such aluminum salts). In other embodiments, the compositions described herein do not comprise salts.

The compositions described herein can be included in a container, pack, or dispenser together with instructions for administration.

The compositions described herein can be stored before use, e.g., the compositions can be stored frozen (e.g., at about −20° C. or at about −80° C.); stored in refrigerated conditions (e.g., at about 4° C.); or stored at room temperature.

5.3.1. Formulations and Routes of Administration

The amount of placenta-derived adherent cell exosomes (see Section 5.1) or a composition described herein (see Section 5.3) which will be effective for a therapeutic use in the treatment and/or prevention of a disease or condition will depend on the nature of the disease, and can be determined by standard clinical techniques. The precise dosage of placenta-derived adherent cell exosomes, or compositions thereof, to be administered to a subject will also depend on the route of administration and the seriousness of the disease or condition to be treated, and should be decided according to the judgment of the practitioner and each subject's circumstances. For example, effective dosages may vary depending upon means of administration, target site, physiological state of the patient (including age, body weight, and health), whether the patient is human or an animal, other medications administered, and whether treatment is prophylactic or therapeutic. Treatment dosages are optimally titrated to optimize safety and efficacy.

Administration of the placenta-derived adherent cell exosomes described herein (see Section 5.1), or compositions thereof (see Section 5.3) can be done via various routes known in the art. In certain embodiments, the placenta-derived adherent cell exosomes described herein, or compositions thereof are administered by local, systemic, subcutaneous, parenteral, intravenous, intramuscular, topical, oral, intradermal, transdermal, or intranasal, administration. In a specific embodiment, said administration is via intravenous injection. In a specific embodiment, said administration is via subcutaneous injection. In a specific embodiment, said administration is topical. In another specific embodiment, the placenta-derived adherent cell exosomes, or compositions thereof, are administered in a formulation comprising an extracellular matrix. In another specific embodiment, the placenta-derived adherent cell exosomes, or compositions thereof, are administered in combination with one or more additional delivery device, e.g., a stent. In another specific embodiment, the placenta-derived adherent cell exosomes, or compositions thereof, are administered locally, e.g., at or around the site of an area to be treated with said exosomes or compositions, such as hypoxic tissue (e.g., in treatment of ischemic diseases) or draining lymph nodes.

5.4. Methods of Use

5.4.1. Treatment of Diseases that Benefit from Angiogenesis

The placenta-derived adherent cell exosomes described herein (see Section 5.1), and compositions thereof (see Section 5.3), promote angiogenesis, and, therefore can be used to treat diseases and disorders that benefit from angiogenesis. Accordingly, provided herein are methods of using the placenta-derived adherent cell exosomes described herein, or compositions thereof, to promote angiogenesis in a subject in need thereof. As used herein, the term "treat" encompasses the cure of, remediation of, improvement of, lessening of the severity of, or reduction in the time course of, a disease, disorder or condition, or any parameter or symptom thereof in a subject. In a specific embodiment, the subject treated in accordance with the methods provided herein is a mammal, e.g., a human.

In one embodiment, provided herein are methods of inducing vascularization or angiogenesis in a subject, said methods comprising administering to the subject the placenta-derived adherent cell exosomes provided herein, or a composition thereof. Accordingly, the methods provided herein can be used to treat diseases and disorders in a subject that that benefit from increased angiogenesis/vascularization. Examples of such diseases/conditions that benefit from increased angiogenesis, and therefore can be treated with the placenta-derived adherent cell exosomes and compositions described herein included, without limitation, myocardial infarction, congestive heart failure, peripheral artery disease, critical limb ischemia, peripheral vascular disease, hypoplastic left heart syndrome, diabetic foot ulcer, venous ulcer, or arterial ulcer.

In one embodiment, provided herein are methods of treating a subject having a disruption of blood flow, e.g., in the peripheral vasculature, said methods comprising administering to the subject the placenta-derived adherent cell exosomes provided herein, or a composition thereof. In a specific embodiment, the methods provided herein comprise treating a subject having ischemia with the placenta-derived adherent cell exosomes provided herein, or a composition thereof. In certain embodiments, the ischemia is peripheral arterial disease (PAD), e.g., is critical limb ischemia (CLI). In certain other embodiments, the ischemia is peripheral vascular disease (PVD), peripheral arterial disease, ischemic vascular disease, ischemic heart disease, or ischemic renal disease.

5.4.2. Patient Populations

In certain embodiments, the placenta-derived adherent cell exosomes described herein (see Section 5.1) are administered to a subject in need of therapy for any of the diseases or conditions described herein (see Section 5.4.1). In another embodiment, a composition described herein (see Section 5.3) is administered to a subject in need of therapy for any of the diseases or conditions described herein. In certain embodiments said subject is a human.

In a specific embodiment, the placenta-derived adherent cell exosomes or compositions described herein are administered to a subject (e.g., a human) in need of a therapy to increase angiogensis and/or vascularization.

5.5. Kits

Provided herein is a pharmaceutical pack or kit comprising one or more containers filled with one or more of the ingredients of the pharmaceutical compositions described herein, i.e., compositions comprising the placenta-derived adherent cell exosomes described herein. Optionally associated with such container(s) can be a notice in the form prescribed by a governmental agency regulating the manufacture, use or sale of pharmaceuticals or biological products, which notice reflects approval by the agency of manufacture, use or sale for human administration.

The kits described herein can be used in the above methods (see Section 5.4). The compositions described herein can be prepared in a form that is easily administrable to an individual. For example, the composition can be contained within a container that is suitable for medical use. Such a container can be, for example, a sterile plastic bag, flask, jar, or other container from which the compositions can be easily dispensed. For example, the container can be a blood bag or other plastic, medically-acceptable bag suitable for the intravenous administration of a liquid to a recipient.

5.6. Delivery Systems

The placenta-derived adherent cell exosomes described herein, and compositions thereof, can be loaded with agent(s), e.g., pharmaceutical agent(s), exogenous to the exosomes. Such exosomes and compositions thereof can, for example, be taken up into target cells, e.g., cells other than the cell type from which the exosomes were obtained, and thereby deliver the exogenous agent(s), e.g., pharmaceutical agent(s), into the target cells.

Accordingly, provided herein are methods of loading placenta-derived adherent cell exosomes with exogenous agents, for example, pharmaceutical agents. In one embodiment, such a method comprises incubating a placenta-derived adherent cell exosome and an exogenous agent, e.g., pharmaceutical agent, for example incubating at room temperature, with or without saponin permeabilization, freeze/thaw cycles, sonication, or extrusion. See, e.g., Haney et al., 2015, *J. Controlled Release* 207:18-30, which is incorporated herein by reference. In certain embodiments, the exogenous agent, e.g., pharmaceutical agent, is loaded into the placenta-derived adherent cell exosome by incubation at room temperature. In certain embodiments, the exogenous agent, e.g., pharmaceutical agent, is loaded into the placenta-derived adherent cell exosome by incubation at 10° C., 15° C., 18° C., 20° C., 22° C., 25° C., 28° C., 30° C., 35° C., or 40° C. In specific embodiments, incubation, e.g., incubation at room temperature, is performed without saponin permeabilization of the placenta-derived adherent cell exosome. In specific embodiments, incubation, e.g., incubation at room temperature, is performed with saponin permeabilization of the placenta-derived adherent cell exosome. In certain embodiments, the exogenous agent, e.g., pharmaceutical agent, is loaded into the placenta-derived adherent cell exosome by freeze/thaw cycles, for example, 1, 2, 3, 4, 5, or more freeze/thaw cycles. In certain embodiments, the exogenous agent, e.g., pharmaceutical agent, is loaded into the placenta-derived adherent cell exosome by sonication. In certain embodiments, the exogenous agent, e.g., pharmaceutical agent, is loaded into the placenta-derived adherent cell exosome by extrusion. In certain embodiments, the exogenous agent, e.g., pharmaceutical agent, is loaded into the placenta-derived adherent cell exosome by electroporation. In specific embodiments, methods of loading exosomes with exogenous agents, for example, pharmaceutical agents, comprise any combination of the above.

In certain embodiments, the exogenous agent, e.g., pharmaceutical agent, incorporated into the placenta-derived adherent cell placenta-derived adherent cell exosomes described herein comprises a polypeptide. In specific embodiments, the exogenous agent, e.g., pharmaceutical agent is a binding agent, for example, an antibody, such as, e.g., a human, humanized, or chimeric antibody, or antigen-binding fragment thereof. In particular embodiments, the antibody is a monospecific, bispecific or multispecific antibody, or antigen-binding fragment thereof. In yet other particular embodiments, the antibody or antigen binding fragment thereof is a single-chain antibody or a Fab fragment. In specific embodiments, the antibody or antigen-binding fragment thereof would not internalize into a target cell without the aid of the placenta-derived adherent cell exosome.

In certain embodiments, the exogenous agent, e.g., pharmaceutical agent, loaded into the placenta-derived adherent cell exosomes described herein comprises one or more nucleic acids. In specific embodiments, the one or more nucleic acids comprise a siRNA or an miRNA.

In certain embodiments, the exogenous agent, e.g., pharmaceutical agent, loaded into the placenta-derived adherent cell exosomes described herein comprises one or more gene-modifying components. In specific embodiments, the one or more gene-modifying components comprise a CRISPR-Cas system. In more specific embodiments, the CRISPR-Cas system comprises a guide RNA. In more specific embodiments, the CRISPR-Cas system comprises an endonuclease. In more specific embodiments, the CRISPR-Cas system comprises a guide RNA and an endonuclease. In more specific embodiments, the CRISPR-Cas system comprises Cas9. In more specific embodiments, the CRISPR-Cas system comprises Cpf1. In specific embodiments, the one or more gene-modifying components comprise a zinc finger nuclease. In specific embodiments, the one or more gene-modifying components comprise a transcription activator-like effector nuclease (TALEN) system.

In another embodiment, provided herein are methods of delivering an exogenous agent, e.g., a pharmaceutical agent, to a target cell, wherein the exogenous agent is loaded into a placenta-derived adherent cell exosome. In certain embodiments, the target cell is a cell other than the cell type from which the exosome was obtained. In certain embodiments, the exogenous agent, e.g., pharmaceutical agent, loaded into the placenta-derived adherent cell exosomes described herein comprises a polypeptide. In specific embodiments, the exogenous agent, e.g., pharmaceutical agent is a binding agent, for example, an antibody, such as, e.g., a human, humanized, or chimeric antibody, or antigen-binding fragment thereof. In particular embodiments, the antibody is a monospecific, bispecific or multispecific antibody, or antigen-binding fragment thereof. In yet other particular embodiments, the antibody or antigen binding fragment thereof is a single-chain antibody or a Fab fragment. In specific embodiments, the antibody or antigen-binding fragment thereof would not internalize into a target cell, e.g., a cell other than the cell type from which the exosomes were obtained, without the aid of the placenta-derived adherent cell exosome. In certain embodiments, the exogenous agent, e.g., pharmaceutical agent, loaded into the placenta-derived adherent cell exosomes described herein comprises one or more nucleic acids. In specific embodiments, the one or more nucleic acids comprise a siRNA. In certain embodiments, the exogenous agent, e.g., pharmaceutical agent, loaded into the placenta-derived adherent cell exosomes described herein comprises one or more gene-modifying components. In specific embodiments, the one or more gene-modifying components comprise a CRISPR-Cas system. In more specific embodiments, the CRISPR-Cas system comprises a guide RNA. In more specific embodiments, the CRISPR-Cas system comprises an endonuclease. In more specific embodiments, the CRISPR-Cas system comprises a guide RNA and an endonuclease. In more specific embodiments, the CRISPR-Cas system comprises Cas9. In more specific embodiments, the CRISPR-Cas system comprises Cpf1. In specific embodiments, the one or more gene-modifying components comprise a zinc finger nuclease. In specific embodiments, the one or more gene-modifying components comprise a transcription activator-like effector nuclease (TALEN) system.

Provided herein are methods of administering to an individual placenta-derived adherent cell exosomes comprising exogenous agents, for example, pharmaceutical agents, to a subject, e.g., a human. In certain embodiments, the exogenous agent, e.g., pharmaceutical agent, comprises a polypeptide. In specific embodiments, the exogenous agent, e.g., pharmaceutical agent, is a binding agent, for example, an antibody, such as, e.g., a human, humanized, or chimeric antibody, or antigen-binding fragment thereof. In particular embodiments, the antibody is a monospecific, bispecific or multispecific antibody, or antigen-binding fragment thereof. In yet other particular embodiments, the antibody or antigen binding fragment thereof is a single-chain antibody or a Fab fragment. In specific embodiments, the antibody or antigen-binding fragment thereof would not internalize into a target cell without the aid of the placenta-derived adherent cell exosome. In certain embodiments, the exogenous agent, e.g., pharmaceutical agent, loaded into the placenta-derived adherent cell exosomes described herein comprises one or more nucleic acids. In specific embodiments, the one or more nucleic acids comprise an siRNA or an miRNA. In certain embodiments, the exogenous agent, e.g., pharmaceutical agent, loaded into the placenta-derived adherent cell exosomes described herein comprises one or more gene-modifying components. In specific embodiments, the one or more gene-modifying components comprise a CRISPR-Cas system. In more specific embodiments, the CRISPR-Cas system comprises a guide RNA. In more specific embodiments, the CRISPR-Cas system comprises an endonuclease. In more specific embodiments, the CRISPR-Cas system comprises a guide RNA and an endonuclease. In more specific embodiments, the CRISPR-Cas system comprises Cas9. In more specific embodiments, the CRISPR-Cas system comprises Cpf1. In specific embodiments, the one or more gene-modifying components comprise a zinc finger nuclease. In specific embodiments, the one or more gene-modifying components comprise a transcription activator-like effector nuclease (TALEN) system.

Also provided herein are compositions comprising placenta-derived adherent cell exosomes loaded with one or more exogenous agents, for example, pharmaceutical agents. In certain embodiments, the exogenous agent, e.g., pharmaceutical agent, incorporated into the placenta-derived adherent cell exosomes described herein comprises a polypeptide. In specific embodiments, the exogenous agent, e.g., pharmaceutical agent is a binding agent, for example, an antibody, such as, e.g., a human, humanized, or chimeric antibody, or antigen-binding fragment thereof. In particular embodiments, the antibody is a monospecific, bispecific or multispecific antibody, or antigen-binding fragment thereof. In yet other particular embodiments, the antibody or antigen binding fragment thereof is a single-chain antibody or a Fab fragment. In specific embodiments, the antibody or antigen-binding fragment thereof would not internalize into a target cell without the aid of the placenta-derived adherent cell exosome. In certain embodiments, the exogenous agent, e.g., pharmaceutical agent, loaded into the placenta-derived adherent cell exosomes described herein comprises one or more nucleic acids. In specific embodiments, the one or more nucleic acids comprise an siRNA or an miRNA. In certain embodiments, the exogenous agent, e.g., pharmaceutical agent, loaded into the placenta-derived adherent cell exosomes described herein comprises one or more gene-modifying components. In specific embodiments, the one or more gene-modifying components comprise a CRISPR-Cas system. In more specific embodiments, the CRISPR-Cas system comprises a guide RNA. In more specific embodiments, the CRISPR-Cas system comprises an endonuclease. In more specific embodiments, the CRISPR-Cas system comprises a guide RNA and an endonuclease. In more specific embodiments, the CRISPR-Cas system comprises Cas9. In more specific embodiments, the CRISPR-Cas system comprises Cpf1. In specific embodiments, the one or more gene-modifying components comprise a zinc finger nuclease. In specific embodiments, the one or more gene-modifying components comprise a transcription activator-like effector nuclease (TALEN) system.

6. EXAMPLES

6.1. Example 1: Methods of Isolating Exosomes

Placenta-derived adherent cell exosomes were isolated from $CD10^+$, $CD200^+$, $CD105^+$, $CD34^-$ placenta-derived adherent cell cultures according to the following methods:

Fetal bovine serum (FBS) was depleted of contaminating bovine exosomes by ultracentrifugation at 10,000×g for 1 hour, then at 100,000×g for 18 hours at 4° C. The resulting supernatant was filtered through a 0.2 µm filter prior to storage and use. Exosome-depleted FBS was mixed with Dulbecco's Modified Eagle's Medium (DMEM) for 24 hours to produce growth medium. Growth medium was warmed to 37° C. and placenta-derived adherent cells were plated at a density of 300-1,000 cells/cm$^2$ and cultured for 3 days or until 80% confluent in a cell culture platform device (Corning CELLSTACK 10-Tray with CELLBIND coating). Placenta-derived adherent cell exosomes were plated at passage six, and culture supernatant was collected at passage seven. The placental source of the placenta-derived adherent cells used to isolate the exosomes described herein did not include chorionic villi, thus the placenta-derived adherent cells used to produce placenta-derived adherent cell exosomes did not include chorionic villi mesenchymal stem cells.

After the removal of culture supernatant, the cell culture monolayer was washed with PBS and replenished with serum-free medium (DMEM and 1× glutamine). After 48 hours, the serum-free culture supernatant was collected and subjected to exosome enrichment and isolation procedure as described below. The resulting cell monolayer was harvested for cell count, exosome yield comparison and comparison studies.

Supernatant from confluent serum-containing and serum-free cultures was collected and centrifuged in 500 mL tubes at 400×g for 5-15 minutes at 4° C. Centrifuged supernatant was then transferred to new 500 mL tubes and centrifuged at 3000×g for 20-60 minutes at 4° C. Supernatant was then transferred to appropriate ultracentrifuge tubes and centrifuged at 100,000×g for 60 minutes at 4° C. A small aliquot of the resulting exosome-depleted supernatant was saved for further analysis, and the remainder was discarded. The pellet, containing exosomes, was resuspended in PBS or injectable saline and ultracentrifugation was repeated. The supernatant was discarded and the resulting pellet was re-suspended in PBS or injectable saline, and analyzed according to the examples described below. The resuspended pellets are referred to as "Growth Exosomes" when isolated from cultures containing FBS, or "Serum-Free Exosomes" when isolated from cultures lacking FBS.

The isolated exosome compositions were aliquoted in 2 mL cryo vials and stored at −20 to −80° C.

6.2. Example 2: Confirmation of Placenta-Derived Adherent Cell Exosomes

The results presented herein demonstrate that the non-cellular materials isolated from cell culture supernatants in Example 1 are exosomes.

6.2.1. Detection Using Exosomal Marker Antibody Array

Figure 1:
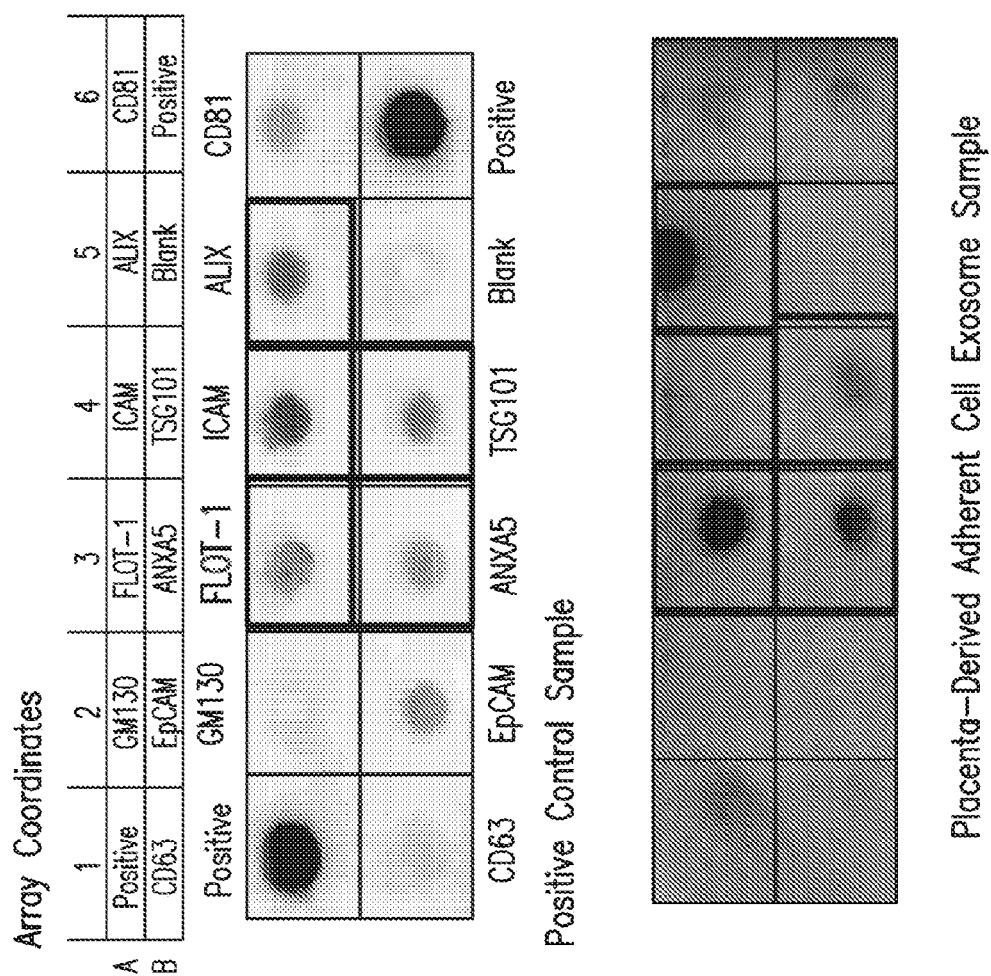

Placenta-derived adherent cell exosomes were isolated as in Section 6.1. Four hundred micrograms of isolated material was analyzed using Exo-Check™ exosome antibody array (System Biosciences) according to the manufacturer's protocol. Exosome lysates were incubated overnight on the antibody array and the sample was imaged using a Kodak Gel-Logic system and developed after a 2 minute luminescence exposure. As shown in FIG. 1 (bottom) placenta-derived adherent cell exosome material resulted in detectable signal for the four markers FLOT-1, ALIX, ANXA5 and TSG101. The use of a positive control sample, included as part of the array kit, resulted in a detectable signal for these markers as well (FIG. 1 top).

Figures 2A, 2B:
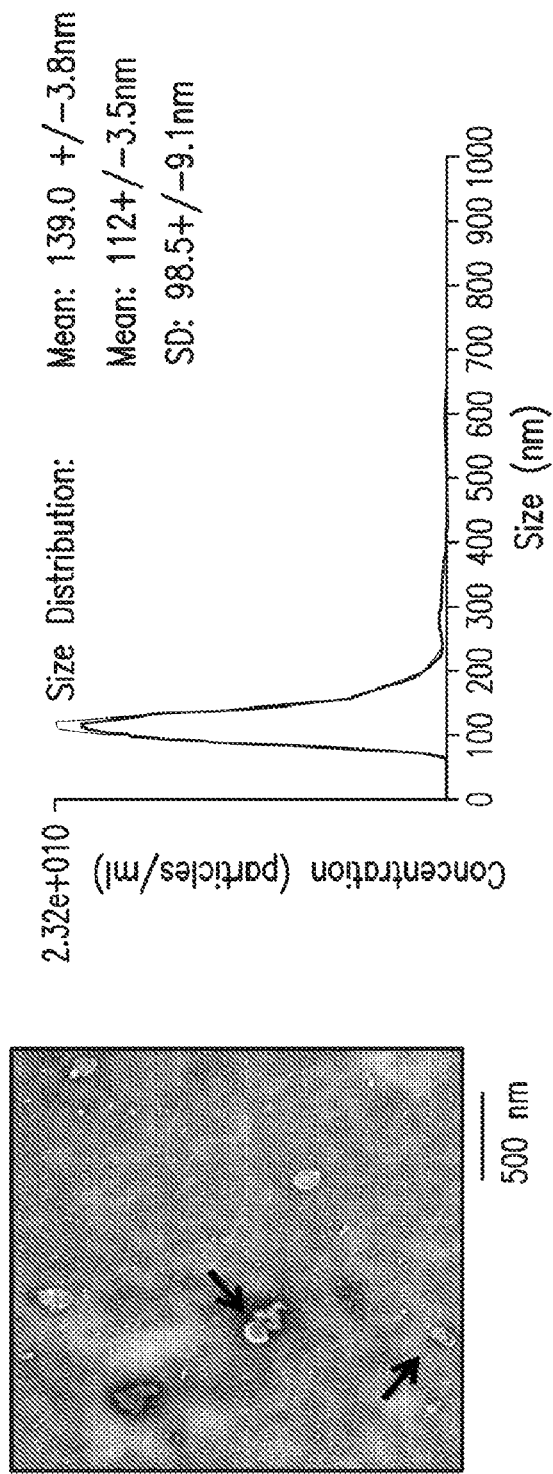

6.2.2. Shape and Size Characteristics of Placenta-Derived Adherent Cell Exosome Samples Isolated exosomes were negative stained and imaged using transmission electron microscopy (TEM) (FIG. 2A) and were found to exist as discrete bodies~100 nm in diameter, often in a cup-like shape (arrows), both characteristics of exosomes. The purified exosomes were further analyzed by nanoparticle tracking analysis (NTA) to determine the size distribution of the isolated population. As shown in FIG. 2B, placenta-derived adherent cell exosomes were an average size of 139 nm, consistent with the known size of exosomes isolated from other cell types.

The morphological characteristics and identified protein markers demonstrated that the material isolated from placenta-derived adherent cells using the above methods are exosomes.

6.3. Example 3: Purification of Placenta-Derived Adherent Cell Exosomes

Figure 3A:
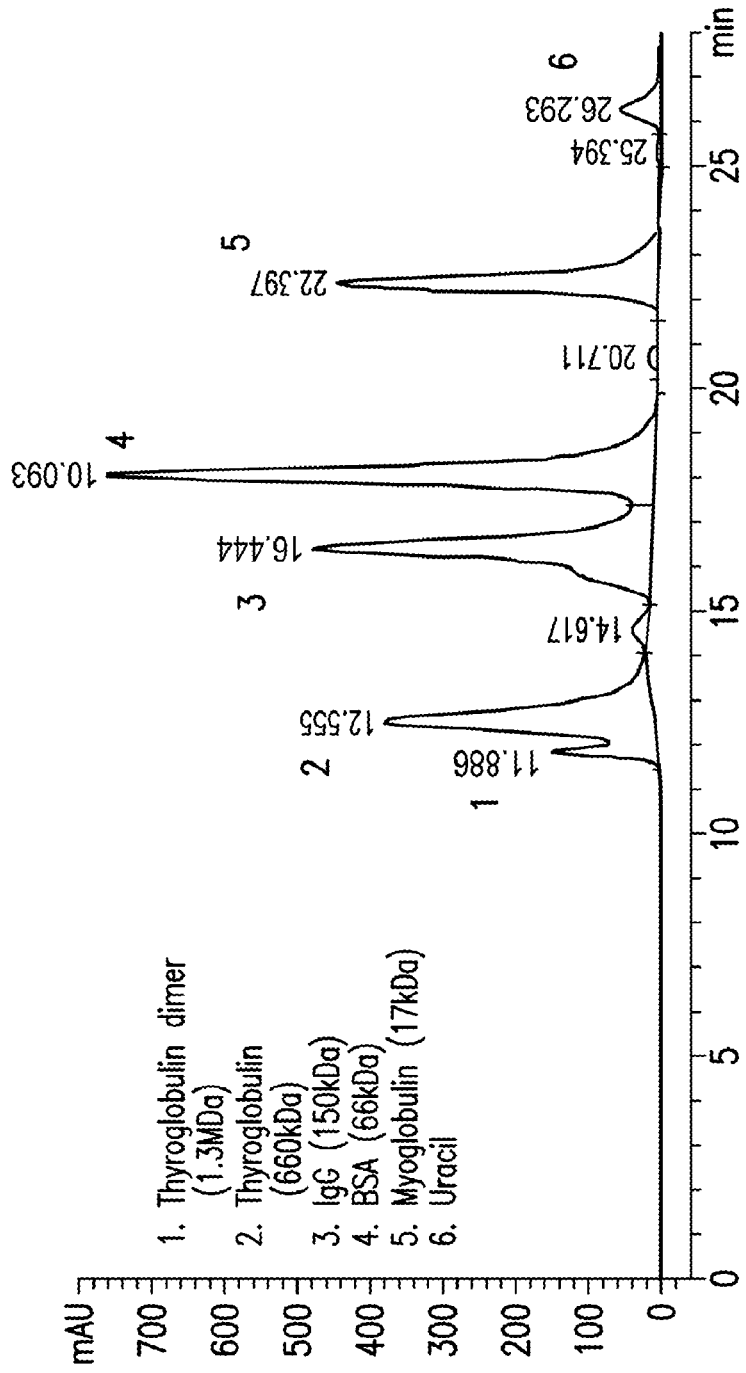

6.3.1. Exosome Purification by Size-Exclusion High-Performance Liquid Chromatography Placenta-derived adherent cell exosomes were isolated as in Section 6.1 and further analyzed by size-exclusion high-performance liquid chromatography (SE-HPLC). Elution profiles of exosomes from chorionic villi mesenchymal stem cells (MSCs) were compared to exosomes obtained from serum-containing ("Growth Supernatant") and serum-free ("Serum Free Supernatant) placenta-derived adherent cell cultures. Elution profiles of exosome preparations (FIGS. 3B-D, arrows) were analyzed in comparison to the elution peaks of known culture medium contaminants (FIG. 3A).

Figure 3B:
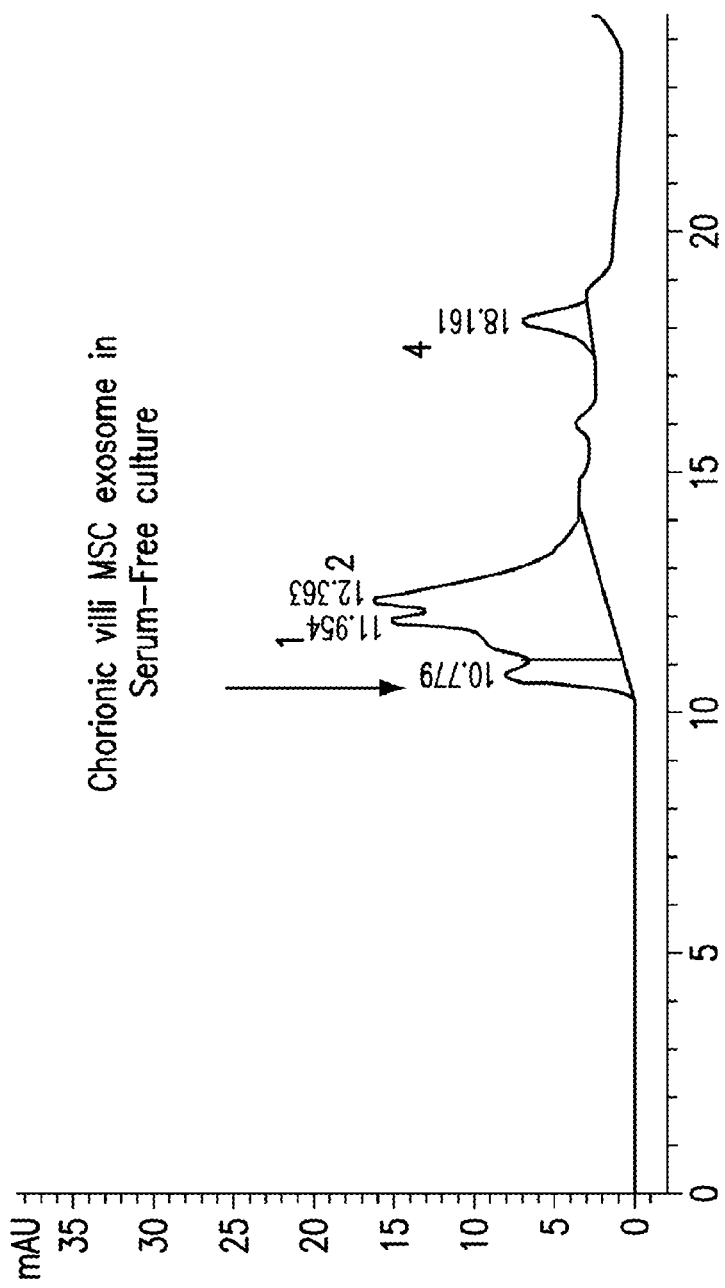
Figure 3C:
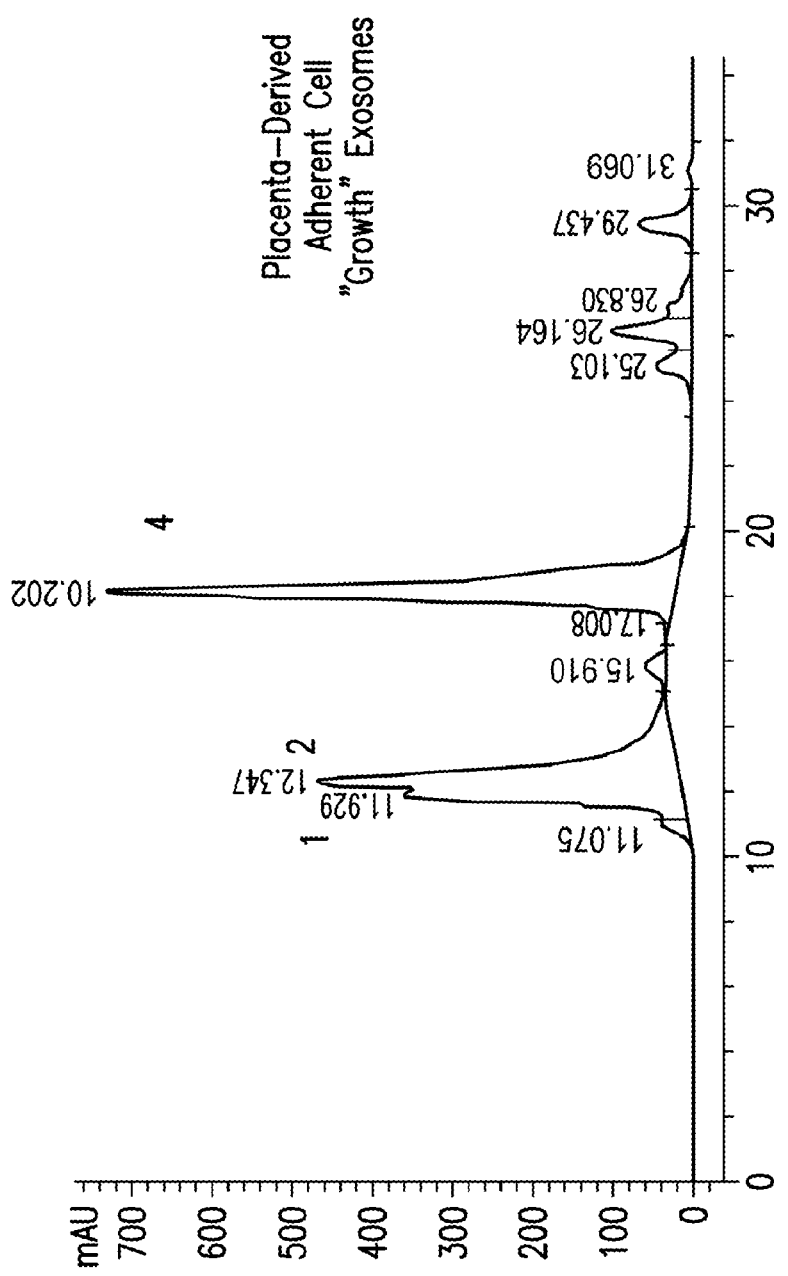
Figure 3D:
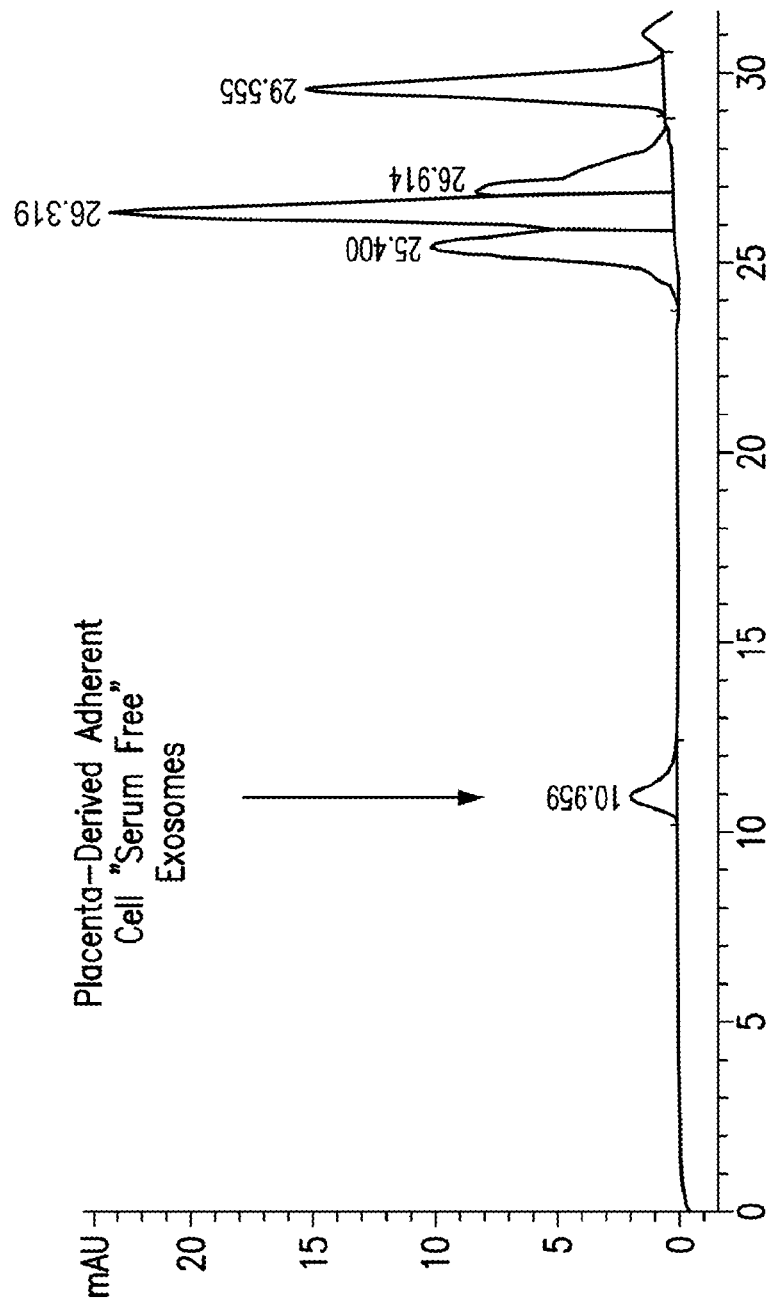

Chorionic villi MSC exosomes contained detectable levels of the contaminants Thyroglobulin and BSA (FIG. 3B). Growth Supernatant placenta-derived adherent cell exosomes also contained detectable levels of Thyroglobulin and BSA (FIG. 3C), while Serum Free Supernatant placenta-derived adherent cell exosomes contained no detectable levels of any of such contaminants (FIG. 3D). Elution profiles of exosomes isolated from either Growth Supernatant or Serum Free cultures were characterized by a peak consistent with that of the positive control exosomes. In the case of Serum Free culture exosomes, the elution profile was present as a single species in the predicted exosome elution fraction (FIG. 3D). These results further demonstrate that the isolated placenta-derived adherent cell microvesicles are exosomes, and that exosomes isolated from cells grown in serum-free conditions lack typical contaminants as compared to exosomes prepared from cells grown in the presence of FBS.

6.4. Example 4: Placenta-Derived Adherent Cell Exosome Molecular Markers

In the present study, FACS was used to examine which of a panel of cell surface markers are contained on the surface of exosomes, and which surface markers are unique to placenta-derived adherent cell exosomes as compared to exosomes derived from other cell types.

In addition to surface marker proteins, it is known that exosomes may contain small nucleic acids, including miRNAs. The composition of miRNAs contained within exosomes may vary between cell types from which exosomes were derived, and the presence and abundance of miRNAs can be determined by methods known in the art, including real-time PCR (RT-PCR). In this study, miRNA content of placenta-derived adherent cell exosomes was examined and compared to exosomes derived from chorionic villi mesenchymal stem cells.

6.4.1. Placenta-Derived Adherent Cell Exosome Surface Markers

Placenta-derived adherent cell exosomes isolated as in Section 6.1 were analyzed by FACS, and the composition of surface markers was compared to exosomes isolated from either chorionic villi MSCs or pre-adipocyte MSCs. The exosomes from these three cell types were determined to differentially contain several surface markers (Table 1). Using FACS analysis, exosomes from placenta-derived adherent cells were found to contain a number of markers unique or enriched in these exosomes as compared to exosomes from chorionic villi MSCs or pre-adipocyte MSCs. As compared to exosomes isolated from chorionic villi MSCs or pre-adipocyte MSCs, placenta-derived adherent cell exosomes contained CD10 and CD55, both of which were absent in both mesenchymal stem cell exosome populations. Placenta-derived adherent cell exosomes also contained a higher level of CD49c, CD82, CD90, and CD142, e.g., a 0.5 to 1 log higher level, as compared to the two mesenchymal stem cell exosome populations (Table 1). Conversely, the placenta-derived adherent cell exosomes contained a lower level of CD164, e.g., a 0.5 to 1 log lower level, as compared to the two mesenchymal stem cell exosome populations (Table 1). Placenta-derived mesenchymal stem cell exosomes also contained detectable levels of CD295, which was not detected on pre-adipocyte MSC exosomes (not shown). As shown in Table 1, the number of "+" symbols in each entry is correlated with the level of the indicated markers, whereas "−" symbols represent no detectable levels of the indicated marker.

TABLE 1

Surface antigens of placenta-derived adherent cell exosomes compared to pre-adipocyte MSC exosomes and chorionic villi MSC exosomes

| Antigen | Placenta-Derived Adherent Cell Exosomes | Pre-Adipocyte MSC Exosome | Placental MSC Exosome |
|---|---|---|---|
| CD9 | ++ | ++ | ++ |
| CD10 | + | − | − |
| CD13 | ++ | ++ | ++ |
| CD29 | ++ | ++ | ++ |
| CD44 | + | + | ++ |
| CD49b | + | +/− | + |
| CTD49c | ++ | − | + |
| CD55 | + | − | − |
| CD59 | ++ | ++ | ++ |
| CD63 | ++ | ++ | ++ |
| CD73 | ++ | + | ++ |
| CD81 | +++ | +++ | +++ |
| CD82 | ++ | + | + |
| CD90 | ++ | + | + |
| CD98 | + | + | + |
| CD105 | + | +/− | + |
| CD141 | + | + | − |
| CD142 | ++ | + | + |
| CD151 | ++ | ++ | ++ |
| CD164 | + | ++ | ++ |
| CD200 | + | + | + |

6.4.2. Placenta-Derived Adherent Cell Exosome miRNA Markers

6.4.2.1. Placenta-Derived Adherent Cell Exosomes and Chorionic Villi Mesenchymal Stem Cell Exosomes Differ in their miRNA Content Placenta-derived adherent cell exosomes were isolated using the Exoquick™ precipitation method according to the manufacturer's protocol (System Biosciences). Culture supernatant was centrifuged for 15 minutes at 3000×g, and the resulting pellet was discarded. Two milliliters of the resulting supernatant was added to 10 ml tissue culture supernatant and mixed by inversion. The resulting mixture was incubated at 4° C. overnight. After incubation, the mixture was centrifuged at 1500×g for 30 minutes, the supernatant was discarded and the pellet was isolated. The remaining liquid was removed by aspiration after centrifuging for additional 5 minutes at 1500×g. The pellet was reconstituted in 200 ul PBS.

Isolated placenta-derived adherent cell exosomes and chorionic villi MSC exosomes (Salomon et al., 2013, PLOS ONE, 8:7, e68451) were lysed and RNA was isolated using Ambion's mirVana miRNA isolation kit (Cat #1566) according to the manufacturer's instructions. In brief, exosomes were lysed with Lysis/Binding Buffer (supplemented with miRNA Homogenate Additive) on ice for 10 minutes, RNA was isolated using acid-phenol:chloroform extraction, and precipitated with ethanol washes. Fifty nanograms of purified RNA was reverse transcribed and probe sets for 17 miRNAs and the control RNA RNU44 were used to amplify the samples according to the TaqMan® qPCR system (Life Technologies). Ct values were calculated for each sample.

Figure 4A:
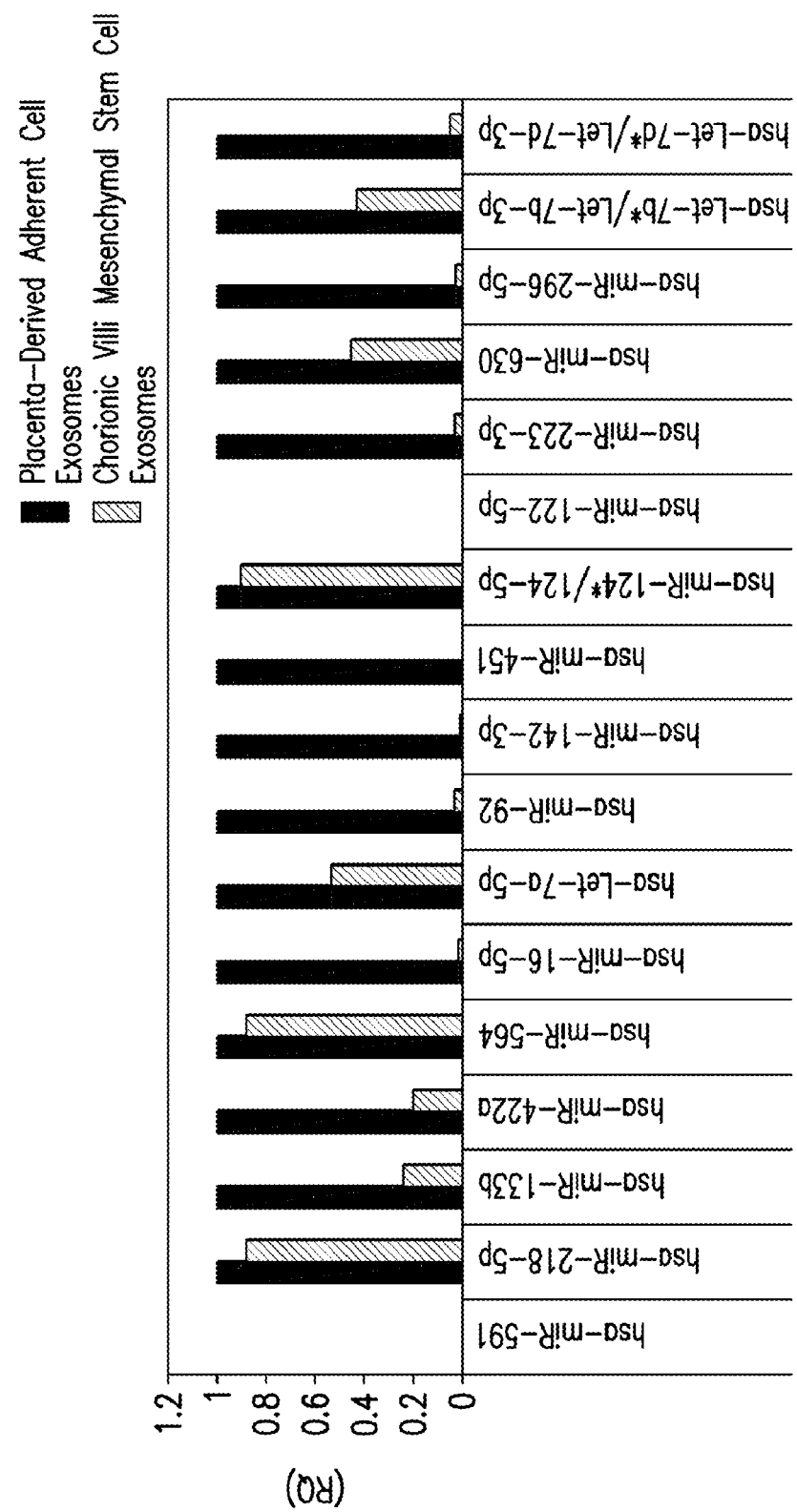

As shown in FIG. 4A, placenta-derived adherent cell exosomes contain higher levels of all miRNAs analyzed in each of the three groups as compared to chorionic villi MSCs. These data further indicate that the placenta-derived adherent cell exosomes described herein are distinct from chorionic villi mesenchymal stem cell exosomes on the basis of miRNA content. miRNAs miR-451, miR-142-3p, miR-16-5p, miR-296-5p, miR-233-3p, miR-92, Let-7d*, miR- 422a, and miR-133b all showed a difference of Ct values greater than 2 for chorionic villi mesenchymal cell exosomes as compared to placenta-derived adherent cell exosomes (see Table 2), indicating significantly higher presence of these miRNAs in placenta-derived adherent cell exosomes. Data shown are from one experiment performed in triplicate.

TABLE 2

Ct values of miRNAs from placenta-derived adherent cell exosomes and chorionic villi mesenchymal stem cell exosomes.

| miRNA Name | Placenta-Derived Adherent Cell Ct | Chorionic Villi Mesenchymal Stem Cell Ct | Difference |
| --- | --- | --- | --- |
| miR-451 | 26.906 | 37.331 | 10.425 |
| miR-142-3p | 30.405 | 38.031 | 7.626 |
| miR-16-5p | 20.264 | 26.87 | 6.606 |
| miR-296-5p | 25.017 | 30.786 | 5.769 |
| miR-223-3p | 27.951 | 33.437 | 5.486 |
| miR-92 | 19.689 | 24.958 | 5.269 |
| Let-7d* | 25.905 | 30.658 | 4.753 |
| miR-422a | 29.413 | 31.999 | 2.586 |
| miR-133b | 31.443 | 33.806 | 2.363 |

6.4.3. Placenta-Derived Adherent Cell Exosomes Contain Angiogenic Proteins

To profile the contents of placental exosomes for angiogenic secreted cytokines, an Angioplex was performed using Human Mag Bead kit, HAGP1MAG-12K (Millipore). This kit contains analytes for detecting the following 17 cytokines: Leptin, Endoglin, Follistatin, HGF, Angiopoietin-2, G-CSF, FGF-1, FGF-2, VEGF-A, VEGF-C, VEGF-D, EGF, Endothelin-1, BMP-9, IL-8, HB-EGF, and PLGF. Exosomes were analyzed according to the manufacturer's suggested protocol.

Growth Exosomes and Serum Free Exosomes were isolated as described in Example 1. The exosomes were prepared using a 100 µg protein concentration preparation in PBS, which was diluted 10.8× for angiogenesis analyte detection profiling. Exosomes were sonicated in either a water-bath to disperse the exosomes for surface marker analysis, or using a probe to lyse the exosomes for intra-exosomal analysis. As a comparison, growth medium cleared of cells ("pre-enrichment conditioned") and growth medium ultracentrifuged to remove exosomes and other debris ("exosome depleted") were analyzed using the same method.

Figure 4B:
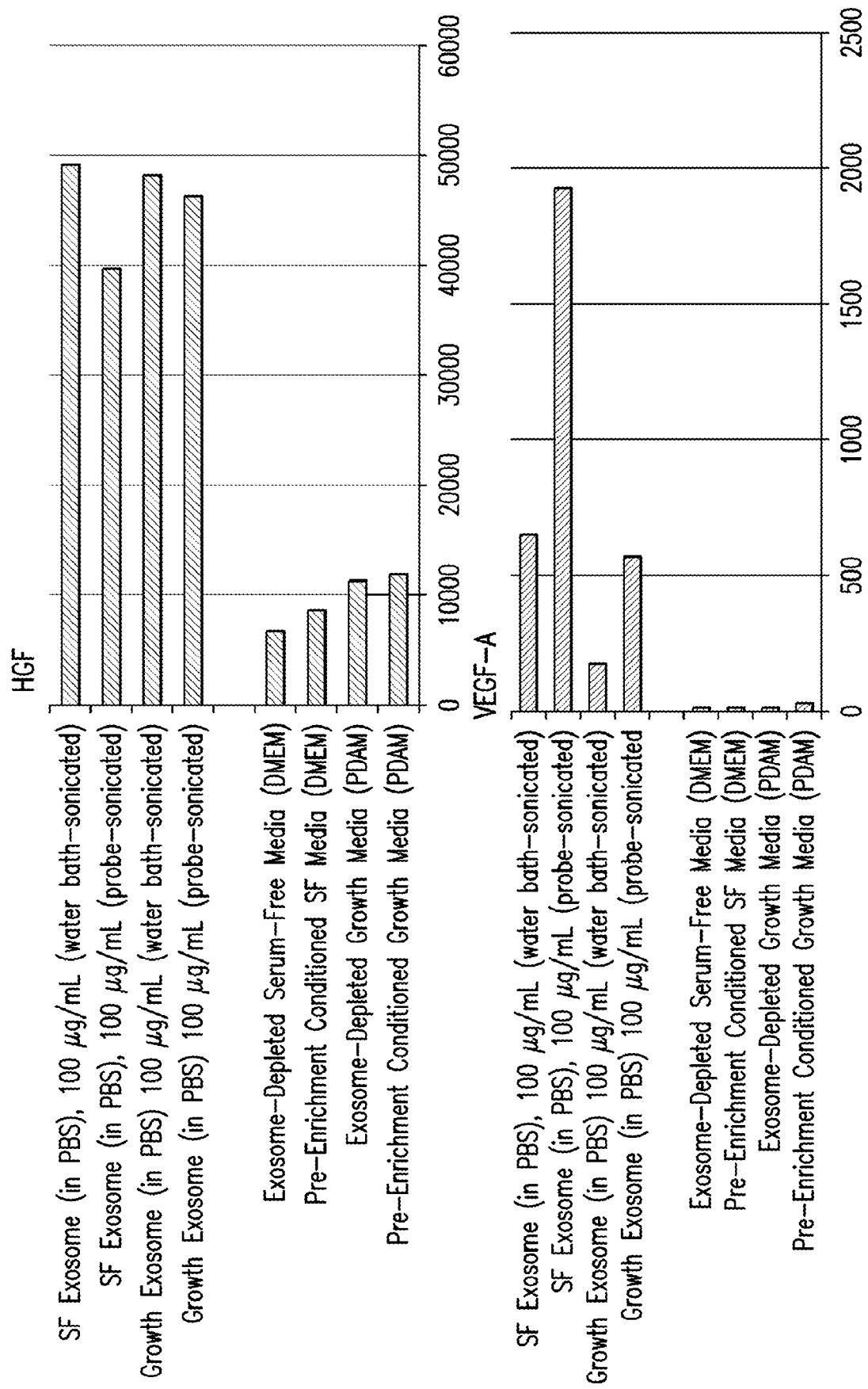
Figure 4C:
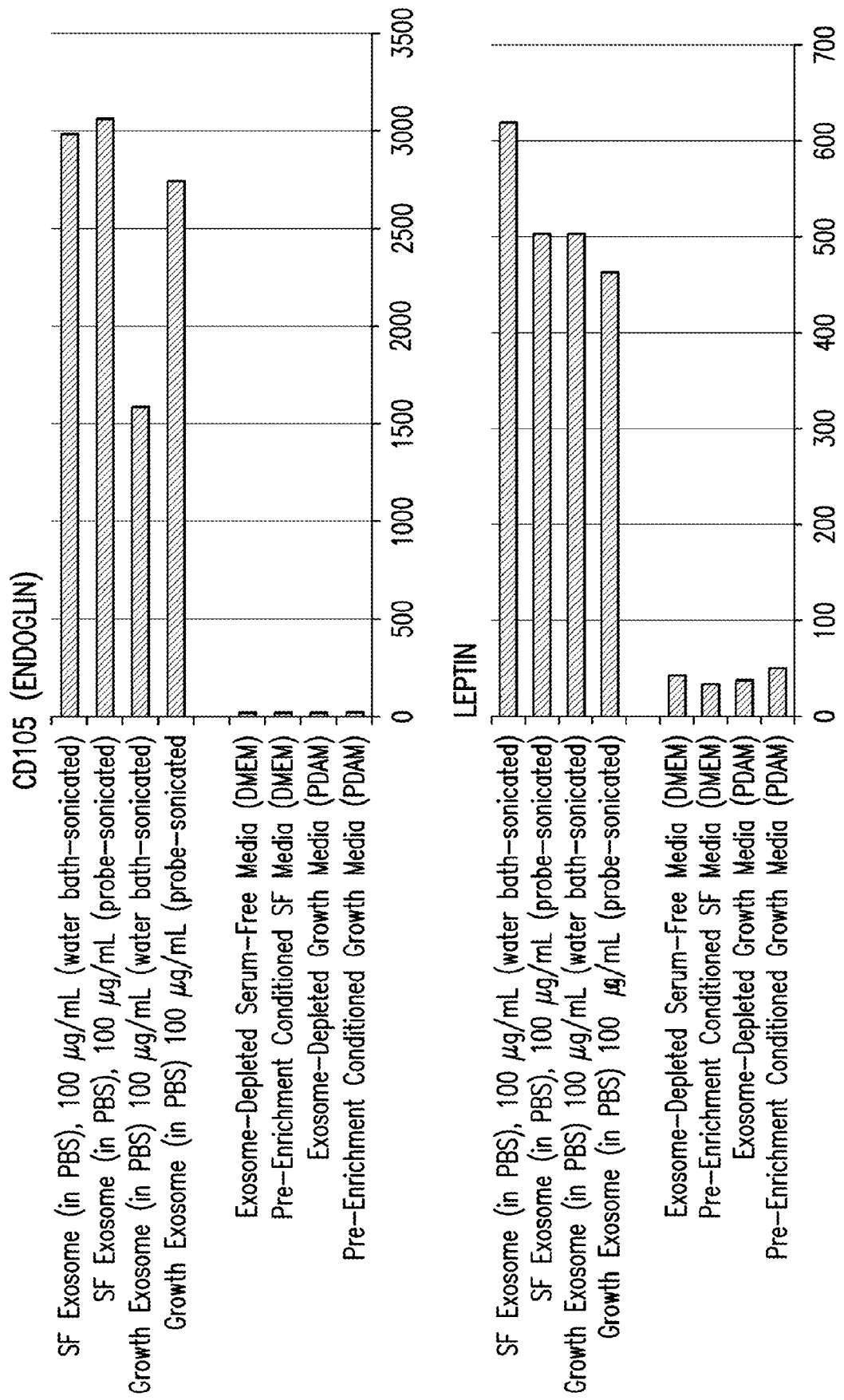

Placenta-derived adherent cell exosomes displayed detectable levels of several cytokines including HGF and VEGF-A (FIG. 4B), Endoglin and Leptin (FIG. 4C), Angiopoietin-2, G-CSF, Follistatin, FGF-2, and IL-8 (not shown). Nearly all of these cytokines were present at a lower level in all growth media tested, indicating that the cytokine levels are specifically associated with the exosomes. These data indicate that placenta-derived adherent cell exosomes contain protein factors that are known to promote angiogenesis.

Figure 5:
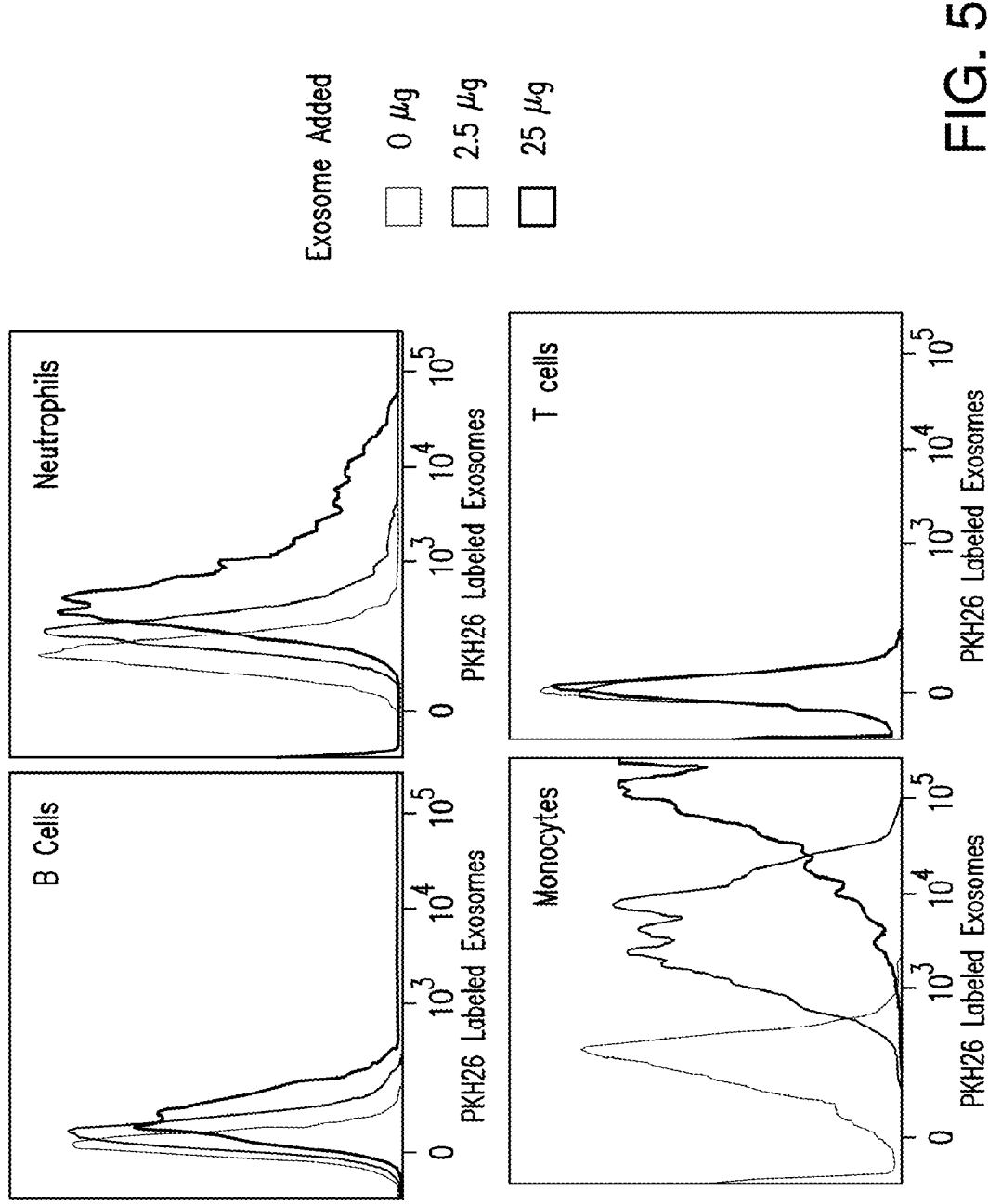
FIG. 5 shows the ability for placenta-derived adherent cell exosomes described herein to be taken up by certain cells of the blood.

6.5. Example 5: Placenta-Derived Adherent Cell Exosome Labeling and Cellular Uptake To determine if isolated placenta-derived adherent cell exosomes are capable of delivering their contents to cultured cells, exosomal uptake assays were performed using blood obtained in TruCulture tubes. Isolated placenta-derived adherent cell exosomes (see Section 6.1) were labeled with 2 µM of the fluorophore PKH26 by adding 2 µl PKH26 to 1 ml exosome suspension and incubated for 5 minutes at room temperature in the dark. Exosomes were recovered using a Centricon 10 kDa molecular weight cutoff column according to the manufacturer's instructions. Labeled exosomes were added to 200 µl TruCulture blood preparations and incubated for 24 hours at 37° C. in 5% $CO_2$. After incubation, 100 µl blood was stained with leukocyte lineage specific antibodies for 15 minutes at room temperature in the dark. After incubation, red blood cells were lysed with ACK lysing solution and washed 3× with PBS, 1% FBS. Exosome uptake on particular leukocyte populations were determined by lineage specific gating in FlowJo software and PKH26 fluorescence. As shown in FIG. 5, several lineage types stained positive for PKH26, indicating that placenta-derived adherent cell exosomes can be taken up by cultured cells.

Figure 6:
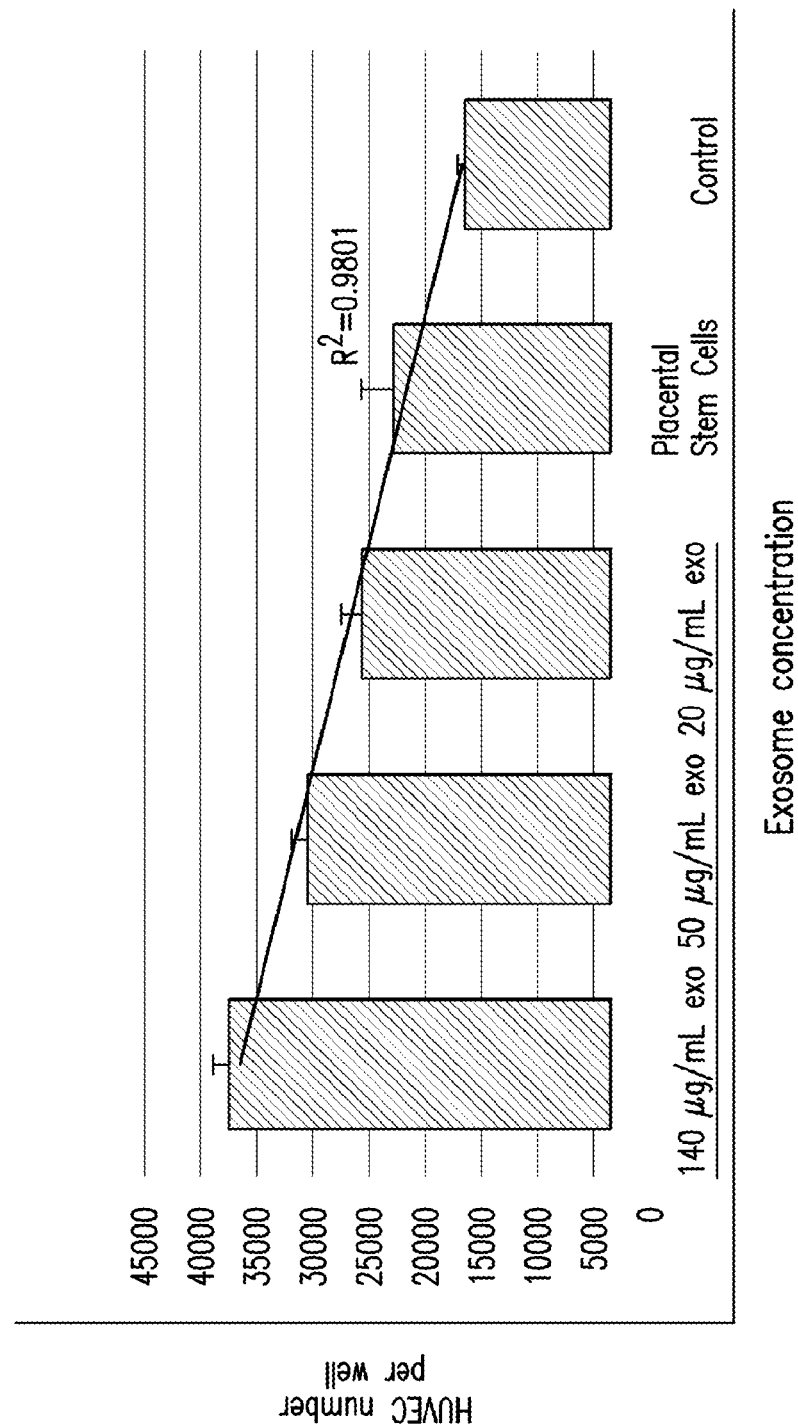
FIG. 6 shows the effects of placenta-derived adherent cell exosomes and placenta-derived adherent cells on the proliferation of human vascular endothelial cells.

6.6. Example 6: Placenta-Derived Adherent Cell Exosomes Enhance the Proliferation of Human Vascular Endothelial Cells Human Vascular Endothelial Cells (HUVECs) were plated at a concentration of 14,000 cells/well on matrigel and incubated with either increasing amounts of placenta-derived adherent cell exosomes in the absence of serum (see Section 6.1), $3 \times 10^4$ placenta-derived adherent cells in the absence of serum, or culture medium alone. As shown in FIG. 6, the proliferation of HUVECs correlated with the concentration of placenta-derived adherent cell exosomes added to the culture. These data indicate that placenta-derived adherent cell exosomes can enhance the proliferation of cultured human cells.

6.7. Example 7: Exosome-Mediated Effects on Cytokine Production in Whole Blood

6.7.1. Experimental Design

An in vitro model for cytokine expression in the blood as a result of immunogenic stimulation was used. In culture tubes, 2 ml of Myriad RBM TruCulture™ media was incubated with 1 ml of whole human blood and increasing amounts of either placenta-derived adherent cell exosomes (0, 6, 12, 24, 47 and 94 µg/ml) or placenta-derived adherent cells (2.5, 5, 10, 20 or $40 \times 10^3$ cells) for 1 hour before stimulation with 10 ng/ml lipopolysaccharide (LPS) for 24 hours. Cytokines produced in the cultured blood were detected using HCYTOMAG-60K|MILLIPLEX MAP Human Cytokine/Chemokine Magnetic Bead Panel—Immunology Multiplex Assay (Millipore)

6.7.2. Placenta-Derived Adherent Cells and Placenta-Derived Adherent Cell Exosomes Alter Cytokine Production in Whole Blood As shown in FIG. 7A, placenta-derived adherent cells and placenta-derived adherent cell exosomes reduce the levels of specific cytokines in a dose-dependent manner. The pro-inflammatory cytokines TNF-α, IL-12p40, MIP1b and IL-1B were all reduced when incubated with increasing amounts of placenta-derived adherent cells or placenta-derived adherent cell exosomes in LPS-stimulated whole blood. Conversely, MCP1 levels were increased by both placenta-derived adherent cells and placenta-derived adherent cell exosomes in stimulated whole blood, indicating that placenta-derived adherent cells and placenta-derived adherent cell exosomes can affect cytokine production in cultured cells.

6.7.3. Placenta-Derived Adherent Cells and Placenta-Derived Adherent Cell Exosomes Differentially Regulate a Subset of Cytokines in Stimulated Blood As shown in FIG. 7B, placenta-derived adherent cell exosomes do not enhance the levels of specific cytokines that are enhanced in the presence of placenta-derived adherent cells. IFN-γ, IL-6, IL-8 and GM-CSF, cytokines associated with inflammation, were not enhanced in the presence of placenta-derived adherent cell exosomes in stimulated whole blood. This finding indicates that placenta-derived adherent cell exosomes exert a differential effect on cultured blood than that of cells from which they were derived.

6.8. Example 8: Placenta-Derived Adherent Cell Exosomes Promote Angiogenesis In Vitro Human vascular endothelial cells (HUVECs) at passage 3 or 4 were plated in 48-well microtiter dishes at a density of 28,000 cells per well. Cells were maintained in 0.5 mL of either PBD or EBM-2 culture medium (Lonza) on GRF-Matrigel for 3 days. HUVECs were then incubated with different concentrations of placenta-derived adherent cell exosomes isolated from either serum-containing ("growth exosomes") or serum-free ("SF exosomes") placenta-derived adherent cell cultures. HUVEC growth patterns, including node formation and tube segment length (surrogates for angiogenic potential) were monitored every two hours for 18-19 hours total. HUVEC growth parameters were determined using IncuCyte live cell imaging system (Essen BioScience) and quantified using ImageJ.

6.8.1. Growth Exosomes and Serum Free Exosomes Promote HUVEC Tube Formation As shown in FIG. 8A, growth exosomes increased tube segment length and branch point frequency in cultured HUVECs in a dose-dependent manner. As compared to HUVECs incubated with PBS, isolated purified exosomes in concentrations ranging from 5 μg/well to 100 μg/well increased tube segment length (8A, left). Similarly, the HUVECs treated with growth exosomes had a higher number of nodes as compared to HUVECs treated with PBS (8A, right).

Similar to the results observed with the growth exosomes, placenta-derived adherent cell exosomes isolated from serum-free cultures increased HUVEC tube segment length and branch point frequency. As shown in FIG. 8B, HUVECs cultured in the presence of exosomes ranging in concentration of 5 μg/well to 100 μg/well increased tube segment length (8B, left) and branch point frequency (8B, right) as compared to HUVECs cultured in the presence of PBS. These results indicate that isolated placenta-derived adherent cell exosomes can promote vascular cell proliferation and vascular tube branching frequency in vitro, indicating a role for placenta-derived adherent cell exosomes as pro-angiogenic factors.

6.8.2. Placenta-Derived Adherent Cell Exosomes Alter Gene Expression in HUVEC Cells Passage 3 HUVEC cells (Lonza Lot 8F3265; 032514AR) were expanded to passage 4 in complete EGM-2 Media. The cells were harvested, seeded on fibronectin coated plates at high density, and allow to attach for 3 hours until ~100% confluent. Cells were cultured in the absence of serum~2 hours in EBM-2 medium. Cultured HUVECs were incubated with placenta-derived adherent cell culture supernatant, 50 μg of placenta-derived adherent cell exosomes, or culture medium as a control. HUVEC supernatant and cell lysates were collected at 4, 24, and 48 hours, and gene expression was analyzed at these early, intermediate, and late time points.

RNA was isolated using Qiagen's Rneasy Mini Kit (Cat #74134) as per manufacture's recommended protocol. 3.5 ug of RNA was reverse-transcribed using VILO RT MM and 40 ng of cDNA was analyzed by RT-PCR using Taqman Fast Universal PCR Master Mix and Taqman Human VEGF Pathway Array 96-well Fast Plates.

The results of the VEGF pathway array are shown in FIG. 8C (darker shades indicate higher expression level). Notably, HUVECs failed to express ACTA1, BAD, CASP9, MAP2K1, PLCG1, and SHC1 under any conditions, but 26/44 VEGF Pathway genes were up-regulated in HUVECs treated with placenta-derived adherent cell exosomes and/or placenta-derived adherent cell culture supernatant (FIG. 8C). Importantly, many of these genes are known to play an important role in angiogenesis.

Figure 8G:
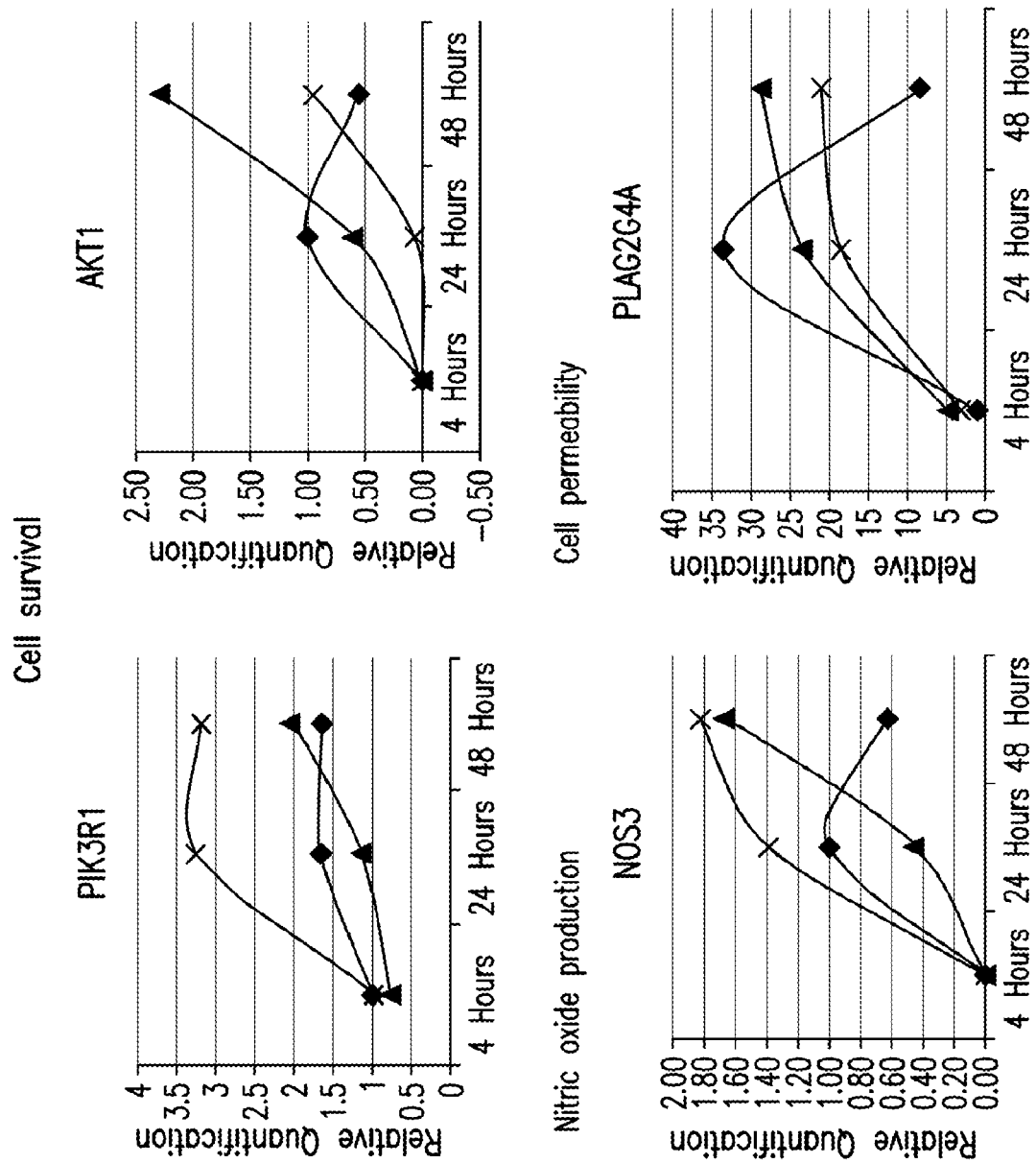

Several gene expression subclasses were altered by placenta-derived adherent cell exosomes and/or placenta-derived adherent cell culture supernatants as compared to control-treated HUVECs including genes related to (i) cell motility (FIG. 8D), (ii) cell proliferation (FIGS. 8E-F), and (iii) nitric oxide production, cell permeability, and cell survival (FIG. 8G). These results indicate that placenta-derived adherent cell exosomes are capable of altering the gene expression program of vascular cells, e.g., towards a proliferative state. These results also demonstrate that the effects of exosomes can be distinct from those induced by placenta-derived adherent cell culture supernatant.

6.8.3. Example 9: Placenta-Derived Adherent Cell Exosomes Alter Cytokine Production in Macrophages Isolated monocytes were cultured in the presence of GM-CSF for 7-10 days until differentiated into macrophages. $5 \times 10^4$ macrophages were co-cultured with placenta-derived adherent cell exosomes or placenta-derived adherent cells and 100 ng/mL LPS for 22-24 hrs. Secreted cytokines were profiled using a human immune multiplex panel (Millipore, HCYTO-MAG-60K). Assays were performed according to manufacturer's protocol using a Luminex Flex-MAP-3D system.

As shown in FIG. 9A, placenta-derived adherent cells and placenta-derived adherent cell exosomes altered the levels of specific cytokines produced by monocyte-derived macrophages in a dose-dependent manner. Specifically, TNF-α and MCP-1 were both reduced when incubated with increasing amounts placenta-derived adherent cell exosomes in the presence of LPS-stimulated macrophages. Placenta-derived adherent cells did not reduce the levels of MCP-1 in macrophage cultures.

As shown in FIG. 9B (left, center), placenta-derived adherent cell exosomes and placenta-derived adherent cells both suppressed TNF-α secretion in cultured macrophages, while placenta-derived adherent cell exosomes but not placenta-derived adherent cells broadly suppressed cytokine secretion (e.g., IL-8 secretion) in cultured macrophages. Notably, this is in contrast to the changes in cytokine expression observed in whole blood, (see Example 7). These results indicate that placenta-derived adherent cell exosomes can alter cytokine expression in cultured immune cells in a manner distinct from the cells from which the exosomes were derived. When monocyte-derived macrophages are incubated with lysed placenta-derived adherent cell exosomes, IL-8 suppression is attenuated when compared to cultures incubated with intact placenta-derived adherent cell exosomes (FIG. 9B, right). These results indicate that the exosome effect observed is due to the presence of the exosomes themselves, not merely to the mixture of components that make up the exosomes.

EQUIVALENTS

The present disclosure is not to be limited in scope by the specific embodiments described herein. Indeed, various modifications of the subject matter provided herein, in addition to those described, will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed:

1. A composition comprising exosomes derived from $CD10^+$, $CD200^+$, $CD105^+$, $CD34^-$ human placenta derived adherent cells, wherein said exosomes are $CD9^+$, $CD10^+$, $CD13^+$, $CD29^+$, $CD44^+$, $CD49b^+$, $CD49c^+$, $CD55^+$, $CD59^+$, $CD63^+$, $CD73^+$, $CD81^+$, $CD82^+$, $CD90^+$, $CD98^+$, $CD105^+$, $CD141^+$, $CD142^+$, $CD151^+$, $CD164^+$, $CD295^+$, or $CD200^+$.

2. The composition of claim 1, wherein said exosomes are $CD9^+$, $CD10^+$, $CD13^+$, $CD29^+$, $CD44^+$, $CD49b^+$, $CD49c^+$, $CD55^+$, $CD59^+$, $CD63^+$, $CD73^+$, $CD81^+$, $CD82^+$, $CD90^+$, $CD98^+$, $CD105^+$, $CD141^+$, $CD142^+$, $CD151^+$, $CD164^+$, $CD295^+$, and $CD200^+$.

3. The composition of claim 1, wherein said exosomes are additionally CD3−, CD11b−, CD14−, CD19−, CD33−, CD192−, HLA-A−, HLA-B−, HLA-C−, HLA-DR−, CD11c− or CD34−.

4. The composition of any of claim 1, wherein said exosomes are additionally CD3−, CD11b−, CD14−, CD19−, CD33−, CD192−, HLA-A−, HLA-B−, HLA-C−, HLA-DR−, CD11c and CD34−.

5. The composition of claim 1, wherein said exosomes comprise non-coding RNA molecules.

6. The composition of claim 5, wherein said RNA molecules are microRNAs.

7. The composition of claim 6, wherein said microRNAs are miR-218-Sp, miR-133b, miR-422a, miR-564, miR-16-Sp, let-7a, miR-92, miR-142-3p, miR-451, miR-124-Sp, miR-223-3p, miR-630, miR-296-Sp, let-7b-3p or let-7d-3p.

8. The composition of any of claim 1, wherein said exosomes comprise at least one marker molecule at a level at least two-fold higher than exosomes derived from mesenchymal stem cells.

9. The composition of claim 1, wherein said placenta-derived adherent cells have been passaged more than 3 times.

10. The composition of any of claim 1, wherein said placenta derived adherent cells have been maintained in culture for greater than 24 hours.

11. The composition of claim 1, wherein at least 90% of said placenta-derived adherent cells are non-maternal in origin.

12. The composition of claim 1, wherein at least 99% of said placenta-derived adherent cells are non-maternal in origin.

13. The composition of any of claim 1 that is in a form suitable for intravenous administration.

14. A composition comprising exosomes derived from $CD10^+$, $CD200^+$, $CD105^+$, $CD34^-$ human placenta-derived adherent cells, wherein said exosomes are $CD10^+$ and $CD55^+$.

* * * * *